United States Patent
Simard et al.

(10) Patent No.: US 10,533,988 B2
(45) Date of Patent: *Jan. 14, 2020

(54) METHODS FOR TREATING CENTRAL OR PERIPHERAL NERVOUS SYSTEM DAMAGE

(71) Applicants: University of Maryland, Baltimore, Baltimore, MD (US); The United States of America as Represented by the Department of Veterans Affairs, Washington, DC (US)

(72) Inventors: J. Marc Simard, Baltimore, MD (US); Mingkui Chen, Lake Forest, IL (US)

(73) Assignees: University of Maryland, Baltimore, Baltimore, MD (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/644,450

(22) Filed: Jul. 7, 2017

(65) Prior Publication Data
US 2017/0307593 A1    Oct. 26, 2017

Related U.S. Application Data

(60) Continuation of application No. 14/815,154, filed on Jul. 31, 2015, now abandoned, which is a
(Continued)

(51) Int. Cl.
| | |
|---|---|
| *A61P 9/10* | (2006.01) |
| *A61K 31/165* | (2006.01) |
| *A61K 31/565* | (2006.01) |
| *A61K 31/566* | (2006.01) |
| *G01N 33/50* | (2006.01) |
| *C12N 5/079* | (2010.01) |
| *A61K 49/00* | (2006.01) |
| *A61K 31/00* | (2006.01) |

(Continued)

(52) U.S. Cl.
CPC ......... *G01N 33/5058* (2013.01); *A61K 31/00* (2013.01); *A61K 31/175* (2013.01); *A61K 31/18* (2013.01); *A61K 31/195* (2013.01); *A61K 31/197* (2013.01); *A61K 31/403* (2013.01); *A61K 31/4015* (2013.01); *A61K 31/426* (2013.01); *A61K 31/4439* (2013.01); *A61K 31/4453* (2013.01); *A61K 31/64* (2013.01); *A61K 31/7076* (2013.01); *A61K 49/0008* (2013.01); *B01J 19/0093* (2013.01); *B32B 37/1292* (2013.01); *C07K 14/705* (2013.01); *C12N 5/0622* (2013.01); *G01N 33/5076* (2013.01); *G01N 33/6872* (2013.01); *B29L 2031/756* (2013.01); *G01N 2500/04* (2013.01); *Y10S 514/87* (2013.01)

(58) Field of Classification Search
None
See application file for complete search history.

(56) References Cited

U.S. PATENT DOCUMENTS

| | | |
|---|---|---|
| 5,047,429 A | 9/1991 | Nye |
| 5,166,162 A | 11/1992 | Masereel et al. |
| | (Continued) | |

FOREIGN PATENT DOCUMENTS

| | | |
|---|---|---|
| AU | 2003222020 A1 | 10/2003 |
| CA | 2044855 A1 | 1/1992 |
| | (Continued) | |

OTHER PUBLICATIONS

Garty, H. et al, "A simple and sensitive procedure for measuring isotope fluxes through ion-specific channels in heterogenous populations of membrane vesicles," The Jol. of Bio. Chem., vol. 256, No. 21 (1983) pp. 13094-13099.
Ren, et. al. "Altered mRNA Expression of ATP-Sensitive and Inward Rectifier Potassium Channel Subunits in Streptozotocin-Induced Diabetics Rat Herat and Aorta", J. Pharmacol Sci., 2003, vol. 93, pp. 478-483.
Proks, et al., "Inhibition of Recombinant K(ATP) Channels by the Antidiabetic Agents Midaglizole, LY397364 and LY389382," Eur J Pharmacol. Sep. 27, 2002;452(1)11-9.
Phillips, "The challenge of gene therapy and DNA delivery", Journal of Pharmacy and Pharmacology; 2001; 1169-1174; vol. 53(9).
Weith et al., "Stroke", 2001; 2029-3032; vol. 32.
(Continued)

*Primary Examiner* — Zachary C Howard
(74) *Attorney, Agent, or Firm* — Norton Rose Fulbright US LLP

(57) ABSTRACT

A composition comprising a novel $Ca^{2+}$-activated, $[ATP]_i$-sensitive nonspecific cation ($NC_{Ca-ATP}$) channel is described. The channel is found in mammalian neural cells and exhibits a different sensitivity to block by various adenine nucleotides, and is activated by submicromolar $[Ca]_i$. The $NC_{Ca-ATP}$ channel is activated under conditions of ATP depletion, which causes severe cell depolarization, followed by cell swelling. The $NC_{Ca-ATP}$ channel is regulated by a sulfonylurea receptor and is inhibited by sulfonylurea compounds glibenclamide and tolbutamide. Methods employing compositions comprising the $NC_{Ca-ATP}$ channel to screen for compounds that block the channel and the use of such antagonists as therapeutics in preventing brain swelling and damage are described. In addition, methods employing compositions comprising the Kir2.3 channel to screen for compounds that open the channel and the use of such antagonists as therapeutics in preventing brain swelling and damage are described.

18 Claims, 15 Drawing Sheets

Related U.S. Application Data continuation of application No. 14/184,947, filed on Feb. 20, 2014, now Pat. No. 9,107,932, which is a continuation of application No. 13/483,824, filed on May 30, 2012, now abandoned, which is a continuation of application No. 11/857,547, filed on Sep. 19, 2007, now Pat. No. 8,318,810, which is a continuation of application No. 11/099,332, filed on Apr. 5, 2005, now Pat. No. 7,285,574, which is a division of application No. 10/391,561, filed on Mar. 20, 2003, now abandoned.

(60) Provisional application No. 60/365,933, filed on Mar. 20, 2002.

(51) Int. Cl.
| | |
|---|---|
| *A61K 31/175* | (2006.01) |
| *A61K 31/426* | (2006.01) |
| *A61K 31/4439* | (2006.01) |
| *A61K 31/64* | (2006.01) |
| *B01J 19/00* | (2006.01) |
| *B32B 37/12* | (2006.01) |
| *C07K 14/705* | (2006.01) |
| *G01N 33/68* | (2006.01) |
| *A61K 31/18* | (2006.01) |
| *A61K 31/195* | (2006.01) |
| *A61K 31/197* | (2006.01) |
| *A61K 31/4015* | (2006.01) |
| *A61K 31/403* | (2006.01) |
| *A61K 31/4453* | (2006.01) |
| *A61K 31/7076* | (2006.01) |
| *B29L 31/00* | (2006.01) |

(56) References Cited

U.S. PATENT DOCUMENTS

| | | |
|---|---|---|
| 5,215,985 A | 6/1993 | Murphy et al. |
| 5,236,932 A | 8/1993 | Greenfield et al. |
| 5,281,599 A | 1/1994 | Murphy et al. |
| 5,451,580 A | 9/1995 | Murphy et al. |
| 5,545,656 A | 8/1996 | Loose et al. |
| 5,677,344 A | 10/1997 | Greenfield et al. |
| 5,811,393 A | 9/1998 | Klagsbrun et al. |
| 5,849,796 A | 12/1998 | Gericke et al. |
| 5,916,871 A | 6/1999 | Johnson |
| 5,929,082 A | 7/1999 | Chambers et al. |
| 5,962,645 A | 10/1999 | Keay et al. |
| 6,043,224 A | 3/2000 | Lee et al. |
| 6,056,977 A | 5/2000 | Bhagwat et al. |
| 6,100,047 A | 8/2000 | Wilkison et al. |
| 6,156,522 A | 12/2000 | Keay et al. |
| 6,180,671 B1 | 1/2001 | Freedman et al. |
| 6,184,248 B1 | 2/2001 | Lee et al. |
| 6,187,756 B1 | 2/2001 | Lee et al. |
| 6,232,289 B1 | 5/2001 | Keay et al. |
| 6,242,200 B1 | 6/2001 | Wilkison et al. |
| 6,365,577 B1 | 4/2002 | Iversen |
| 6,372,743 B1 | 4/2002 | Darrow et al. |
| 6,376,197 B1 | 4/2002 | Keay et al. |
| 6,469,055 B2 | 10/2002 | Lee et al. |
| 6,492,130 B1 | 12/2002 | Wilkison et al. |
| 6,492,339 B1 | 12/2002 | Sleevi et al. |
| 6,511,989 B2 | 1/2003 | Heitsch et al. |
| 6,569,633 B1 | 5/2003 | Wilkison et al. |
| 6,569,845 B1 | 5/2003 | Futamura et al. |
| 6,596,751 B2 | 7/2003 | Fujita et al. |
| 6,610,746 B2 | 8/2003 | Fryburg et al. |
| 6,613,785 B2 | 9/2003 | Bril et al. |
| 6,679,859 B1 | 1/2004 | Keipert et al. |
| 7,285,574 B2 | 10/2007 | Simard et al. |
| 7,877,048 B2 | 1/2011 | Kitagawa |
| 8,318,810 B2 | 11/2012 | Simard et al. |
| 2001/0003751 A1 | 6/2001 | Terashita et al. |
| 2001/0016586 A1 | 8/2001 | Guitard et al. |
| 2002/0013268 A1 | 1/2002 | Fryburg et al. |
| 2002/0016443 A1 | 2/2002 | Keay et al. |
| 2002/0016643 A1 | 2/2002 | Sakata |
| 2002/0037928 A1 | 3/2002 | Jaen et al. |
| 2002/0065315 A1 | 5/2002 | Jensen et al. |
| 2002/0081306 A1 | 6/2002 | Elliott et al. |
| 2002/0094977 A1 | 7/2002 | Robl et al. |
| 2002/0166443 A1 | 11/2002 | Haerr et al. |
| 2003/0215889 A1 | 11/2003 | Simard et al. |
| 2003/0216294 A1 | 11/2003 | Fryburg et al. |
| 2005/0009733 A1 | 1/2005 | Stephenson et al. |
| 2005/0054659 A1 | 3/2005 | Ellsworth et al. |
| 2006/0100183 A1 | 5/2006 | Simard |
| 2006/0276411 A1 | 12/2006 | Simard et al. |
| 2007/0203239 A1 | 8/2007 | Gehenne et al. |
| 2009/0130083 A1 | 5/2009 | Simard et al. |
| 2010/0092469 A1 | 4/2010 | Simard et al. |
| 2010/0311639 A1 | 12/2010 | Simard |
| 2011/0263478 A1 | 10/2011 | Simard |
| 2012/0237449 A1 | 9/2012 | Simard et al. |

FOREIGN PATENT DOCUMENTS

| | | |
|---|---|---|
| EP | 0210772 A2 | 2/1987 |
| EP | 0338415 A3 | 3/1991 |
| EP | 0467709 A3 | 7/1992 |
| EP | 1529058 A2 | 5/2005 |
| EP | 1782815 A1 | 5/2007 |
| ES | P200401628 | 6/2004 |
| JP | H09208562 A | 8/1997 |
| JP | 2004-516236 A | 6/2004 |
| WO | 1997/41857 A1 | 11/1997 |
| WO | 2001/010430 A2 | 2/2001 |
| WO | 2001/54771 | 8/2001 |
| WO | 2002/070499 A2 | 9/2002 |
| WO | 03057843 A2 | 7/2003 |
| WO | 03075933 | 9/2003 |
| WO | 2003/079987 A2 | 10/2003 |
| WO | 03079987 A2 | 10/2003 |
| WO | 2005/041877 A2 | 5/2005 |
| WO | 2006/000608 A1 | 1/2006 |
| WO | 2006/034048 A2 | 3/2006 |
| WO | 2007/011595 A2 | 1/2007 |
| WO | 2007011926 A2 | 1/2007 |
| WO | 2006/036278 A8 | 5/2007 |
| WO | 2007058902 | 5/2007 |
| WO | 2008/098160 A1 | 8/2008 |
| WO | 2009/002832 A2 | 12/2008 |
| WO | 2008/089103 A8 | 10/2009 |

OTHER PUBLICATIONS

Gribble et al., "The interaction of nucleotides with the tolbutamide block of cloned ATP-sensitive K+ channel currents expressed in Xenopus oocytes: a reinterpretation", J Physiol.; 1997; 35-45; vol. 504(Pt 1).

Plangger, "Effect of Torasemide on Intracranial Pressure, Mean Systemic Arterial Pressure, and Cerebral Perfusion Pressure in Experimental Brain Edema of the Rat", Acta Neurochir Suppl (Wien), 1994; 519-20; vol. 60.

Loffler-Walz et al., "Interaction of the diuretics torasemide and U-37883A with the K(ATP) channel in rat isolated aorta", Naunyn Schmiedebergs Arch Pharmacol.; 1998; 230-7; vol. 358(2).

Gribble, "Sulphonylurea action revisited: the post-cloning era", Diabetologia, 2003; 875-91. vol. 46(7).

Kempski, "Cerebral Edema", Semin Nephol; 2001; 303-307; vol. 21 (3); abstract only.

Unterberg, et al., "Edema and Brain Trauma", Neuroscience, 2004; 1021-1029; vol. 129.

Kaal, et al., "The Management of Brain Edema in Brain Tumors", Curr. Opin. Oncol.; 2004; 593-600; vol. 16.

Eriksson, "Preparation of liver microsomes with high recovery of endoplasmic reticulum and a low grade of contamination", Biochim Biophys Acta; 1978; 155-64; vol. 508(1).

(56) References Cited

OTHER PUBLICATIONS

Mersel et al., "Plasma membrane isolated from astrocytes in primary cultures. Its acceptor oxidoreductase properties", Biochim Biophys Acta; 1984; 144-54; vol. 778(1).
Heinemann et al., "Frontiers in Bioscience 3, d483-493", May 1, 1998, printed out from the bioscience.org website as pp. 1-24.
Benos, "Methods to study CFTR protein in vitro", Journal of Cystic Fibrosis; 2004; 79-83; vol. 3.
Dubyak, "Ion homeostasis, channels, and transporters: an update on cellular mechanisms", Adv Physiol Educ; 2004; 143-154, vol. 28.
Hambrock et al., Mg2+ and ATP dependence of K(ATP) channel modulator binding to the recombinant sulphonylurea receptor, SUR2B, Br J Pharmacol. Oct. 1998;125(3):577-83.
Heinemann et al., Isolation and structural analysis of microsomal membrane proteins, Front Biosci. May 1, 1998;3: d483-93.
Simard, et al., "Brain Oedema in Focal Ischaemia: Molecular Pathophysiology and Theoretical Implications," Lancet Neurol. Mar. 2007;6(3):258-68.
Tank, D., et al., "Isolated-patch recording from liposomes containing functionally reconstituted chloride channels from Torpedo electroplax", Proc Natl Acad Sci U S A. Dec. 1982;79(24):7749-53.
Vidal, et al., "Making sense of antisense", Eur J Cancer. Dec. 2005;41(18):2812-8. Epub Nov. 9, 2005.
Haider et al., "Identification of the PIP2-binding site on Kir6.2 by molecular modelling and functional analysis," EMBO J. Aug. 22, 2007;26(16):3749-59. Epub Aug. 2, 2007.
Simard, J. M., et al., "Endothelial Sulfonylurea Receptor 1—Regulated NC Ca—ATP Channels Mediate Progressive Hemorrhagic Necrosis Following Spinal Cord Injury"; J Clin Invest., Aug. 2007;117(8), pp. 2105-2113.
White, R. P., et al., "Cerebral Arterial Contractions Induced by Human and Bovine Thrombin", Stroke, vol. 11, No. 4, Jul. 1, 1980, pp. 363-368, XP55024008, ISSN: 0039-2499.
White, R. P., et al., "Comparison of Piroxicam, Meclofenamate, Ibuprofen, Aspirin, and Prostcyclin Efficacy in a Chronic Model of Cerebral Vasospasm", Neurosurgery, Williams & Wilkens, Baltimore, MD, vol. 12, No. 1, Jan. 1, 1983, pp. 40-46, XP000614038, ISSN 0148-396X.
Maeda, Yoshihisa, et al. "Endothelial Dysfunction and Altered Bradykinin Response Due to Oxidative Stress Induced by Serum Deprivation in the Bovine Cerebral Artery", European Journal of Pharmacology, Elsevier Science, NL, vol. 491, No. 1, Apr. 26, 2004, pp. 53-60, XP008150602, ISSN 0014-2999.
Yang, Shao-Hua, "17-beta Estradiol Can Reduce Secondary Ischemic Damage and Mortality of Subarachnoid Hemorrhage", Journal of Cerebral Blood FOLW and Metabolism, 2001, pp. 174-181, XP055024012.
Lin, et al., "17b-Estradiol Inhibits Endothelin-1 Production and Attenuates Cerebral Vasospasm After Expreimental Subarachnoid Hemorrhage", Experimental Biology and Medicine, Jun. 1, 2006, pp. 1054-1057, XP55024011, URL: http://ebm.rsmjournals.com/content/231/6/1054.full.pdf#page=1&view=FitH [retrieved Apr. 5, 2012].
Kawanabe, Yoshifumi, et al., "Effects of the Ca++-permeable Nonselective Cation Channel Blocker LOE 908 on Subarachnoid Hemorrhage-induced Vasospasm in the Basilar Artery in Rabbits", Experimental Biology and Medicine, Mar. 2003, XP008150600.
Crépel, et al., "Glibenclamide depresses the slowly inactivating outward current (ID) in Hippocampal Neurons," Canadian Journal of Physiology and Pahrmacology, 70(2):306-307, 1992.
Gribble and Ashcroft, "Sulfonylurea Sensitivity of Adenosine Triposphate-sensitive Potassium Channels from b Cells and Extrapancreatic Tissues," Metabolism, 49(10Supp2):3-6, 2000.
Grijalva, et al., "Efficacy and Safety of 4-aminopyridine in Patients with Long-term Spinal Cord Injury: A Randomized, Double-blind, Placebo-controlled Trial," Pharmacotherapy, 23(7):823-834, 2003.
Hozumi, et al., "Biochemical and Immunocytochemical Changes in Glial Fibrillary Acidic Protein After Stab Wounds," Brain Research, 524:64-71, 1990.
Liu, et al., "Suppression of Hippocampus Fos Expression and Activator Protein-1 (AP-1) Activity During Focal Cerebral Ischemia Using Antisense Strategy," Stroke, 26(1):182, 1995.
Wickelgren, "Animal Studies Raise Hopes for Spinal Cord Repair," Science, 297:178-181, 2002.
Yokoshiki, et al., "Antisense Oligodeoxynucleotides of Sulfonlurea Recepters Inhibit ATP-sensitive K+ Channels in cultured Neonatal Rat Ventricular Cells," Pflugers Arcch—Eur J Physiol, 437:400-408, 1999.
Maybaur, D.M., et al, "The ATP-sensitive Potassium-channel Inhibitor Glibenclamide Improves Outcome in an Ovine Model of Hemorragic Shock," Shock, vol. 22(4), 2004, pp. 387-391.
Simard, J. M., et al.; "Glibenclamide Reduces Inflammation, Vasogenic Edema, and Caspase-3 Activation After Subarachnoid Hemorrhage"; Journal of Cerebral Blood Flow & Metabolism (2008), 29(2) pp. 317-330.
Simard, J. M., et al.; "Sulfonylurea Receptor 1 in the Germinal Matrix of Premature Infants"; Pediatr Res.; Dec. 2008; 64(6), pp. 648-652.
Wang, H., et al., "Targeting Ischemic Stroke with a Novel Opener of ATP-Sensitive Potassium Channels in the Brain", Molecular Pharmacology, vol. 66(5), 2004, pp. 1160-1168.
Koltz, Michael T., et al; "Tandem Insults of Prenatal Ischemia Plus Postnatal Raised Intrathoracic Pressure in a Novel Rat Model of Encephalopathy of Prematurity"; J. Neurosurg. Pediatrics, Dec. 2011, vol. 8, pp. 628-639.
Kraemer, Jennifer, et al; "Perfusion Studies of Glyburide Transfer Across the Human Placenta: Implications for Fetal Safety"; American Journal of Obstetrics and Gynecology, 2006, vol. 195, pp. 270-274.
Elliott, Byron D., et al; "Comparative Placental Transport of Oral Hypoglycemic Agents in Humans: A Model of Human Placental Drug Transfer"; Am. J. Obstet. Gynecol., Sep. 1994, vol. 171, No. 3, pp. 653-660.
Elliott, Byron D., et al; "Insignificant Transfer of Glyburide Occurs Across the Human Placenta"; Oct. 1991; Am. J. Obstet. Gynecol., vol. 165, No. 4, Part 1, pp. 807-812.
Koren, Gideon; "Glyburide and Fetal Safety; Transplacental Pharmacokinetic Considerations"; Reproductive Toxicology, 2001, vol. 15, pp. 227-229.
Tosun, Cigdem, et al; "The Protective Effect of Glibenclamide in a Model of Hemorrhagic Encephalopathy of Prematurity"; Brain Sciences, 2013, vol. 3, pp. 215-238.
Mizognchi et al., "Inhibition of Carbonic Anydrases Enhanced the Recovery from Acute Experimental colitis by controlling Epithelial Registration", Abstract in: Elsevier Health Journals, p. 821, 2003.
Kawaguchi et al., "A case of hemorrhagic colitis associated with flufenamic acid aluminium", Japanese Journal of National Medical Services, 47(12):999-1003, 1993.
Gunal et al., "Estradiol Treatment Ameliorates Acetic Acid-Induced Gastric and Colonic Injuries in Rats", Inflammation, 27(6):351-359, 2003.
Ahmad et al., "Mouse cortical collecting duct cells show nonselective cation channel activity and express a gene related to the cGMP-gated rod photoreceptor channel," Proc. Natl. Acad. Sci. USA, 89: 10262-10266, 1992.
Angel et al., "The binding site for [3H]glibenclamide in the rat cerebral cortex does not recognize K-channel agonists or antagonists other than sulphonylureas," Fundam. Clin. Pharmacol, 5(2): 107-15, 1991 (abstract only).
Armijo, "Advances in the physiopathology of epilegtogenesis: molecular aspects," Rev. Neurol., 34(5): 409-29, 2002 (abstract only).
Ballerini, "Glial cells express multiple ATP binding cassette proteins which are involved in ATP release," Neuroreport, 13(14): 1789-92, 2002 (abstract only).
Baudelet et al., "Evidence for a Neuroprotective Effect of Pyrid-3-yl-sulphonyl-urea in Photochemically Induced Focal Ischaemia in Rats: Magnetic Resonance Imaging Evaluation," J. Pharm. Pharmacol., 51: 967-970, 1999.
Bevan et al, "Voltage Gasted Ionic Channels in Rat Cultured Astrocytes, Reactive Astrocytes and an Astrocyte-oligodendrocyte Progenitor Cell, " J. Physiol vol. 82, 1987, pp. 327-335.

(56) References Cited

OTHER PUBLICATIONS

Champigny et al., "A voltage, calcium, and ATP sensitive non selective cation channel in human colonic tumor cells," Biochem. Biophys. Res. Commun., 176: 1196-1203, 1991.
Chen et al., "Cell Swelling and a Nonselective Cation Channel Regulated by Internal Ca2+ and ATP in Native Reactive Astrocytes from Adult Rat Brain," J. Neurosci., 21(17): 6512-6521, 2001.
Davies, "Insulin secretagogues," Curr. Med. Res. Opin. 18 Suppl., 1: ss22-30, 2002 (abstract only).
Gopalakrishnan et al., "Pharmacological characterization of a 1,4-dihydropyridine analogue, 9-(3,4-dichorophenyl)-3,3,6,6-tetramethyl-3,4,6,7,9,10-hexahydro-1,8(2H,5H)-acridinedione (A-184209) as a novelK(ATP) channel inhibitor," Br. J. Pharmacol., 138(2): 393-99, 2003 (abstract only).
Gray et al., "Non-selective cation channel on pancreatic duct cells," Biochem. Biophys. Acta, 1029:33-42, 1990.
Gribble et al., "Differential selectivity of insulin secretagogues. Mechanisms, clinical implications, and drug interactions," J. Diabetes Complications, 17(2 Suppl): 11-5, 2003 (abstract only).
Gribble et al., "Tissue Specificity of Sulfonylureas: Studies on Cloned Cardiac and B-Cells K-ATP Channels," Diabetes, 47: 1412-1418, 1998.
Hambrock et al., "Four novel splice variants of sulfonylurea receptor 1," Am. J. Physiol. Cell Physiol., 283: C587-C598, 2002.
Hernandez-Sanchez et al., "Mice transgenically overexpressing sulfonylurea receptor 1 in forebrain resist seizure induction and excitotoxic neuron death," PNAS, 98(6): 3549-3554, 2001.
Jarvis et al., "Purinergic Mechanisms in the Nervous System Function and Disease States," Psychopharmacology: The Fourth Generation of Progress, (Kupfer, David J. et al., Lippincott 2000), found at www.acnp.org/g4/GN401000063/CH.html.
Kimelberg et al., "Astrocytic swelling in traumatic-hypoxic brain injury. Beneficial effects of an inhibitor of anion exchange transport and glutamate uptake in glial cells," Mol. Chem, Neuropathol., 11(1): 1-31, 1989 (abstract only).
Koch et al., "Mechanism of shrinkage activation of nonselective cation channels in M-1 mouse cortical collecting duct cells," J. Membr. Biol., 177(3): 231-42, 2000 (abstract only).
Koch et al., "Osmotic shrinkage activates nonselective cation (NSC) channels in various cell types," J. Membr. Biol., 168(2): 131-39, 1999 (abstract only).
Lauritzen et al., "The potassium channel opener (−)-cromakalim prevents glutamate-induced cell death in hippocampal neurons," J. Neurochem., 69(4): 1570-79, 1997 (abstract only).
Lee et al., "Direct demonstration of sulphonylurea-sensitive KATP channels on nerve terminals of the rat motor cortex," Br. J. Pharmacol., 115(3): 385-87, 1995 (abstract only).
Lee et al., "The high-affinity sulphonylurea receptor regulates KATP channels in nerve terminals of the rat motor cortex," J. Neurochem., 66(6): 2562-71, 1996 (abstract only).
Lee et al, "Upregulation of Phospolipase D in Astrocytes in Response to Transient Forebrain lschemia," GLIA vol. 30, 2000, pp. 311-317.
Liu et al., "Tenidap, a novel anti-inflammatory agent, is an opener of the inwardly rectifying K+ channel hKir2.3," Eur. J. Pharmacol., 435(2-3): 153-60, 2002 (abstract only).
Mest et al., "Glucose-induced insulin secretion is potentiated by a new imidazoline compound," Naunyn Schmledebergs Arch. Pharmacol., 364(1): 47-52, 2001.
Ono et al., "ATP and calcium modulation of nonselective cation channels in IMCD cells," Am. J. Physiol., 267: F558-F565, 1994.
Perillan et al., "Inward Rectifier K+ Channel Kir2.3 (IRK3) in Reactive Astrocytes from Adult Rat Brain," GLIA, 31: 181-192, 2000.
Perillan et al., "K+ Inward Rectifier Currents in Reactive Astrocytes from Adult Rat Brain," GLIA, 27: 213:225, 1999.
Perillan et al., "Transforming Growth Factor-B1 Regulates Kir2.3 Inward Rectifier K+ Channels via Phospholipase C and Protein Kinase C-d in Reactive Astrocytes from Adult Rat Brain," J. Biol. Chem., 277: 1974-1980, 2002.

Popp et al, "A Calcium and ATP Sensitive Nonselective Cation Channel in the Antiluminal Membrane of Rat Cerebral Capillary Endothelial Cells, " Biochimica et Biophysica Acta vol. 1108, 1992, pp. 59-66.
Proks et al., "Sulfonylurea stimulation of insulin secretion," Diabetes, 51(Suppl. 3): S368-76, 2002.
Rae et al., "A non-selective Cation Channel in Rabbit Corneal Endothelium Activated by Internal Calcium and Inhibited by Internal ATP," Exp. Eye. Res., 50: 373-384, 1990.
Schroder et al., "AMPA receptor-mediated modulation of inward rectifier K+ channels in astrocytes of couse hippocampus," Mol. Cell Neurosci., 19(3): 447-8, 2002 (abstract only).
Schubert et al., "Cascading glia reactions: a common pathomechanism and its differentiated control by cyclic nucleotide signaling," Ann. N.Y. Acad. Sci., 903: 24-33, 2000 (abstract only).
Sturgess et al., "Calcium and ATP regulate the activity of a non-selective cation channel in a rat insulinoma cell line," Pflugers Arch., 409: 607-615, 1987.
Verkhratsky et al., "Ion channels in glial cells," Brain Res. Rev., 32: 380-412, 2000.
Auger, G. et al; Purification and Partial Characterization of a Hepatocyte Antiproliferative Glycopeptide, Journal of Cellular Biochemistry, (1989) vol. 40, pp. 439-451.
Keay, S., et al.; Bladder Epithelial Cells from Patients with Interstitial Cystitis Produce an Inhibitor of Heparin-Binding Epidermal Growth Factor-Like Growth Factor Production, The Journal of Urology (Dec. 2000) vol. 164, pp. 2112-2118.
Keay, S., et al.; Changes in human bladder epithelial cell gene expression asscoiated with interstitial cystitis or antiproliferative factor treatment, Physiol. Genomics (2003) vol. 14, pp. 107-115.
Keay, S., et al.; Current and future directions in diagnostic markers in interstitial cystitis, Intern'l J. of Urology (2003) vol. 10, pp. S27-230.
Keay, S., et al.; Decreased In Vitro Proliferation of Bladder Epithelial Cells from Patients with Interstitial Cystitis, The Journal of Urology (2003) vol. 61, pp. 1278-1284.
Rashid, H., et al; Interstitial cystitis antiproliferative factor (APF) as a cell-cycle modulator, BMC Urology (2004) 4:3, pp. 1-5.
Zhang C. et al; Comparison of APF Activity and Epithelial Growth Factor Levels in Urine from Chinese, African-American, and White American Patients with Intestitial Cystitis, Urology (2003) vol. 61, pp. 897-901.
Parson, C.L., et al., "Role of Toxic Urine in Interstitial Cystitis", Journal of Urology (1990) vol. 143, p. 373A.
Beier-Holgersen, R., "The in vitro cytotoxicity of urine from patients with interstitial cystitis", Journal of Urology (Jan. 1994), vol. 151, pp. 206-207.
Nishimura, M., et al., "Cerebral ATM-Sensitive Potassium Channels During Acute Reduction of Carotid Blood Flow", American Heart Assoc., (1995), vol. 25, 1069-1074.
Simard, J., et. al., "Molecular pathophysiology of brains edema in focal ischemia—a focused review" (Apr. 8, 2006) pp. 1-483.
Hambrock, A., et al., "Mg2+ and ATP dependence of KATP Channel Modulator Binding to the Recombinant Sulphonylurea Receptor, SUR2B", British Journal of Pharm. 91998), vol. 125, pp. 577-583.
Torsemide Tablets Package Insert, pp. 1-2.
Torsemide advanced consumer drug information, pp. 1-10. http://www.drugs.com/MMX/Torsemide.html. (May 2006).
Jin et al., "Altered gene expression and increased bursting activity of colonic smooth muscle ATP-sensitive K+ channels in experimental colitis", Am. J. Physiol. Gastrointest. Liver Physiol., 287:G274-G285, 2004.
Daneshmand et al., "Chronic lithium administration ameliorates 2,4,6-trinitrobenzene sulfonic acid-induced colitis in rats; potential role for adenosine triphosphate sensitive potassium channels", Gastroenterology and Hepatology, 26:1174-1181, 2011.
Nieuwenhuijs et al., "Hepatic ischemia-reperfusion injury: roles of Ca2+ and other intracellular mediators of impaired bile flow and hepatocyte damage"; Digestive Diseases and Sciences, Jun. 2006, vol. 51(6); 1087-102.
Pompermayer et al.; "The ATP-sensitive potassium channel blocker glibenclamide prevents renal ischemia/reperfusion injury in rats"; Kidney International, May 2005, vol. 67(5); 1785-96.

(56) References Cited

OTHER PUBLICATIONS

Kim, H.J., et al.; "Anthocyanins from soybean seed coat inhibit the expression of TNF-alpha-induced genes associated with ischemia/reperfusion in endothelial cell by NF-kappaB-dependent pathway and reduce rat myocardial damages incurred by ischemia and reperfusion in vivo"; FEBS Letters 580, Jan. 20, 2006; pp. 1391-1397.

Fagan et al., "Targets for vascular protection after acute ischemic stroke"; Stroke. Sep. 2004;35(9):2220-5. Epub Jul. 29, 2004.

Gürsoy-Özdemir et al., "Role of Endothelial Nitric Oxide Generation and Peroxynitrite Formation in Reperfusion Injury After Focal Cerebral Ischemia"; Stroke. 2000;31:1974.

Manley et al., "Aquaporin-4 deletion in mice reduces brain edema after acute water intoxication and ischemic stroke"; Nature Medicine 6, 159-163 (2000).

Morris et al., "Extension of the Therapeutic Window for Recombinant Tissue Plasminogen Activator With Argatroban in a Rat Model of Embolic Stroke"; Stroke. 2001;32:2635-2640.

Nilius et al., "Transient Receptor Potential Cation Channels in Disease"; Physiol. Rev. 87: 165-217, 2007.

Pisano et al., "Undersulfated, low-molecular-weight glycol-split heparin as an antiangiogenic VEGF antagonist"; Glycobiology 2005 15(2):1C-6C.

Rosenberg et al., "TIMP-2 reduces proteolytic opening of blood-brain barrier by type IV collagenase" Brain Res—Apr. 3, 1992; 576(2): 203-7.

Ullrich et al., "Comparison of functional properties of the Ca2+-activated cation channels TRPM4 and TRPM5 from mice"; Cell Calcium. Mar. 2005; 37(3):267-78.

Grand, T., et al; "9-Phenanthrol Inhibits Human TRPM4 But Not TRPM5 Cationic Channels"; British Journal of Pharmacology; 2008, vol. 153, vol. 1697-1705.

Matsuo, Michinori, et al; "Different Binding Properties and Affinities for ATP and ADP Among Sulfonylurea Receptor Subtypes, SUR1, SUR2A, and SUR2B*"; The Journal of Biological Chemistry; Sep. 15, 2000; vol. 275, No. 37, pp. 28757-28763.

Nilius, Bernd, et al; "Intracellular Nucleotides and Polyamines Inhibit the Ca2+-Activated Cation Channel TRPM4b"; Pfulgers Arch—Eur. J. Physiol., 2004, vol. 448; pp. 70-75.

Babenko; Audrey P., et al; "Pharmaco-topology of Sulfonylurea Receptors"; The Journal of Biological Chemistry (Accelerated Publication); vol. 275, No. 2, Jan. 14, 2000, pp. 717-720.

Earley, Scott, et al; "Protein Kinase C Regulates Vascular Myogenic Tone Through Activation of TRPM4"; American Physiological Society; Feb. 9, 2007; vol. 292; pp. H2613-H2622.

Woo, Seung Kyoon, et al; "The Sulfonylurea Receptor 1 (Sur1)-Transcient Receptor Potential Melastatin 4 (Trpm4) Channel"; The Journal of Biological Chemistry, Feb. 1, 2013, vol. 288, No. 5, pp. 3655-3667.

Pfeiffer et al., "Controlled extension of oral antidiabetic therapy on former insulin dependent diabetics by means of the combined i.v.. Glibenclamide-glucose-response test", Diabetologia, 8:41-47, 1972.

Wise, "New clinical guidelines for stroke published", BMJ, 320:823, 2000.

Bereczki et al., "Mannitol for acute stroke (Review)", Cochrane Database of Systematic Reviews, Issue 3, p. 1-20, 2009.

Chen et al., "Fenamates protect neurons against ischemic and exitotoxic injury in chick embryo retina", Neuroscience Letters, 242(3):163-166, 1998.

Riddle, "Editorial: sulfonylureas differ in effects on ischemic preconditioning—is it time to retire glyburide?", The Journal of Clincial Endocrinology & Metabolism, 2003, 88(2):528-530.

Gurke et al., "Mechanisms of ischemic preconditionin in skeletal muscle", Journal of Surgical Research, 2000, 94:18-27.

Greenwood et al., "Comparison of the effects of fenamates on Ca-activated chloride and potassium currents in rabbit portal vein smooth muscle cells" Biritish Journal of Pharmacology, 116:2939-2948, 1995.

Schmidt et al., "Endocrine and metabolic consequences of spinal injuries", Chapter 18, Spinal Coard Medicine; Principles and Practices, pp. 221-235, 2002.

Launary et al., "TRPM4 Regulates Calcium Oscillations After T Cell Activation", Science, 306(5700):1374-1377, 2004.

Definition of "infusion" from www.merriam-webster.com, printed on Apr. 10, 2013, 1 pages as printed.

Heurteaux et al., "Alpha-Linolenic Acid and Riluzole Treatment Confer Cerebral Protection and Improce Survival After Focal Brain Ischemia", Neuroscience, 137:241-251, 2006.

Simard et al., Comparative effects of glibenclamide and riluzole in a rat model of severe cervical spinal cord injury, Experimental Neurology, 233:566-574, 2012.

Demion et al., "TRPM4, a Ca2+-activated nonselective cation channel in mouse sino-atrial nod cells ", Cardiovasuclar Research, 73:531-538, 2007.

Khansari, "An investigation of the neuroprotective properties of fenamate NSAIDs, against experimental models of Ischemic stroke", Dissertation Abstracts International, 68:11B, 197 pages, 2007.

Khansari and Halliwell, "Evidence for neuroprotection by the fenamate NSAID, mefenamic acid", Neurochemistry International, 55:683-688, 2009.

Klose et al., "Fenamates as TRP channel blockers: mefenamic acid selectively blocks TrPM3", British Journal of Pharmacology, 162:1757-1769, 2011.

Pirollo and Chang, "Targeted Delivery of Small Interfering RNA: Approaching Effetive Cancer Therapies", Cancer Res., 68(5):1247-1250, 2008.

Hausmann, "Post-traumatic inflammation following spinal cord injury", Spinal Cord, 41:369-378, 2003.

Woodcock, "The role of markers of inflammation in traumatic brain injury", Frontiers in Neurology, 4:1-18, 2013.

Hugelshofer, "Neuroinflammation after Subarachnoid Hemorrhage: The Role of Microglia", UniversitatsSpital Zurich Institut fur Neuropathologie & Klinik fur Neurochirurgie, p. 1-18, 2013.

Hallevi, "Inflammatory response to intraventricular hemorrage: Time course, magnitude and effect of t-PA," Journal of the Nurological Science, 315:93-95, 2012.

Kunte et al., "Sulfonylureas Improve Outcome in Patients With Type 2 Diabetes and Acute Ischemic Stroke", Stroke, 38(9):2526-2530, 2007.

Liang et al., Neurosurg Focus, 22(5):E2, pp. 1-16, 2007.

Gavin, "Management of Diabetes Mellitus During Surgery", West J M. 151:525-529, 1989.

Vestergaard et al., "Relative fracture risk in patients with diabetes melitus, and the impact of insulin and oral antidiabetic medication on relative fracture risk", Diabetologia, 48:1292-1299, 2005.

Inder and Volpe, "Mechanisms of Perinatal Brain Injury", 5 Semin, Neonatol. 3, 2000.

Wright et al., Evidence from Multicenter Networks on the Current Use and Effectiveness of Antenatal Corticosteroids in Low Birth Weight Infants, Am. J Obstet. Gynecol., 173:263, 1995.

Egarter et al., "Antibiotic Treatment in Preterm Premature Rupture of Membranes and Neonatal Morbidity: A Metaanalysis", Am. J. Obstet. Gynecol., 174:589, 1996.

Huss et al., "Differentiation of canine bone marrow cells with hemopoietic characteristics from an adherent stromal cell precursor", Proc natl. Acad. Sci USA, 92:748-752, 1995.

Zhu, Q., et al., "Modulation by Nucleotides of Binding Sites for [3H]Glibenclamide in Rat Aorta and Cardiac Ventricular Membranes", J. of Cardiovascular Pharm., (2001), vol. 37, pp. 522-531.

Walaas et al., PCPP-260, A Purkinje Cell-Specific Cyclic AMP-Regulated Membrane Phosphoprotein of Mr 260,000, J Neurosci. Apr. 1986;6(4):954-61.

Favre, I., et al., "Reconstitution of Native and Cloned Channels into Planar Bilayers", Methods in Enzymology, (1999) vol. 294, pp. 287-304.

Simard, J. M., et al., "Newly Expressed SUR1-regulated NCca-ATP Channel Mediates Cerebral Edema after Ischemic Stroke", Nature Medicine (Apr. 2006) vol. 12, No. 4, pp. 433-440.

Jamme, I., et al., "Focal cerebral ischaemia induces a decrease in activity and a shift in ouabain affinity of Na +, K +-ATPase isoforms

(56) References Cited

OTHER PUBLICATIONS without modifications in mRNA and protein expression", Brain Research (1999) vol. 810, pp. 132-142.
Chen, M., et al., "Glial and Other Non-Neuronal Cell Specification and Differentiation IV", Society for Neuroscience, (2000) vol. 26, pp. 791.1.
Rosenberg, "Ischemic brain edema." Prog Cardiovasc Dis. Nov.-Dec. 1999; vol. 42(3):209-16.
APO-Glibenclamide Data Sheet, Medsafe (New Zealand Medicines and Medical Devices Safety Authority), published Jun. 16, 1999, 6 pages; online http://www.medsafe.govt.nz/Profs/DataSheet/a/Apoglibenclamidetab.htm.
Slikker et al., "Session IV: Models of Neurotoxicity and Neuroprotection, Questions for Dr. Banik", Ann NY Acad Sci; 2003; 993; 159-160.
Sribnick et al., "Estrogen as a Neuroprotective Agent in the Treatment of Spinal Cord Injury", Ann. N.Y. Acad. Sci., vol. 993;. 2003;125-133.
Weih et al., "Sulfonylurea Drugs Do Not Influence Initial Stroke Severity and In-Hospital Outcome in Stroke Patients With Diabetes", Stroke. 2001; vol. 32(9):2029-2032.
Yong et al., "In vitro Antitumor Activity of Cromakalim in Human Brain Tumor Cells," Pharmacology 1994; vol. 49:69-74.
Yune et al., "Systemic Administration of 17?-Estradiol Reduces Apoptotic Cell Death and Improves Functional Recovery following Traumatic Spinal Cord Injury in Rats", Journal of Neurotrauma. Mar. 1, 2004, 21(3): 293-306.
Gagliardino, J.J. et al.; Inhibitory effect of sulfonylureas on protein phosphatase activity in rat pancreatic islets; Acta Diabetol (1997) 34:6-9; Springer-Verlang 1997.
Medline Plus® Merriam Webster Medical Dictionary, main entry: par.en.ter.al, online <http://www2.merriam-webster.com/cgi-bin/mwmednlm>; 2005; 1 page.
Rothstein et al, "Neuroprotective strategies in a model of chronic glutamate-mediated motor neuron toxicity," J Neurochem. Aug. 1995;65(2):643-51.
Sang et al., "ATP sensitive potassium channels are involved in the protective effect of ischemic preconditioning on spinal cord in rabbits"; Chinese Pharmacological Bulletin, 2003, Issue 12, 1362-1365.
Khan Hussein Hamed, et al., "Comparison of Therapeutic Effects by K+ Channel Opener Minoxidil and Blocker Glyburide on Cerebral Ischemia Produced by MCAO and Levo-thyroxine in Rats"; Journal of China Pharmaceutical University; Jan. 2000; vol. 31(4); pp. 289-293.
Aguilar-Bryan et al., "Cloning of the beta cell high-affinity sulfonylurea receptor: a regulator of insulin secretion," Science, 268: 423-426, 1995.
Bareyre et al., "Inflammation, degeneration and regeneration in the injured spinal cord: insights from DNA microarrays," Trends Neurosci., 26(10): 555-563, 2003.
Bartholdi et al., "Expression of pro-inflammatory cytokine and chemokine mRNA upon experimental spinal cord injury in mouse: an in situ hybridization study," Eur. J. Neurosci., 9(7): 1422-1438, 1997.
Csanady et al., "Ca(2+)- and voltage-dependent gating of Ca(2+)- and ATP-sensitive cationic channels in brain capillary endothelium," Biophys. J., 85: 313-327, 2003.
Chen, et al., "Functional Coupling between Sulfonylurea Receptor Type 1 and a Nonselective Cation Channel in Reactive Astrocytes from Adult Rat Brain," J. Neurosci., 23: 8568-8577, 2003.
Copin et al., "70-kDa heat shock protein expression in cultured rat astrocytes after hypoxia: regulatory effect of almitrine," Neurochem. Res., 20(1): 11-15, 1995.
Currie et al., "Benign focal ischemic preconditioning induces neuronal Hsp70 and prolonged astrogliosis with expression of Hsp27," Brain Res., 863(1-2): 169-181, 2000.
Fujita et al., "Molecular aspects of ATP-sensitive K+ channels in the cardiovascular system and K+ channel openers," Pharmacol. Ther., 85: 39-53, 2000.

Inagaki et al., "A family of sulfonylurea receptors determines the pharmacological properties of ATP-sensitive K+ channels," Neuron, 16: 1011-1017, 1996.
Isomoto et al., "A novel sulfonylurea receptor forms with BIR (Kir6.2) a smooth muscle type ATP-sensitive K+ channel," J. Biol. Chem., 271: 24321-24324, 1996.
Kakimura et al., "Microglial activation and amyloid-beta clearance induced by exogenous heat-shock proteins," FASEB J., 16(6): 601-603, 2002.
Lee et al., "Differential neuroprotection from human heat shock protein 70 overexpression in in vitro and in vivo models of ischemia and ischemia-like conditions," Exp. Neurol., 170(1): 129-139, 2001.
Matz et al., "Heme-oxygenase-1 induction in glia throughout rat brain following experimental subarachnoid hemorrhage," Brain Res., 713(1-2): 211-222.
Mautes et al., "Co-induction of HSP70 and heme oxygenase-1 in macrophages and glia after spinal cord contusion in the rat," Brain Res., 883(2): 233-237, 2000.
Mautes et al., "Sustained induction of heme oxygenase-1 in the traumatized spinal cord," Exp. Neurol., 166(2): 254-265, 2000.
Nichols et al., "Adenosine diphosphate as an intracellular regulator of insulin secretion," Science, 272: 1785-1787, 1996.
Papadopoulos et al., "Over-expression of HSP-70 protects astrocytes from combined oxygen-glucose deprivation," Neuroreport, 7(2): 429-432, 1996.
Regan et al., "Heme oxygenase-1 induction protects murine cortical astrocytes from hemoglobin toxicity," Neurosci. Lett., 282(1-2): 1-4, 2000.
Shyng et al., "Regulation of KATP channel activity by diazoxide and MgADP. Distinct functions of the two nucleotide binding folds of the sulfonylurea receptor," J. Gen. Physiol., 110: 643-654, 1997.
Song et al., "GeneChip analysis after acute spinal cord injury in rat," J. Neurochem., 79(4): 804-815, 2001.
Xu et al., "HSP70 protects murine astrocytes from glucose deprivation injury," Neurosci. Lett., 224(1): 9-12, 1997.
Chen et al., "A Calcium-Activated Nonspecific Cation Channel in Reactive Astrocytes from Adult Rat Brain," Society for Neuroscience Abstracts, vol. 26, No. 1-2, Abstract No. 791.1, 2000 [abstract].
Simard, et al., "Regulation by Sulfanylurea Receptor Type 1 of a Non-selective Cation Channel Involved in Cytotoxic Edema of Reactive Astrocytes," J. Neurosurg. Anesthesiol., 16(1): 98-9, 2004.
Suarez-Isla, B., et al. "Single-Channel Recordings from Purified Acetylcholine Receptors Reconstitute in Bilayers Formed at the Tip of Patch Pipets," American Chemical Society (1983) pp. 2319-2323.
Salvail, Dany, et al., "Direct modulation of tracheal Cl-channel activity by 5,6- and 11, 12-EET," Amer. Physio. Soc. (1998) pp. L432-L441.
Biochimica et Biophysica ACTA, Biomembranes, vol. 508 (1978) pp. 155-164.
Sharma, R.V., et al., "Isolation and characterization of plasma membranes from bovine carotid arteries." Amer. Physio. Soci. (1996) pp. C65-C75.
Eben-Brunnen, J., et al., "Lentil Lectin Enriched Microsomes from the Plasma Membrane of the Human B-Lymphocyte cell Line H2LCL Carry a Heavy Load of Type-1 Porin", Biol. Chem., vol. 379, (1998) pp. 1419-1426.
Garcia, Ann Maria, et al., "Channel-mediated monovalent cation fluxes in isolated sarcoplasmic reticulum vesicles," J. Gen. Physiol., vol. 83, (Jun. 1984) pp. 819-839.
Nelson, N., et al., "Reconstitution of purified acetylcholine receptors with functional ion channels in planar lipid bilayers", Proc. Natl. Acad. Sci., Sci. USA, vol. 77, No. 5 (May 1990) pp. 3057-3061.
Suarez-Isla, B., et al, "Single calcium channels in native sarcoplasmic reticulum membranes from skeletal muscle." Proc. Nat'l. Acad. Sci., USA, vol. 83, (Oct. 1986) pp. 7741-7745.
Schindler, H. et al., "Functional acetylcholine receptor from Torpedo marmorata in planar membranes," Proc. Nat'l. Acad. Sci. USA, vol. 77, No. 5, (May 1980) pp. 3052-3056.

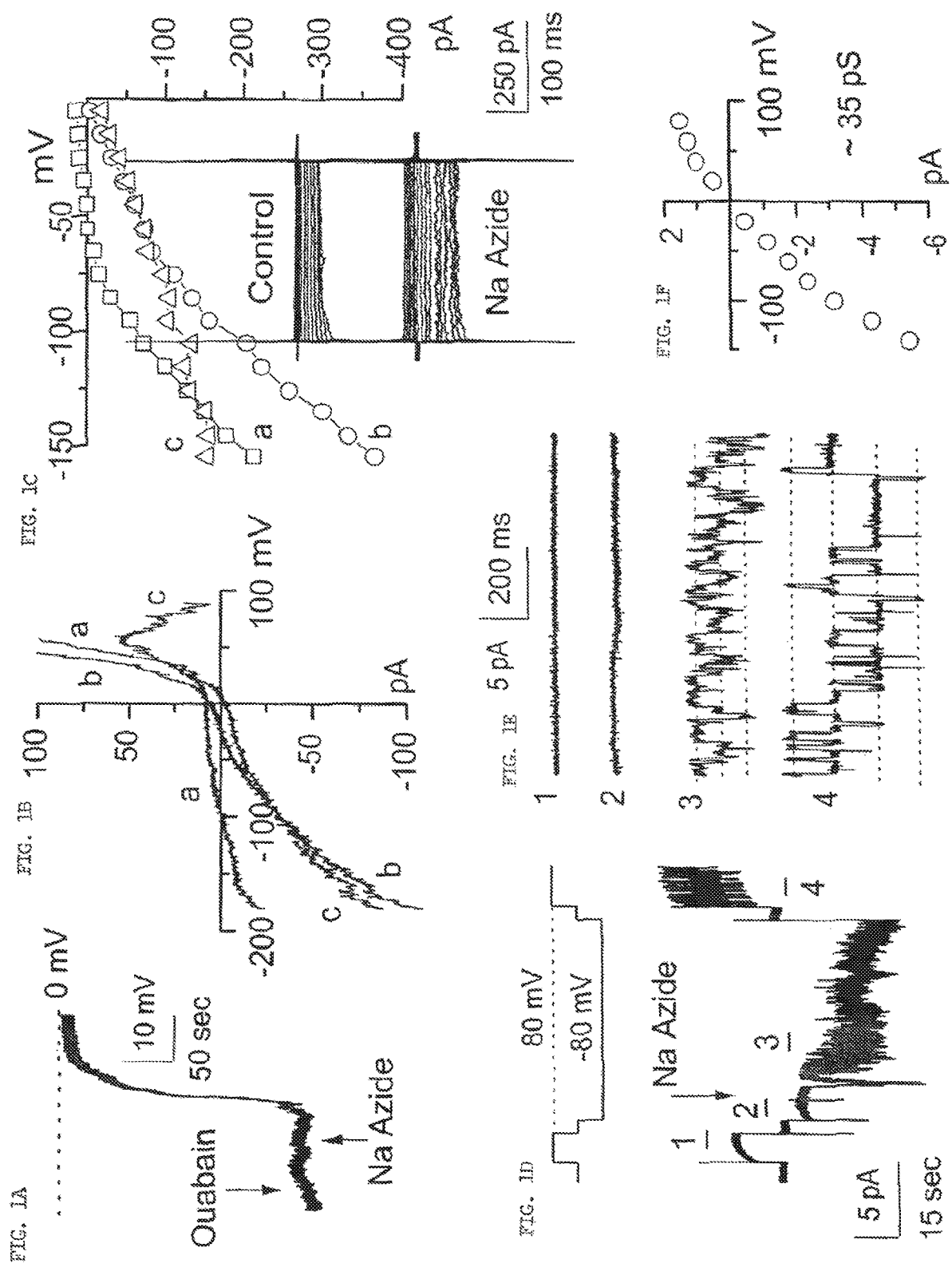

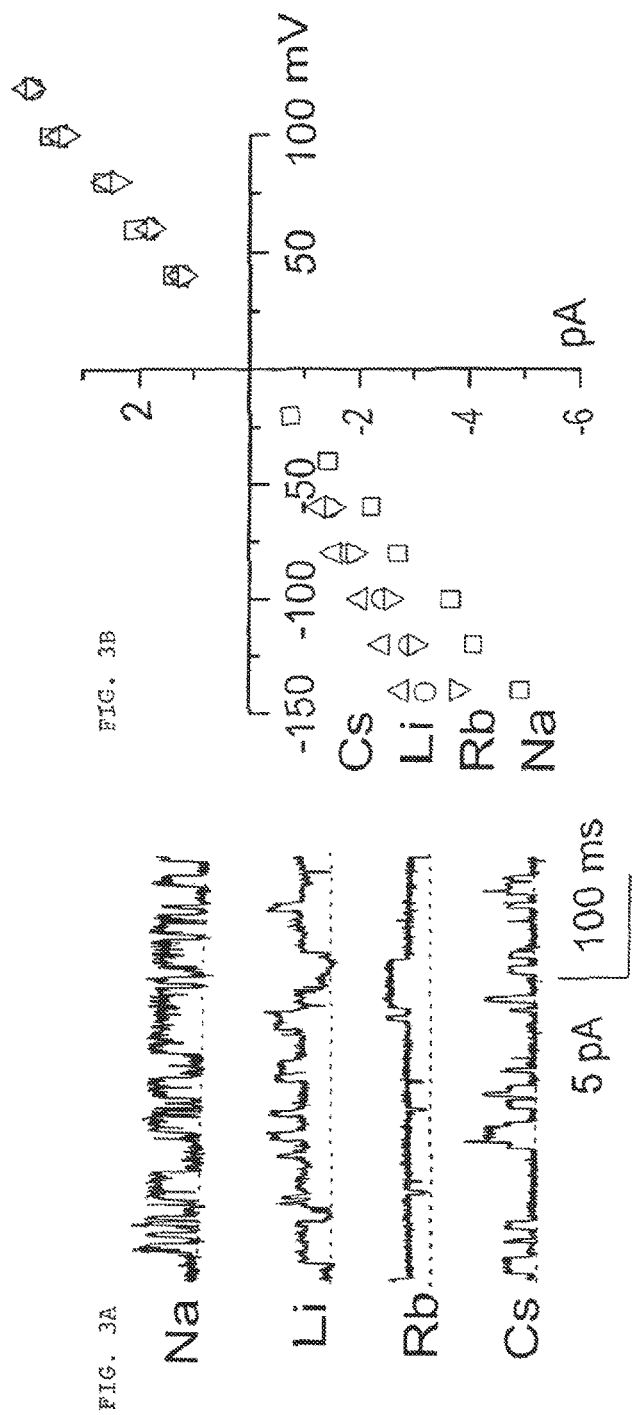
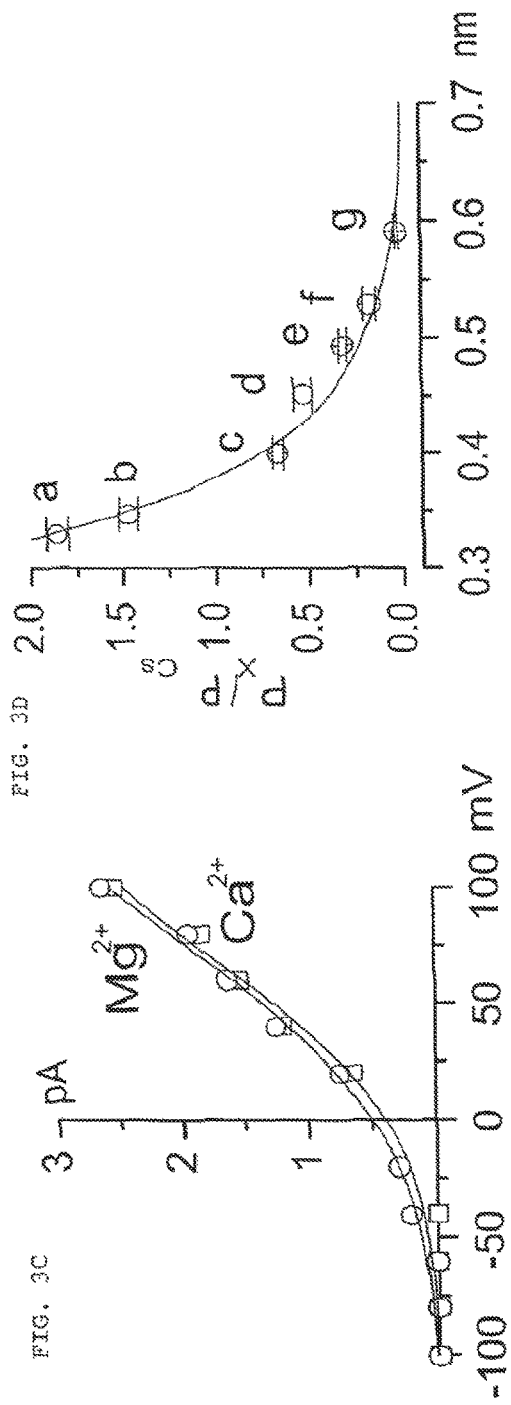
FIG. 3A
FIG. 3B
FIG. 3C
FIG. 3D 1 2 3 4 5 6

1 2 3 4 5 6

Use of Sulfonylurea Compounds as Treatment for Brain Swelling

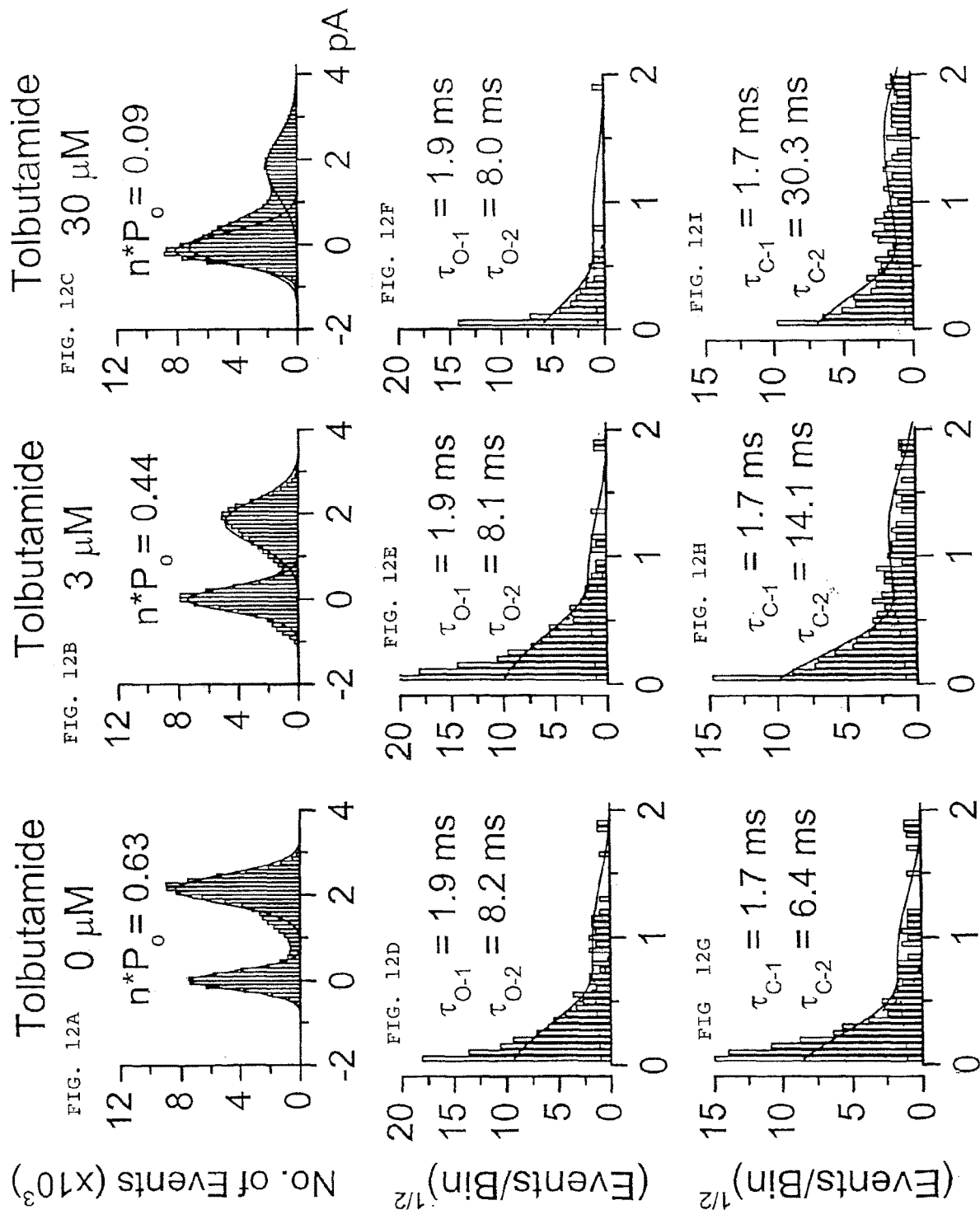

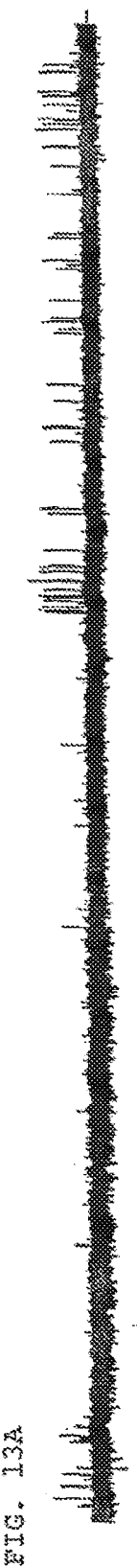
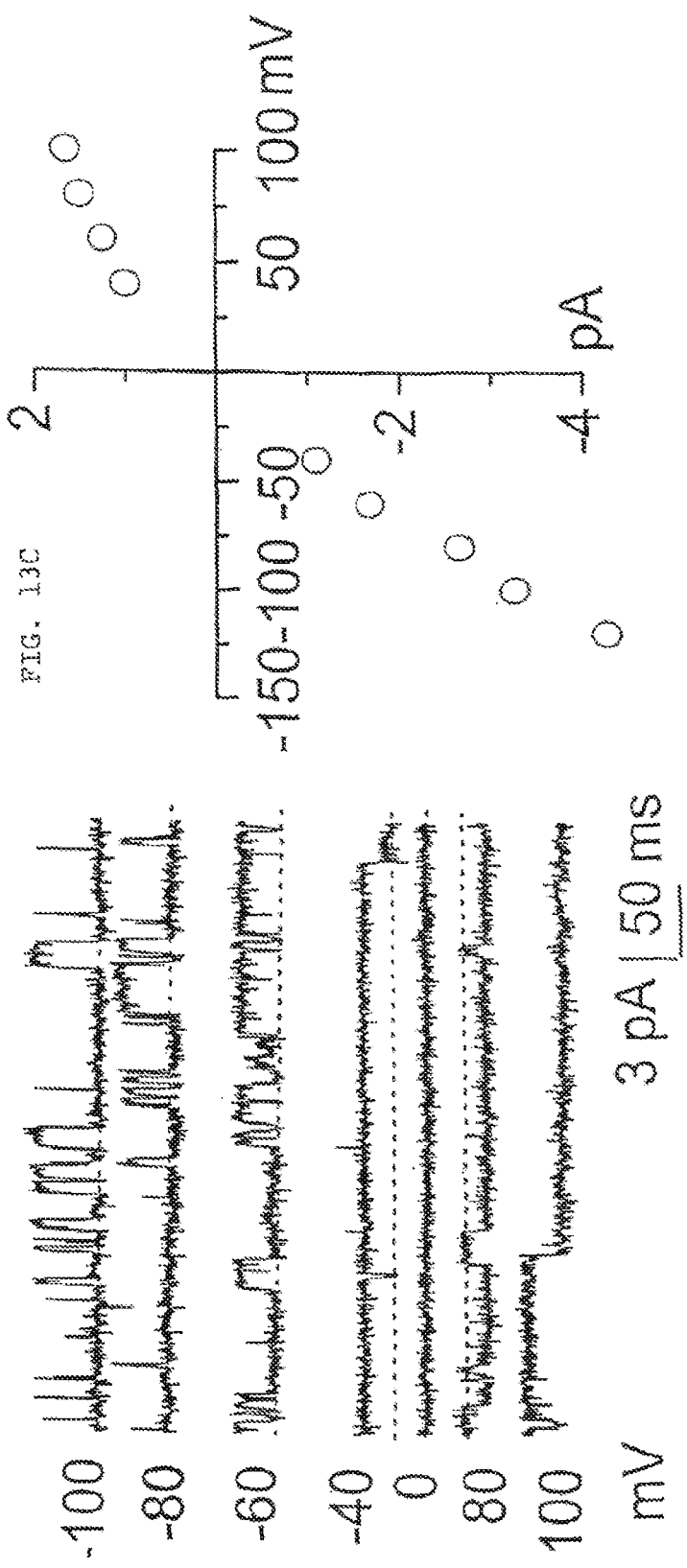
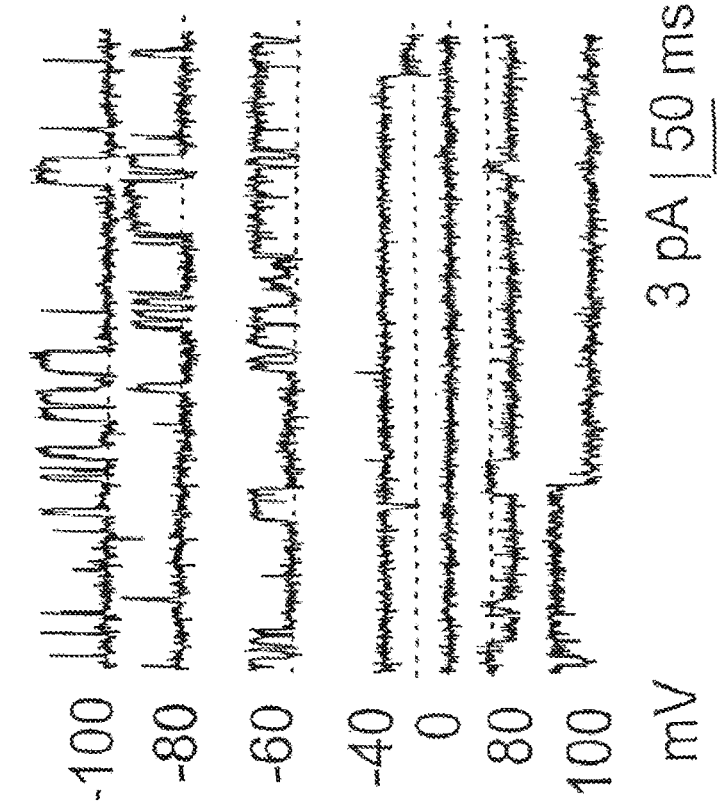

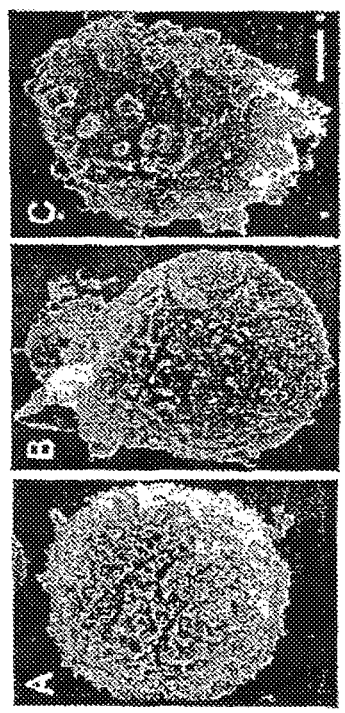

METHODS FOR TREATING CENTRAL OR PERIPHERAL NERVOUS SYSTEM DAMAGE

CROSS-REFERENCE TO RELATED APPLICATIONS

This application is a Continuation of U.S. patent application Ser. No. 11/099,322, filed on Apr. 5, 2005, which is a Divisional of U.S. patent application Ser. No. 10/391,561, filed on Mar. 20, 2003, which claims priority to U.S. Provisional Patent Application No. 60/365,933, filed on Mar. 20, 2002, all of which applications are incorporated by reference herein in their entirety.

FIELD OF THE INVENTION

The present invention relates to a novel ion channel found in neural cells which participates in the cation flux involved in cell swelling. The invention also provides a method of screening for compounds that inhibit the activity of the ion channel. Methods to screen for and identify antagonists of the $NC_{Ca-ATP}$ channel are provided. The invention further provides therapeutic methods for using compounds and compositions that inhibit the ion channel activity to inhibit or prevent the swelling of neural cells in brain. It has been discovered that neural cell swelling is mediated by the opening of a novel non-selective monovalent cationic ATP sensitive channel (the $NC_{Ca-ATP}$ channel) and that this channel is coupled to sulfonylurea receptor type 1. Moreover, it has been found that neural cell swelling and cell death, particularly astrocyte swelling, can be inhibited by blocking the $NC_{Ca-ATP}$ channel of the present invention, particularly by antagonizing receptors coupled to this channel, such as antagonizing the SUR1. The invention also encompasses the use of such compounds and compositions, that modulate $NC_{Ca-ATP}$ channel activity to treat brain swelling. The present invention relates to methods for the treatment of brain swelling that results from brain trauma or cerebral ischemia, due to neural cell swelling and cell death.

BACKGROUND OF THE INVENTION

Following traumatic brain injury and stroke, the normal response of the surrounding brain is to mount a cellular response that includes formation of reactive astrocytes that are believed to be important to "contain" and "clean-up" the injury site. Swelling of neural cells is part of the cytotoxic or cell swelling response that characterizes brain damage in cerebral ischemia and traumatic brain injury, and is a major cause of morbidity and mortality. See, Staub et al., 1993; Kimelberg et al., 1995. A number of mediators have been identified that initiate swelling of neural cells, including elevation of extracellular $K^+$, acidosis, release of neurotransmitters and free fatty acids. See, Kempski et al., 1991; Rutledge and Kimelberg, 1996; Mongin et al., 1999. Cytotoxic edema is a well-recognized phenomenon clinically that causes brain swelling, which worsens outcome and increases morbidity and mortality in brain injury and stroke.

Mechanisms underlying apoptotic death of reactive astrocytes have been studied. See, Tanaka et al., 2000; Yu et al., 2001. The mechanisms responsible for necrotic cell death have not been characterized. Apoptotic cell death is preceded by cell shrinkage and net loss of $K^+$. See, Yu et al., 1997; Yu et al., 1999. By contrast, in necrotic cell death, the plasma membrane is ruptured, causing cytosolic contents to be released and thereby triggering tissue inflammation. See, Leist and Nicotera, 1997. Necrotic cell death may be more deleterious to nearby viable tissues, given the secondary inflammatory damage that is initiated.

Necrotic cell death is initiated by osmotic swelling following influx of $Na^+$, the major extracellular osmolyte. In most cell types, accumulation of $Na^+$ intracellularly is regarded as a passive process that does not require activation of specific effectors but that is due instead to defective outward Na' pumping under conditions of low $[ATP]_i$. See, Leist and Nicotera, 1997; Trump et al., 1997. Cell blebbing or swelling, an indication of intracellular Na' overload, is generally regarded as an early sign of necrotic cell death. See, Leist and Nicotera, 1997; Majno and Joris, 1995.

Inhibition of ATP synthesis or ATP depletion also causes neural cell swelling, blebbing and, if sufficiently severe, plasma membrane disruption and cell death. See, Jurkowitz-Alexander et al., 1993. The mechanisms of neural cell swelling associated with ATP-depletion remained incompletely characterized. See, Lomneth and Gruenstein, 1989; Juurlink et al., 1992; Rose et al., 1998.

One potential mechanism would be changes in $Na^+$ and $K^+$ concentration due to inhibition of the $Na^+/K^+$-ATPase pump. However, an equivalent degree of osmotic swelling induced by ouabain-mediated inhibition of the $Na^+/K^+$-ATPase pump in neural cells does not produce large depolarization, blebbing or cell death. See, Jurkowitz-Alexander et al., 1992; Brismar and Collins, 1993. Failure of the $Na^+/K^+$-ATPase pump, therefore, is not the mechanism critical to swelling of neural cells. None of these studies have identified the cellular mechanism instrumental in the cell swelling that is associated with brain damage in cerebral ischemia and traumatic brain injury.

One subtype of ATP sensitive cation channel is the non-selective cation channel, which are channels that are sensitive to $Ca^{2+}$ and ATP. More specifically, non-selective cation channels are activated by intracellular $Ca^{2+}$ ($[Ca^{2+}]_i$ and inhibited by intracellular ATP ($[ATP]_i$). Although $Ca^{2+}$ and ATP sensitive cation channels had been identified in a number of non-neural cell types, they have not been identified in astrocytes or any other neural cells. See, Sturgess et al., 1987; Gray and Argent, 1990; Rae et al., 1990; Champigny et al., 1991; Popp and Gogelein, 1992; Ono et al., 1994, each of which is hereby incorporated by reference in its entirety. These non-astrocyte channels comprise a heterogeneous group with incompletely defined characteristics. They exhibit single-channel conductances in the range of 25-35 pS, discriminate poorly between $Na^+$ and $K^+$, are impermeable to anions, for the most part impermeable divalent cations, and they are blocked by similar concentrations of the adenine nucleotides ATP, ADP and AMP on the cytoplasmic side. The function of these non-selective ATP sensitive cation channels in these non-neural cell types remains enigmatic, in part because unphysiological concentrations of $Ca^{2+}$ are generally required for channel activation.

Another subtype of ATP sensitive cation channel is the ATP-sensitive potassium channel (KAP channels) in pancreatic β cells. One class of insulin secretagogues, the antidiabetic sulfonylureas, are used to inhibit these $K_{ATP}$ channels and stimulate insulin release in diabetes mellitus. See, Lebovitz, 1985. Antidiabetic sulfonylureas mediate their effect on $K_{ATP}$ channels via a high affinity sulfonylurea receptor (SUR). See, Panten et. al., 1989; Aguilar-Bryan et. al., 1995. Several isoforms of the SUR, termed SUR1, SUWA, S W B, and SUR2C, have been identified and cloned. See, Aguilar-Bryan et. al., 1995; Inagaki et. al., 1996; Isomoto et. al., 1996; Lawson, 2000. These receptors belong to the ATP-binding cassette (ABC) transporter family, of which the cystic fibrosis transmembrane conductance regulator (CFTR), another ion channel modulator, is also a member. See, Higgins, 1992; Aguilar-Bryan et. al., 1995. Notably, the CFTR has major therapeutic importance, since its genetic absence causes cystic fibrosis, a fatal disease.

The sulfonylurea receptor imparts sensitivity to antidiabetic sulfonylureas such as glibenclamide and tolbutamide. Also, SUR is responsible for activation of the potassium channel by a chemically diverse group of agents termed $K^+$ channel openers (SUR-activators), such as diazoxide, pinacidil, and cromakalin. See, Aguilar-Bryan et. al., 1995; Inagaki et. al., 1996; Isomoto et. al., 1996; Nichols et. al., 1996; Shyng et. al., 1997b. In various tissues, molecularly distinct SURs are coupled to distinct channel moieties to form different $K_{ATP}$ channels with distinguishable physiological and pharmacological characteristics. The $K_{ATP}$ channel in pancreatic β cells is formed from SUR1 linked with a K+ channel, whereas the cardiac and smooth muscle $K_{ATP}$ channels are formed from SUR2A and SUR2B, respectively, linked to K+ channels. See, Fujita ad Kurachi, 2000.

Thus, a need exists for a physiological target instrumental in the cell swelling that is associated with brain damage in cerebral ischemia and traumatic brain injury and in the consequent morbidity and mortality. There is also a need for specific treatments for the cytotoxic edema that causes brain swelling, which worsens outcome and increases morbidity and mortality in brain injury and stroke. Also there exists a need for therapeutic compounds capable of modulating the activity of this target in order to prevent brain damage. The present invention is directed to a newly characterized non-selective calcium and ATP sensitive monovalent cation channel, termed the $NC_{Ca-ATP}$ channel, which is present in neural cells and linked to an SUR. The present invention further provides a method to screen for or identify antagonists to $NC_{Ca-ATP}$ channel activity. Further, the present invention provides a method for the therapeutic use of antagonists, such as sulfonylureas and other SUR1 blockers, to inhibit this channel's activity and thereby prevent neural cell swelling and cell death and the concomitant nervous system damage that includes brain swelling and brain damage.

SUMMARY OF THE INVENTION

The invention is based, in part, on the discovery of a specific channel, the $NC_{Ca-ATP}$ channel, which is expressed in reactive neural cells after brain trauma. The present invention is directed to purified compositions containing a novel $Ca^{2+}$-activated, $[ATP]_i$-sensitive nonspecific cation channel, hereinafter the $NC_{Ca-ATP}$ channel. In a preferred embodiment of the present invention, the compositions comprise mammalian neural cells or membrane preparations expressing the $NC_{Ca-ATP}$ channel, most preferably the mammalian neural cells are freshly isolated reactive astrocytes. A preferred example of such a purified composition containing the $NC_{Ca-ATP}$ channel is a membrane preparation derived from native reactive astrocytes. As demonstrated herein, when neural cells expressing the $NC_{Ca-ATP}$ channel are depleted of intracellular ATP, the $NC_{Ca-ATP}$ channel opens and the cells swell and die. However, if the $NC_{Ca-ATP}$ channel is blocked on such cells, the cells do not swell and die. The invention is also based, in part, on the discovery that the $NC_{Ca-ATP}$ channel is regulated by a type 1 sulfonylurea receptor, and that antagonists of this receptor are capable of blocking the $NC_{Ca-ATP}$ channel and inhibit neural cell swelling.

The $NC_{Ca-ATP}$ channel of the present invention is distinguished by certain functional characteristics, the combination of which distinguishes it from known ion channels. The characteristics that distinguish the $NC_{Ca-ATP}$ channel of the present invention include, but are not necessarily limited to, the following: 1) it is a non-selective cation channels that readily allows passage of Na, K and other monovalent cations; 2) it is activated by an increase in intracellular calcium, and/or by a decrease in intracellular ATP; 3) it is regulated by sulfanylurea receptor type 1 (SUR1), which heretofore had been considered to be associated exclusively with $K_{ATP}$ channels such as those found in pancreatic β cells.

More specifically, the $NC_{Ca-ATP}$ channel of the present invention has a single-channel conductance to potassium ion (K+) between 20 and 50 pS. The $NC_{Ca-ATP}$ channel is also stimulated by $Ca^{2+}$ on the cytoplasmic side of the cell membrane in a physiological concentration range, where said concentration range is from $10^{-8}$ to $10^{-5}$ M. The $NC_{Ca-ATP}$ channel is also inhibited by cytoplasmic ATP in a non-physiological concentration range, where said concentration range is from $10^{-1}$ to 10 M. The $NC_{Ca-ATP}$ channel is also permeable to the following cations; $K^+$, $Cs^+$, $Li^+$, $Na^+$; to the extent that the permeability ratio between any two of said cations is greater than 0.5 and less than 2.

The invention relates to assays designed to screen for compounds or compositions that modulate the $NC_{Ca-ATP}$ channel, particularly compounds or compositions that act as antagonists of the channel, and thereby modulate neural cell swelling and the concomitant brain swelling. To this end, cell-based assays or non-cell based assays can be used to detect compounds that interact with, e.g., bind to, the outside (i.e., extracellular domain) of the $NC_{Ca-ATP}$ channel and/or its associated SUR1. The cell-based assays have the advantage in that they can be used to identify compounds that affect $NC_{Ca-ATP}$ channel biological activity (i.e., depolarization). The invention also provides a method of screening for and identifying antagonists of the $NC_{Ca-ATP}$ channel, by contacting neural cells with a test compound and determining whether the test compound inhibits the activity of the $NC_{Ca-ATP}$ channel. In one embodiment, methods for identifying compounds that are antagonists of the $NC_{Ca-ATP}$ are provided. In one embodiment, therapeutic compounds of the present invention, including $NC_{Ca-ATP}$ antagonists, are identified by the compound's ability to block the open channel or to prevent channel opening, by quantifying channel function using electrophysiological techniques to measure membrane current through the channel. $NC_{Ca-ATP}$ antagonists include compounds that are $NC_{Ca-ATP}$ channel inhibitors, $NC_{Ca-ATP}$ channel blockers, SUR1 antagonists, SUR1 inhibitors, and/or a compounds that reduce the magnitude of membrane current through the channel. In this embodiment, channel function can be measured in a preparation of neural cells from a human or animal, and the test compound can be brought into contact with the cell preparation by washing it over the cell preparation in solution. The invention further provides a method of screening for sulfonylurea compounds that may act as antagonists of the $NC_{Ca-ATP}$ channel.

The present invention relates to drug screening assays to identify compounds for the treatment of brain swelling, such as the swelling that occurs after brain injury or cerebral ischemia by using the $NC_{Ca-ATP}$ channel as a target. The invention also relates to compounds that modulate neural cell swelling via the $NC_{Ca-ATP}$ channel. The present invention also relates to the treatment of brain swelling by targeting the $NC_{Ca-ATP}$ channel.

The invention also encompasses agonists and antagonists of the $NC_{Ca-ATP}$ channel, including small molecules, large molecules, and antibodies, as well as nucleotide sequences that can be used to inhibit $NC_{Ca-ATP}$ channel gene expression (e.g., antisense and ribozyme molecules). An antagonists of the $NC_{Ca-ATP}$ channel includes compounds capable of (1) blocking the channel, (2) preventing channel opening, and/or (3) reducing the magnitude of membrane current through the channel.

The invention also encompasses the use of such compounds and compositions, that modulate $NC_{Ca-ATP}$ channel activity to treat brain swelling. Further provided is a method of preventing brain swelling and the resulting brain damage through the therapeutic use of antagonists to the $NC_{Ca-ATP}$ channel. In one embodiment, the therapeutic antagonist can be administered to or into the brain. Such administration to the brain includes injection directly into the brain, particularly in the case where the brain has been rendered accessible to injection due to trauma to the skull. The invention further provides the therapeutic use of sulfonylurea compounds as antagonists to the $NC_{Ca-ATP}$ channel to prevent cell swelling in brain. In one embodiment the sulfonylurea compound is glibenclamide. In another embodiment, the sulfonylurea compound is tolbutamide.

BRIEF DESCRIPTION OF THE FIGURES

FIG. 1 (comprised of FIGS. 1A, 1B, 1C, 1D, 1E and 1F); FIG. 1A shows whole cell current clamp recording before and after exposure to ouabain and before and after exposure to $N_aN_3$. FIG. 1B shows whole cell voltage-clamp recordings during ramp pulses (a) before and (b) after exposure to $NaN_3$; (c) is the difference current. FIG. 1C shows whole cell voltage-clamp recordings during step pulses (a) before and (b) after exposure to $N_aN_3$; (c) is the difference current. FIG. 1D shows cell-attached patch recording of single ion channel openings induced by $N_aN_3$ at membrane potentials of (3) −80 mV and (4) 80 mV, compared to control patches at membrane potentials of (1) 80 mV and (2) −80 mV. FIG. 1E shows the cell-attached patch currents of FIG. 1D, shown at higher time resolution. FIG. 1F shows the cell-attached patch single-channel current-voltage relationship.

FIG. 2 (comprised of FIGS. 2A and 2B)

FIG. 3 (comprised of FIGS. 3A, 3B, 3C and 3D); FIG. 3A shows single channel currents recorded in an inside-out patch with various alkaline ions substituting for $K^+$ in the pipette; dotted line indicates channel closing. FIG. 3B is a plot of channel amplitude vs. membrane potential with various alkaline ions substituting for $K^+$ in the pipette. FIG. 3C is a plot of channel amplitude measured in inside-out patches vs. voltage with $Ca^{2+}$ and $Mg^{2+}$ substituting for $K^+$ in the pipette. To estimate channel pore size, FIG. 3D is a plot illustrating the relationship between the permeability (relative to $Cs^+$) and the molecular radius of a series of monovalent organic cations, which included: (a) methanolmine, (b) guanidium, (c) ethanolamine, (d) diethylamine, (e) piperazine, (f) Tris, and (g) N-methylglucamine, data indicating an equivalent pore size of 0.67 nm.

FIG. 4 (comprised of FIGS. 4A and 4B)

FIG. 5. (comprised of FIGS. 5A and 5B)

FIG. 9 (comprised of FIGS. 9A and 9B) shows that the channel activator diazoxide can elicit channel activities under outside-out patch recording configuration.

FIG. 10 (comprised of FIGS. 10A, 10B and 10C)

FIG. 11 (comprised of FIGS. 11A and 1 1B) shows that sulfonylurea compounds inhibit channel activities.

FIG. 12 (comprised of FIGS. 12A, 12B, 12C, 12D, 12E, 12F, 12G, 12H and 12I); FIGS. 12A, 12B and 12C show the probability of channel opening in the presence of 0 µM, 3 µM, and 30 µM tolbutamide, respectively.

FIGS. 12D, 12E and 12F show the distribution of open channel dwell times in the presence of 0 µM, 3 µM, and 30 µM tolbutamide, respectively.

FIGS. 12G, 12H and 12I show the distribution of closed channel dwell times in the presence of 0 µM, 3 µM, and 30 µM tolbutamide, respectively.

FIG. 13 (comprised of FIGS. 13A, 13B and 13C) FIG. 13A shows outside-out patch recordings with diazoxide applied to the extracellular side of the membrane.

FIG. 13B shows current records at higher temporal resolution after application of diazoxide and at different membrane potentials.

FIG. 13C shows a plot of mean single channel amplitudes at the different potentials studied; the slope indicates 35 pS conductance of glibenclamide-sensitive channel.

FIGS. 14A, 14B and 14C are scanning electron micrographs of freshly isolated native reactive astrocytes. FIG. 14A shows the cells when formaldehyde-glutaraldehyde fixation was initiated under control conditions; FIG. 14B shows the cells fixed 5 min after exposure to 1 mM NaN3. FIG. 14C shows the cells fixed 25 min after exposure to 1 mM NaN3. Bar, 12 μm.

FIG. 15 (comprised of FIGS. 15A, 15B and 15C)

DETAILED DESCRIPTION OF THE PREFERRED EMBODIMENT

Figure 2B:
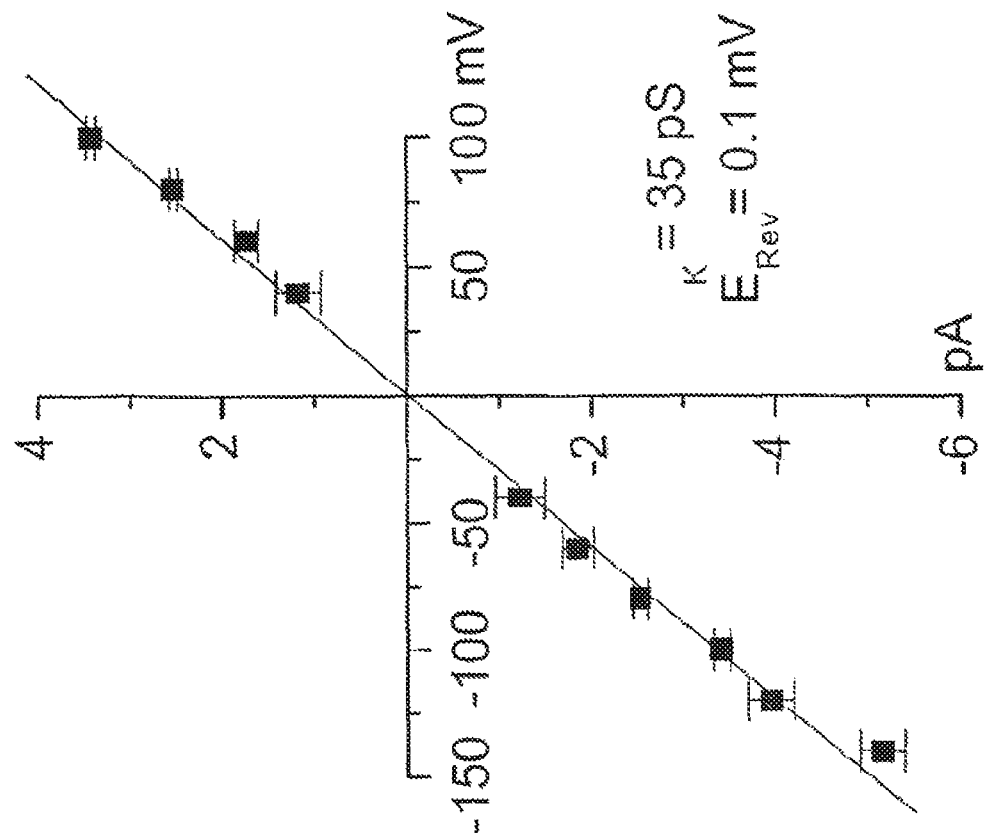
FIG. 2B is a plot of inside-out patch single channel amplitude vs. membrane potentials.

Some of the preferred embodiments of the present invention will be described in detail with reference to the attached drawings.

This invention may be embodied in many different forms and should not be construed as being limited to the embodiments set forth herein.

The present invention relates to a novel ion channel whose function underlies the swelling of mammalian neural cells, such as in response to ATP depletion; the use of the channel to screen for channel inhibitors, and the use of inhibitors of the channel function to prevent this cell swelling response, which characterizes brain damage in cerebral ischemia and traumatic brain injury.

Sodium azide (N a N 3) is a metabolic toxin used to induce "chemical hypoxia" by depleting intracellular ATP. See, Swanson, 1992. The morphological and electrophysiological responses of neural cells to NaN$^3$ are examined in a novel cell preparation. Freshly isolated native reactive astrocytes (NRAs) from adult rat brain are used and studied in a native state immediately after their isolation. Reactive astrocytes are astrocytes that have been activated or stimulated in vivo, such as those associated with brain or neural injury. In the post-mortem brains of traumatic brain injury (TBI) patients, reactive astrocytes are found in proximity to the injury. The majority of reactive astrocytes surrounding an injury site in the brain are reactive astrocytes. Type 1 reactive astrocytes comprise >80% of recoverable reactive astrocytes, whereas type 2 reactive astrocytes comprise about 5%. Reactive astrocytes are normally polarized under quiescent conditions.

As used herein, the term "neural cells" includes astrocytes. The term "reactive astrocytes" means astrocytes found in brain at the site of a lesion or ischemia. The term "native reactive astrocytes" or "WRAs" means reactive astrocytes that are freshly isolated from brain. The term "freshly isolated" as used herein refers to NRAs that have been purified from brain, particularly NRAs that were purified from about 0 to about 72 hours previously. When NRAs are referred to as being "purified from brain" the word "purified" means that the NRAs are isolated from other brain tissue and/or implanted gelatin or sponge and does not refer to a process that simply harvests a population of cells from brain without further isolation of the cells. As described herein, the $NC_{Ca\text{-}ATP}$ channel found in reactive astrocytes is present only in freshly isolated cells; the $NC_{Ca\text{-}ATP}$ channel is lost shortly after culturing the cells. NRAs provide an in vitro model that is more similar to reactive astrocytes as they exist in vivo in the brain, than astrocytes grown in culture. The terms "native" and "freshly isolated" are used synonymously. As used herein, the term "isolated neural cells" means neural cells isolated from brain.

Reactive astrocytes are produced in vivo and harvested from brain according to a method system similar to that described by Perillan. See, Perillan et al., 1999; Perillan et al., 2000. Harvested cells are then isolated and not cultured; rather, the freshly isolated reactive astrocytes are studied in a native state immediately after their isolation from the brain.

The Examples described herein reveal that NRAs from adult rat brain express a non-selective cation channel that is activated by depletion of [ATP]i at physiological concentrations of [Ca$^{2+}$]i. This $NC_{Ca\text{-}ATP}$ channel of the present invention, which is newly identified in NRAs and present in >90% of membrane patches from such cells, is distinguished from previously reported non-selective calcium and ATP channels by exhibiting significantly different properties. These distinguishing properties of the $NC_{Ca\text{-}ATP}$ of the present invention include: being activated by submicromolar [Ca] and exhibiting a different sensitivity to block by various adenine nucleotides. Opening of the $NC_{Ca\text{-}ATP}$ channel of the present invention by ATP depletion causes profound membrane depolarization, which precedes blebbing of the cell membrane. Upon ATP depletion, the $NC_{Ca\text{-}ATP}$ channel opens to allow Na$^+$ influx that leads to cell swelling. This channel is regulated by sulfonylurea receptor type 1 (SUR1). The channel can be blocked by sulfonylurea, such as glibenclamide and tolbutamide; treatment with glybenclamide results in significant reduction in swelling and blebbing induced by chemical ATP depletion. This channel participates in the cation flux involved in cell swelling. A method of the present invention includes the use of sulfonylurea compounds to inhibit the flow of current through the $NC_{Ca\text{-}ATP}$ channel and inhibit blebbing related to channel opening. Also, use of sulfonylurea compounds and other compounds that inhibit the flow of current through the $NC_{Ca\text{-}ATP}$ channel, thus can have a therapeutic preventative effect on cell swelling in brain.

Therefore, it is an object of the present invention to provide a composition comprising a membrane preparation expressing the $NC_{Ca\text{-}ATP}$ channel. For example, the membrane preparation is derived from neural cells, such as isolated native reactive astrocytes (NRAs), preferably freshly isolated native reactive astrocytes. The $NC_{Ca\text{-}ATP}$ channel in the composition has the following characteristics: (a) it is a 35 pS type channel; (b) it is stimulated by cytoplasmic Ca$^{2+}$; (c) it opens when cytoplasmic ATP is less than about 0.8 μM; and (d) it is permeable to the monovalent cations K$^+$, Cs$^+$, Li$^+$ and Na$^+$ and it can be blocked by antagonists of the type 1 sulfonylurea receptor.

Furthermore, it is an object of the present invention to provide a method of screening for antagonists of the $NC_{Ca\text{-}ATP}$ channel, comprising: (a) contacting a test compound with a composition comprising the $NC_{Ca\text{-}ATP}$ channel; and (b) identifying test compounds that inhibit an activity of said channel by measuring said activity in the presence and absence of said test compound, wherein a test compound that inhibits said activity is identified as an antagonist of the $NC_{Ca\text{-}ATP}$ channel. For example, the composition may contain a preparation of neural cells expressing the $NC_{Ca\text{-}ATP}$ channel or a membrane preparation expressing the $NC_{Ca-ATP}$ channel, such as a membrane preparation derived from isolated native reactive astrocytes (NRAs). The effect of the compound on this channel may include: (a) blocking the $NC_{Ca-ATP}$ channel; (b) closing the $NC_{Ca-ATP}$ channel; (c) preventing the $NC_{Ca-ATP}$ channel from opening; and (d) reducing the magnitude of membrane current through the $NC_{Ca-ATP}$ channel. It is also an object of the present invention to identify a compound that is an $NC_{Ca-ATP}$ antagonist, including an $NC_{Ca-ATP}$ channel inhibitor, an $NC_{Ca-ATP}$ channel blocker, a SUR1 antagonist, SUR1 inhibitor, and/or a compound capable of reducing the magnitude of membrane current though the channel.

It is a further object of the invention to provide a method for identifying compounds that inhibit neural cell swelling, comprising: (a) contacting a test compound with a composition comprising the $NC_{Ca-ATP}$ channel, and (b) determining whether the test compound blocks the $NC_{Ca-ATP}$ channel, wherein a test compound that blocks the $NC_{Ca-ATP}$ channel is identified as a compound for inhibiting neural cell swelling.

It is a further object of the present invention to provide a method for identifying compounds that inhibit brain swelling, comprising: (a) contacting a test compound with a composition comprising the $NC_{Ca-ATP}$ channel, and (b) determining whether the test compound blocks the $NC_{Ca-ATP}$ channel, wherein a test compound that blocks the $NC_{Ca-ATP}$ channel is identified as a compound for inhibiting brain swelling.

Yet another object of the present invention is to provide a method for identifying compounds that inhibit brain swelling, comprising: (a) contacting a test compound with a composition comprising the $NC_{Ca-ATP}$ channel, and (b) determining whether the test compound inhibits neural cell swelling, wherein a test compound that inhibits neural cell swelling is identified as a compound for inhibiting brain swelling.

A further object of the present invention provides a method for identifying compounds that inhibit neural cell swelling in an animal, comprising: (a) contacting a test compound with a composition comprising the $NC_{Ca-ATP}$ channel and determining whether the test compound blocks the channel, and (b) administering the test compound to an animal having a brain injury or cerebral ischemia, and determining whether the test compound that inhibits brain swelling of the treated animal, wherein test compounds that inhibit brain swelling are identified as compounds that inhibit neural cell swelling in an animal.

It is a further object of the present invention to provide a method for identifying compounds that inhibit brain swelling, comprising: (a) contacting a test compound with a composition comprising the $NC_{Ca-ATP}$ channel, and determining whether the test compound blocks the channel, and (b) administering the test compound to an animal having a brain injury or cerebral ischemia, and determining whether the test compound inhibits brain swelling of the treated animal, wherein test compounds that block the $NC_{Ca-ATP}$ channel are identified as compounds that inhibit brain swelling.

In each of these objects of the present invention, the composition preferably comprises a preparation of neural cells expressing the $NC_{Ca-ATP}$ channel or a membrane preparation expressing the $NC_{Ca-ATP}$ channel, which preferably is derived from isolated native reactive astrocytes (NRAs). It is a further object of the present invention to provide the above methods using a compound that is an antagonist of a type 1 sulfonylurea receptor, such as a sulfonylurea compound, a benzamido derivative or an imidazoline derivative.

It is a further object of the present invention to provide these methods in which the determining step include, but are not limited to, detecting or identifying swelling of the native reactive astrocytes, such as by microscopic observation of cell appearance (normal, blebbing, swelling); measuring channel currents; measuring membrane potential; detecting expression of annexin V; detecting expression of propidium iodide; in vitro binding assays; and combinations thereof.

It is a further object of the present invention to provide a method of preventing neural cell swelling in the brain of a subject, said method comprising administering to the subject a formulation containing an effective amount of a compound that blocks the $NC_{Ca-ATP}$ channel and a pharmaceutically acceptable carrier.

It is a further object of the present invention to provide a method of alleviating the negative effects of traumatic brain injury or cerebral ischemia stemming from neural cell swelling in a subject, comprising administering to the subject a formulation comprising an effective amount of a compound that blocks the $NC_{Ca-ATP}$ channel and a pharmaceutically acceptable carrier. Such administration may be delivery directly to the brain, intravenous, subcutaneous, intramuscular, intracutaneous, intragastric and oral administration. Examples of such compounds include antagonist of a type 1 sulfonylurea receptor, such as sulfonylureas like glibenclamide and tolbutamide, as well as other insulin secretagogues such as repaglinide, nateglinide, meglitinide, midaglizole, LY397364, LY389382, gliclazide, glimepiride, MgADP, and combinations thereof.

It is yet another object of the present invention to provide a formulation for preventing or inhibiting neural cell swelling in the brain of a subject, using a formulation that includes a compound that blocks the $NC_{Ca-ATP}$ channel and a pharmaceutically acceptable carrier, wherein the quantity of said compound is at least 10 times greater than the quantity of said compound in formulations for treating diabetes.

EXAMPLES

The following examples are provided for further illustration of the present invention, and do not limit the invention. The examples provided herein are for illustrative purposes only, and are in no way intended to limit the scope of the present invention. While the invention has been described in detail, and with reference to specific embodiments thereof, it will be apparent to one with ordinary skill in the art that various changes and modifications can be made therein without departing from the spirit and scope thereof. Experiments and exemplary procedures are described below which provide additional enabling support for the present invention. In particular, in vitro studies using freshly isolated reactive astrocytes and in vivo studies using appropriate animal models are disclosed.

General Methods

Cell Preparation

Reactive astrocytes are produced in vivo and harvested from adult brain in the following manner: gelatin sponges (Gelfoam®, Upjohn Co., Kalamazoo Mich.) are implanted into a stab wound in the parietal lobe of 8 week old Wistar rats as described herein. Sponge pieces are harvested at 8 days and washed three times in phosphate-buffered saline (PBS, pH 7.4) to remove adherent tissue. Depending on the number of NRAs required for a particular study, the sponge pieces may be harvested earlier or later after implantation into a stab wound, with the preferred harvest being conducted from about 2 days to about 30 days after implantation, and the most preferred range being conducted from about 2 days to about 3 days after implantation.

NRAs are freshly isolated from the sponge pieces in the following manner: washed pieces are placed in an Eppendorf tube containing artificial cerebrospinal fluid (aCSF) composed of (mM): 124 mM NaCl, 5.0 mM, 1.3 mM $MgCl_2$, 2.0 mM $CaCl_2$, 26 mM $NaHCO_3$, and 10 mM D-glucose; at pH 7.4, ≈290 mOsm, wherein the aCSF contains papain 20 U/ml, trypsin inhibitor 10 mg/ml and DNase 0.01% (Worthington, Lakewood, N.J.), the entirety of which is referred to as a "digestion system."

This digestion system is transferred to an incubator (humidified 90%/10% air/C02, 37° C.) for 20 minutes, and is gently triturated every 5 minutes. The cell suspension is centrifuged at 3,000 rpm for 1 minute. The pelleted cells are resuspended in aCSF and stored at 4° C. until studied.

For some studies, prior to resuspension in aCSF, the pelleted cells can be further purified by removing red blood cells (RBCs) using density gradient centrifugation in Histopaque-1 077 (Sigma Diagnostics, St. Louis, Mo.). This further purification process can produce a population of cells in which <<1% are RBCs, as determined by phase contrast microscopy.

Scanning Electron Microscopy (SEM)

To study cell blebbing and swelling, freshly isolated cells are exposed at room temperature to $NaN^3$ then, after various time intervals, cells are fixed using iced 4% formaldehyde+ 1% glutaraldehyde for 24 hours then dehydrated using serial concentrations (35, 50, 75, 95, 100%) of ethanol. Specimens are critical point dried (Tousimis), gold coated (Technics), and viewed using an AMR 1000 scanning electron microscope.

Electrophysiology

Experiments are carried out at room temperature, 22-25° C., using NRAs within 24 hour of cell isolation. An aliquot of these freshly isolated NRAs is placed in the recording chamber filled with extracellular bath solution containing (a): NaCl 130, KCl 10, $CaCl_2$ 1, $MgCl_2$ 1, HEPES 32.5, glucose 12.5, pH 7.4. After viable cells adhere to the surface, flushing with excess solution washes away residual debris not previously removed by centrifugation. Membrane currents are amplified (Axopatch 200A, Axon Instruments, Foster City, Calif.) and sampled on-line at 5 kHz using a microcomputer equipped with a digitizing board (Digidata 1200A, Axon Instruments) and running Clampex software (version 8.0, Axon Instruments). Membrane currents are recorded in intact cells using both the cell-attached and the nystatin-perforated whole-cell configurations, according to methods described in Horn and Marty, 1988. Membrane currents are recorded in cell-free isolated membrane patches, using both the inside-out and outside-out configurations, such as those described in Hamill et al., 1981. Patch clamp pipettes, pulled from borosilicate glass (Kimax, Fisher Scientific, Pittsburgh, Pa.), have resistances of 6-8 MΩ a for single channel recordings and 2-4 MΩ a for experiments using the nystatin-perforated whole-cell technique. The bath electrode is a Ag/AgCl pellet (Clark Electromedical, Reading, England) that is placed directly in the bath except when the bath [Cl—] is altered, in which case an agar bridge made with 3 M KCl is used to connect to the bath.

The terms "intracellular" and "cytoplasmic" are interchangeable, as are the terms "extracellular" and "external". The terms "voltage" and "potential" are interchangeable when referring to membrane voltage or membrane potential. "Clamping" a cell membrane refers to holding the voltage across the cell membrane constant and measuring changes in membrane current as membrane resistance changes due to ion channel opening and closing ("voltage clamp") or holding the current across the cell membrane constant and measuring changes in membrane voltage as membrane resistance changes due to ion channel opening and closing ("current clamp"). When a membrane voltage is imposed on the cell, for example with a "ramp" or "pulse", it is understood that the cell membrane has been voltage-clamped and membrane current is being measured. When membrane "resting potential" is measured, it is understood that the cell membrane has been current-clamped and membrane voltage is being measured.

The "whole-cell" experimental configuration refers to a situation in which a recording pipette penetrates the cell membrane so that the pipette solution is continuous with the cytoplasm or the membrane under the pipette is perforated using nystatin, the external solution is in contact with the extracellular membrane, and current or voltage recordings represent measurements from the entire cell membrane. The "cell-attached patch" experimental configuration refers to a situation in which the pipette contacts the cell so that the patch is still forming part of the intact cell membrane and channels in the patch are recorded. The "outside-out patch" experimental configuration refers to a situation in which an excised patch of cell membrane is sealed to the tip of a recording pipette so that the pipette solution is in contact with the extracellular side of the membrane, the external solution is in contact with the cytoplasmic side of the membrane, and current or voltage recordings represent measurements from the excised patch of membrane. The "inside-out patch" experimental configuration refers to a situation in which an excised patch of cell membrane is sealed to the tip of a recording pipette so that the pipette solution is in contact with the cytoplasmic side of the membrane, the external solution is in contact with the extracellular side of the membrane, and current or voltage recordings represent measurements from the excised patch of membrane.

The term "patches" includes, but is not limited to: inside-out patches, outside-out patches, an excised patch of a cell membrane, or a cell-attached patch. The term "membrane preparation" includes patches as well as cell membranes isolated from mammalian cells or tissues. Isolated mammalian cell membranes are produced by methods well known in the art. One example of such a membrane preparation is a microsomal fraction purified from disrupted cells or a tissue sample by discontinuous sucrose gradient centrifugation.

Patches with seal resistance of <3 GΩ and access resistance of >50 MΩ are discarded. Macroscopic membrane currents are measured during step pulses (600 ms) or during ramp pulses (−140 to +50 mV at 0.32 mV/ms) from a holding potential of −67 mV.

Recording Solutions

For whole cell macroscopic recordings, a nystatin perforated patch technique is used, with a bath solution containing (mM): NaCl 130, KCl 10, $CaCl_2$ 1, $MgCl_2$ 1, HEPES 32.5, glucose 12.5, pH 7.4. The pipette solution contains (mM): KCl 55, $K_2SO4$ 75, $MgCl_2$ 8, and HEPES 10, pH 7.2. Nystatin, 50 mg (Calbiochem) is dissolved in dimethylsulfoxide (DMSO), 1 ml. Working solutions are made before the experiment by adding 16.5 µl nystatin stock solution to 5 ml of the base pipette solution to yield a final concentration of nystatin of 165 µg/ml and DMSO 3.3 µl/ml. This composition of the pipette solution includes $K_2SO_4$ instead of a portion of the KCl that would otherwise be included. The $SO_4^{2-}$ anion, unlike Cl—, is not permeable through the nystatin pore. Reducing the pipette [Cl-] reduces the driving force for Cl— into the cell, thereby minimizing osmotic swelling of the cell that might otherwise occur during electrophysiological recording (Horn and Marty, 1988).

For cell-attached patch recording, a bath solution is used containing (mM): NaCl 130, KCl 10, CaCl$_2$ 1, MgCl$_2$ 1, HEPES 32.5, glucose 12.5, pH 7.4. The pipette contains (mM): KCl 145, MgCl$_2$ 1, CaCl$_2$ 0.2, EGTA 5, HEPES 10, pH 7.28. The measured osmolarity of the extracellular solution is ≈300 mOsm (Precision Systems, Natick, Mass.).

For most inside-out patch recording, a bath solution is used containing (mM): CsCl 145, CaCl$_2$ 4.5, MgCl$_2$ 1, EGTA 5, HEPES 32.5, glucose 12.5, pH 7.4. The pipette contains (a): CsCl 145, MgCl$_2$ 1, CaCl$_2$ 0.2, EGTA 5, HEPES 10, pH 7.28. For other inside-out patch recordings, Cs+ in the above solutions is replaced with equimolar K+.

For the inorganic cation substitution experiments, Cs+ in the pipette is replaced by equimolar concentrations of individual test ions, except when using Ca$^{2+}$ or Mg$^{2+}$, in which cases a concentration of 75 mh4 is used to facilitate seal formation (Cook et al., 1990).

For outside-out patch recording, the pipette solution contains (mM): CsCl 145, MgCl$_2$ 1, CaCl$_2$ 0.2, EGTA 5, HEPES 10, pH 7.28. The standard bath solution contains (mM): CsCl 145, CaCl24.5, MgCl$_2$ 1, EGTA 5, HEPES 32.5, glucose 12.5, pH 7.4. For the organic cation substitution experiments, Cs+ in the bath is replaced with equimolar concentrations of test cation.

For experiments requiring low concentration of free Ca$^{2+}$ in bath solution, Ca$^{2+}$-EGTA buffered solution is employed, and free [Ca$^+$] is calculated using the program WEBMAXC v2.10 (see the Stanford University website). For [Ca$^{2+}$]=1 µM, 5 mM EGTA is used and 4.5 mM Ca$^{2+}$ salt. [Ca$^{2+}$]=1 µM is also used in solutions to test intracellular ATP and Mg$^{2+}$ activities.

Single-channel amplitudes used to calculate slope conductance are obtained by fitting a Gaussian function to an all-points amplitude histogram of records obtained at various potentials. To calculate open channel probability (n·Po) at various potentials and with different test agents, the all-points histogram is fit to a Gaussian function and the area under the fitted curve for the open channel is divided by the area under the fitted curve for the closed plus open channel. Values of n·Po at different concentration of test agents are fit to a standard logistic equation using a least-squares method.

For estimating ionic permeabilities of various cations relative to that for K+, each permeability (Px/PK) is obtained from its reversal potential (Erev) by fitting to the Goldman-Hodgkin-Katz (GHK) equation well known in the art. See Goldman 1943; Hodgkin and Katz, 1949. Current-voltage data are fit to the GHK equation, assuming that both K+ and the test ion are permeant.

To estimate the pore size of the NC$_{Ca\text{-}ATP}$ channel of the present invention, the relative permeabilities of organic cations are evaluated. The Stokes-Einstein radius (rse) is calculated from the limiting conductivities (*) of the ions with the formula: $r_{SE} \cdot \lambda =$ constant. The constant is determined from the behavior of TEA at 25° C., for which λ=44.9 cm$^2$Ω-1, $r_{SE}$=0.204 nm. The Stoke-Einstein radius is then converted to the molecular radius using correction factors read off from FIG. 6.1 in Robinson and Stokes, 1970. The equivalent limiting conductance for ethanolamine is given (ibid.) and those of other ions are calculated from their molecular weight by the formula, MW 0.5·λ=constant. The constant is determined by the value for ethanolamine at 25° C.: MW=62.1 and λ=4.42 cm$^{2\Omega-1}$ equiv. Relative permeabilities (Px/PCs) are then plotted against the calculated ionic radii. The effect of solute size on the rate of penetration (permeability) through pores is expressed by the Renkin equation (Renkin, 1955):

$$a/a_0 = [1-(r/R)]^2 [1-2.104(r/R)+2.09(rR)^3-0.95(r/R)^5] \quad (1)$$

in which a, a$_0$, r, and R are the effective area of the pore, the total cross sectional area of the pore, radius of the solute, and radius of the pore, respectively.

Junction potentials are determined with an electrometer by measuring the diffusion potential established across a dialysis membrane and are subtracted when appropriate. Holding currents are not subtracted from any of the recordings. Difference currents are obtained by simply subtracting current records before and after perfusing NaN$_3$, with no other processing being employed.

Results

The Role of the NC$_{Ca\text{-}ATP}$ Channel in Neural Cell Swelling

Characterization of the Channel

Example 1

Morohological Changes with ATP Depletion Using NaN$_3$

Cultured neural cells have been shown to swell upon ATP depletion. See, Jurkowitz-Alexander et al., 1992; Jurkowitz-Alexander et al., 1993. Freshly isolated NRAs depleted of ATP also results in cell swelling. Ischemia or traumatic injury in brain also causes depletion of ATP in brain neural cells.

The surfaces of freshly isolated NRAs are highly complex, exhibiting small membrane evaginations and fine processes that decorate the entire cell surface, as shown in the scanning electron micrograph in FIG. 14A. Exposure of NRAs to NaN$_3$ (1 mM) causes changes in the surface appearance, characterized early-on by loss of complex structure and development of surface blebs (FIG. 14B), followed later by a grossly swollen appearance with complete loss of fine structure and formation of multiple large blebs (FIG. 14C). Therefore, NRAs undergo blebbing and swelling after NaN3-induced ATP depletion.

Phase contrast microscopy is also useful for assessing this process, although fine structure cannot be resolved. Blebbing is visibly apparent 10-15 minutes after exposure to NaN$_3$. Morphological changes of this sort are attributable to loss of cytoskeletal integrity, combined with action of an osmotic force that causes swelling of the cell.

To assess the contribution of the osmotic gradient to cell swelling, the experiment is repeated in the presence of mannitol, an impermeant oncotic agent. Mannitol (50 mM), at a concentration sufficient to increase osmolarity of the extracellular solution from 300 to 350 mOsm, delays bleb formation >30 minutes after exposure to NaN$_3$. Cellular ATP also can be depleted using exposure to NaCN (2.5 mM) plus 2-deoxyglucose (10 mM). See, Johnson et al., 1994. Similar morphologic changes, including cell membrane blebbing and delay of blebbing by mannitol are obtained following exposure to NaCN and 2-deoxyglucose. This demonstrates that the effect of NaN$_3$ is due in fact to ATP depletion and not to any other non-specific effect of NaN$_3$.

Example 2

General Electrophysiological Properties of NRAs

The macroscopic currents of whole cell preparations of N u s are characterized by small inward currents at negative potentials, large outward currents at positive potentials, and a flat "plateau" region at intermediate potentials. NRAs exhibit macroscopic currents that are consistent with observations in primary cultured cells of the same origin. See, Perillan et al., 1999; Perillan et al., 2000. The NRAs exhibited inward currents negative to the K$^+$ equilibrium potential ($E_K$) are usually <100 pA, much smaller than values reported in cultured neonatal astrocytes (Ransom and Sontheimer, 1995), but consistent with findings in astrocytes freshly isolated from injured brain (Bordey and Sontheimer, 1998; Schroder et al., 1999). The large outward currents in NRAs are partially blocked by charybdotoxin (100 nM), iberiotoxin (1 00 nM) and tetraethylammonium chloride (5 mM), consistent with the presence of a large conductance Ca2$^+$-activated K$^+$ channel. See, Perillan et al., 1999. The outward current that remains in the presence of charybdotoxin can be further blocked by 4-aminopyridine (5 mM), and exhibits kinetic properties typical of a delayed rectifier K$^+$ channel. Consistent with a previous report (Perillan et al., 1999), fast inward voltage dependent currents attributable to Na$^+$ channels are observed in less that 1% of NRAS.

NaN$_3$ Elicits Depolarizing Inward Current Due to 35 DS Channel

Current clamp recordings are used to investigate the effect of ATP depletion by NaN$_3$ in NRAs. For these experiments, a nystatin-perforated patch method is used to assure that the metabolic disruption comes from drug application and not cell dialysis. Extracellular application of NaN$_3$ (1 mM; room temperature) results in a large and swift depolarization of the cells (FIG. 1A). NaN3 rapidly depolarizes the cells to $E_m \approx 0$ mV (−4.3±0.9 mv). Depolarization usually starts −1 minute after addition of NaN$_3$, is complete in <3 minutes, and is irreversible on washout of drug. Ouabain is a known Na$^+$/K$^+$-ATPase blocker. See, Brismar and Collins, 1993. The magnitude of the depolarization observed with NaN$_3$ far exceeds the small reversible depolarization induced by ouabain (1 mM). This indicates that the large depolarization observed after exposure to NaN$_3$ is not caused by Na+/K+-ATPase pump failure.

The time course of depolarization with NaN3 is appreciably more rapid than the time course for development of cell membrane blebbing observed with the same treatment. Also, neither the time course nor the magnitude of the depolarization is affected by raising the extracellular osmolarity with 50 mM mannitol, a treatment that substantially delays bleb formation. Thus, depolarization is a primary event, not secondary to cell swelling or stretch.

Voltage-clamp recordings show that exposure to NaN$_3$ results in a net increase of inward current in NRAs. Recordings obtained using both ramp (FIG. 1B) and step pulses (FIG. 1C) show significantly larger currents after NaN$_3$ treatment, as shown by comparing the recordings before (a) and after (b) NaN$_3$ treatment. A plot of the "difference currents", obtained by subtracting the current-voltage curve before drug from that after drug (line c in FIG. 1B), indicates that the new current turned on by NaN$_3$ reverses near 0 mV. A reversal potential near 0 mV is indicative that the NaN$_3$-induced current results from a non-specific cation conductance.

To further characterize the NaN$_3$-induced current, cell-attached patch recordings are used. Exposure to NaN$_3$ elicits single channel currents in patches that exhibit no single channel currents prior to addition of drug (FIG. 1D). After addition of NaN$_3$, recordings at low temporal resolution reveal a large increase in current variance that, after increasing temporal resolution, is revealed to be due to single channel events (FIG. 1E at 3 and 4). The amplitudes of single-channel events recorded at different membrane potentials are plotted in FIG. 1F, which shows that NaN$_3$ activates a single channel conductance of ≈35 pS that exhibits weak inward rectification when measured in the cell-attached configuration.

Additional experiments are carried out in the cell-attached configuration with the pipette solution supplemented with various drugs. The NaN$_3$-induced single channel currents are not blocked by 10 mM TEA, 5 mM 4-AP, 100 nM iberiotoxin, 100 nM charybdotoxin, or 1 µM tetrodotoxin (4-6 patches for each compound). These experiments indicating that a typical K$^+$ or Na$^+$ channel is not involved. Also, because 0.2 mM Ca2$^+$ is included in the pipette solution, these single channel openings are unlikely to be due to monovalent cation influx via an L-type Ca$^{2+}$ channel.

Similar depolarization and activation of a 35 pS channel are obtained when cellular ATP is depleted using exposure to NaCN (2.5 mM) plus 2-deoxyglucose (10 mM). This demonstrates that the effect of NaN$_3$ is caused by ATP depletion and not by any other non-specific effect of NaN$_3$.

Apart from ATP depletion, patch excision is also a highly reliable method for channel activation. Of the more than 120 cells studied in the cell-attached configuration, spontaneous channel activity attributable to a ≈35 pS conductance is detected in only 2 cells. Thus, the NC$_{Ca-ATP}$ channel of the present invention is typically silent in metabolically healthy cells. By contrast, a ≈35-pS channel is present in >90% of inside-out patches formed from NRAs not exposed to NaN$_3$ or other metabolic toxins, thus demonstrating that an intracellular element lost on patch excision normally prevents channel activation.

Another potential mechanism of channel activation other than patch excision is regulatory volume decrease (RVD). Cell swelling is widely recognized as a stimulus that initiates RVD, a phenomenon accompanied by activation of various currents, including a non-selective cation channel in some systems. See, Ono et al., 1994. When membrane patches are studied in a cell-attached configuration, hyposmotic stimulation (210 mosmo/kgH$_2$O) activated single channel events, but none exhibit a ≈35 pS conductance. This finding indicates that the depolarization and channel activation observed with NaN$^3$ are not part of an RVD response secondary to NaN$_3$-induced cell swelling, and accords with the previously noted observation that NaN$_3$-induced depolarization preceded cell swelling. This fact is supported by the observation that the NC$_{Ca-ATP}$ channel is seldom observed in cell attached patches from healthy cells, but becomes evident in >90% of patches after conversion to an inside-out configuration. Also, the NC$_{Ca-ATP}$ channel is lost shortly after culturing reactive astrocytes.

Example 3

Relative Permeabilities and Pore-size

Figure 2A:
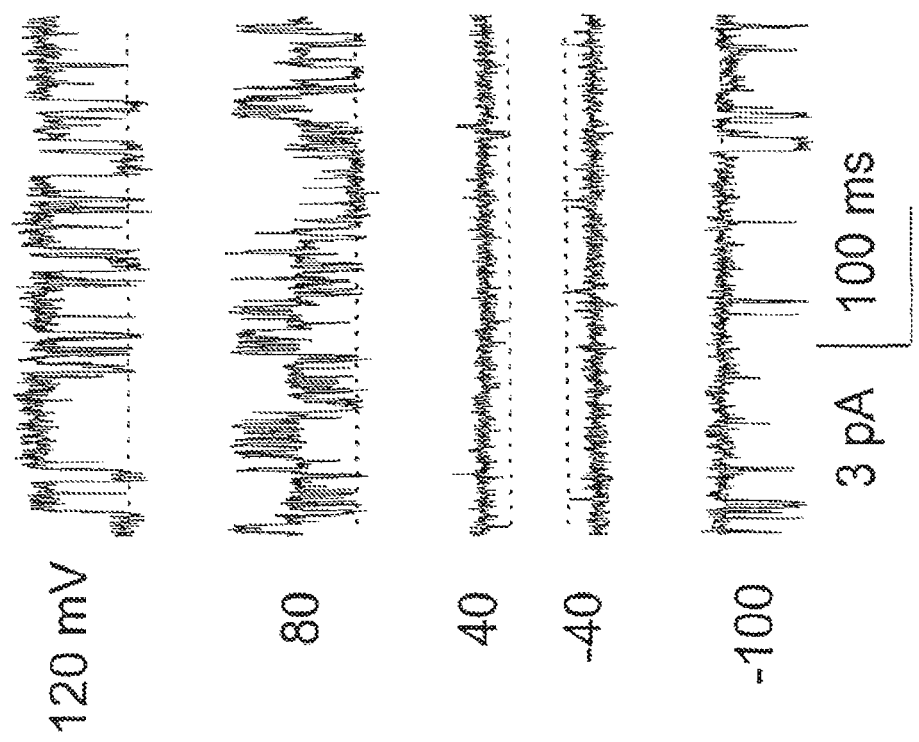
FIG. 2A shows single channel currents recorded in an inside-out patch at different membrane potentials; dotted line indicates channel closing.

The channel is further characterized using membrane patches in the inside-out configuration. Records obtained during test pulses to various potentials with equal [K$^+$] on both sides of the membrane are shown in FIG. 2A. Amplitude histograms are constructed of events observed at potentials from −140 mV to +100 mV, and values (mean±SE) for 4 patches are plotted and show in FIG. 2B. Fit of the data to a linear equation indicates a slope conductance of 35 pS, with an extrapolated reversal potential ($E_{rev}$) of +0.1 mV, close to the expected K$^+$ reversal potential ($E_K$) of 0 mV.

In addition to conducting K$^+$, the channel transports a variety of alkaline ions (FIG. 3A), indicating that it is a non-selective cation channel. In inside-out patches, the conductance of the channel is measured with various alkaline ions in the pipette solution, including $Cs^+$, $Na^+$, $Rb^+$, $K^+$, and $Li^+$, always with equimolar $K^+$ in the bath solution. Current-voltage data are fit to the GHK equation. $Na^+$ is shown to have a nearly equal slope conductance (32.6 pS) compared to $K^+$ (35.2 pS), but the slope conductance is reduced with other cations (FIG. 3B). Measurements of $E_{rev}$ are used to estimate relative permeabilities for the series of alkaline ions. Values for relative permeabilities derived from the GHK equation are $P_{Cs}^+/P_K^+=1.06$, $P_{Na}^+/P_K^+=1.04$, $P_{Rb}^+/P_K^+=1.02$, and $P_{Li}^+/PK^+=0.96$, indicating that this channel is nearly equally permeable to all monovalent cations.

The permeability of the $NC_{Ca-ATP}$ channel of the present invention to anions, such as $Cl^-$, is also assessed. After measuring single channel current amplitudes at different potentials with 145 mM KCl, the bath solution is changed to equimolar $K^+$ gluconate. When an agar bridge is used, the solution change resulted in a change in Erev<0.5 mV, indicating that the $NC_{Ca-ATP}$ channel of the present invention is essentially impermeable to anions.

The permeability of the instant channel to divalent cations, $Ca^{2+}$ and $Mg^{2+}$, is also investigated (FIG. 3C). When potassium ion in the pipette solution is replaced with 75 mM $Ca^{2+}$ or $Mg^{2+}$, inward currents are not detected. Fit to the GHK equation gives best fit values for $E_{rev}$,<<-65 mV for $Ca^{2+}$ and $Mg^{2+}$ respectively, giving relative permeabilities with respect to $K^+$ of <<0.001, indicating that this channel is essentially impermeable to divalent cations.

Because the $NC_{Ca-ATP}$ P channel of the present invention discriminates very poorly among monovalent inorganic cations (FIGS. 3A and B), experiments are performed to determine the equivalent pore size of the channel by measuring channel permeability, relative to $Cs^+$, for a wide range of organic cations. Using an outside-out patch configuration, single-channel current-voltage relations are plotted to obtain $E_{rev}$ for a number of organic cations. Permeability ratios are then derived from fits to the GHK equation. For each of the organic cations (a) nethanolamine, (b) guanidium, (c) ethanolamine, (d) diethylamine, (e) piperazine, (f) Tris, and (g) N-methylglucamine, the mean value of relative permeability measured is plotted against its hydrated molecular radius (FIG. 3D, empty circles). The permeability ratios define a smoothly declining series of values that are well fit by the Renkin equation. The Renkin equation describes the permeation of a rigid sphere through a cylindrical pore. Renkin, 1955. Least-squares, fit to the equation, indicates an equivalent pore radius of 0.67 nm for the $NC_{Ca-ATP}$ channel of the present invention. A 0.67 nm pore radius is similar to pore sizes of 6 A, found for the $Ca^{2+}$ channel (McCleskey and Almers, 1985) and 7.4 A, found for the nAChR channel (Adams et al., 1980). Junction potentials determined according to the methods described herein generally did not exceed 5 mV.

Example 4

Inhibition by $[ATP]_i$

The $NC_{Ca-ATP}$ channel is inhibited by intracellular ATP, based on the finding that this channel is turned on after depleting intracellular ATP by exposure to $NaN_3$ (See FIGS. 1B, 1C, 1D and 1E) or to NaCN plus 2-deoxyglucose. This fact is supported by the observation that the $NC_{Ca-ATP}$ channel of the present invention is seldom observed in cell attached patches from healthy cells, but becomes evident in >90% of patches after conversion to an inside-out configuration.

Figure 4A:
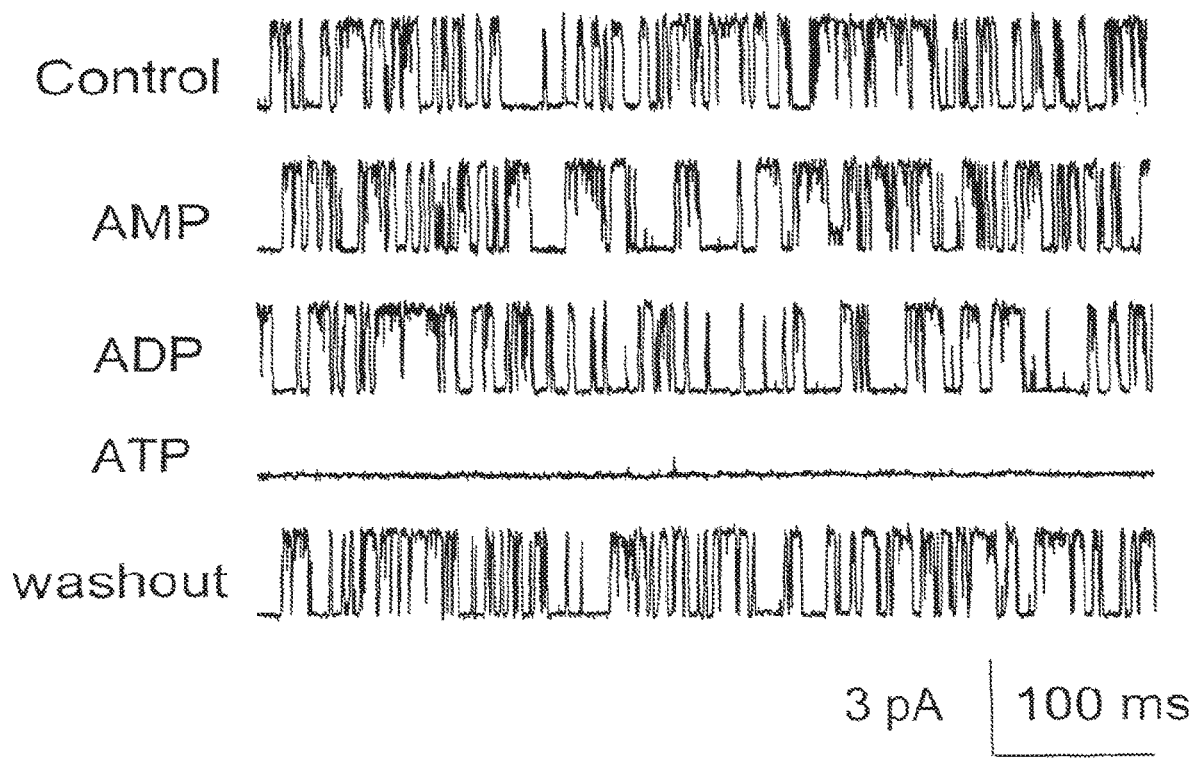
FIG. 4A shows single channel recordings in an inside-out patch in the absence and presence of cytoplasmic ATP.
Figure 4B:
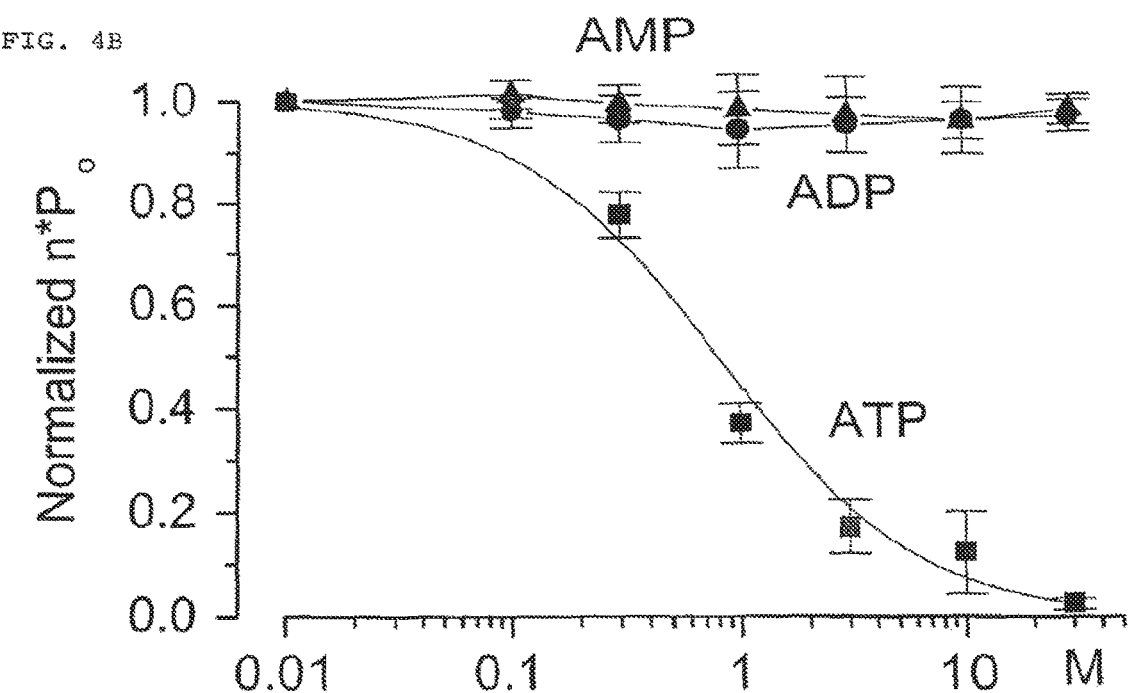
FIG. 4B is a plot of normalized open channel probability (n·Po) vs. concentration of cytoplasmic ATP.

Inside-out patches are used to demonstrate that the channel is sensitive to block by ATP on the cytoplasmic side of the membrane. Patches are studied using Cs' as the charge carrier, to assure that no $K^+$ channel, such as Kir2.3 or $K_{ATP}$, is contributing to patch activity. With no ATP and 1 μM $Ca^{2+}$ in the bath, the $NC_{Ca-ATP}$ channel exhibits vigorous openings. 1 mM ATP causes profound diminution in channel activity, an effect that is readily reversed on washout (FIG. 4A); however, channel availability is unaffected by 1 mM AMP or ADP. The open channel probability (n·Po) is measured at different [ATPIi, and these values are normalized to that obtained at $[ATP]_i=0$ mM, and fitted to a standard logistic equation. As shown in FIG. 4B, the $NC_{Ca-ATP}$ channel is blocked by $[ATP]_i$ in a dose-dependent manner. Half maximum inhibition ($IC_{50}$) is observed at $[ATP]_i, =0.79$ μM with a Hill coefficient of 1, and channel activity is completely abolished at [ATP]i>30 μM. ADP and AMP, have no effect on the $NC_{Ca-ATP}$ channel activity in inside-out patches.

This in vitro assay for determining the concentration of the test compound which achieves a half-maximal inhibition of channel activity (ICSO) may be used to formulate dose in animal models to achieve a circulating plasma concentration range that includes the $IC_{50}$.

Example 5

Activation by $[Ca^{2+}]_i$

Figure 5A:
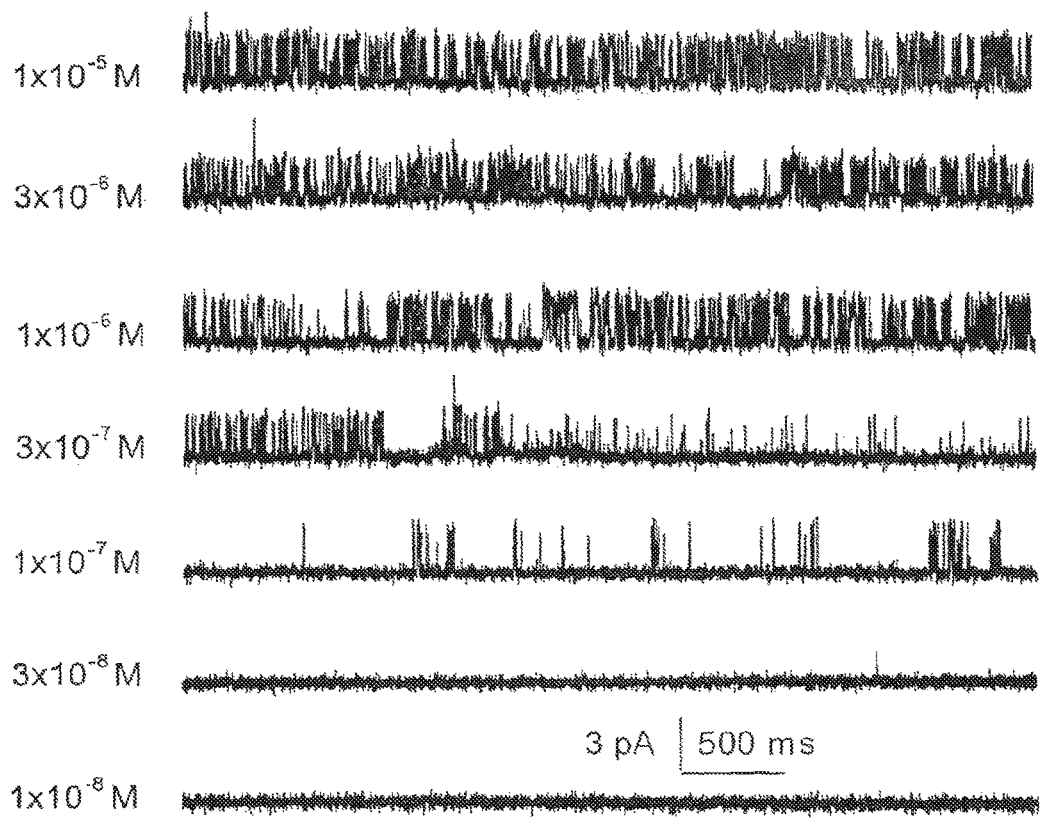
FIG. 5A shows current records from an inside-out patch exposed to different concentrations of $[Ca2^+]_i$.
Figure 5B:
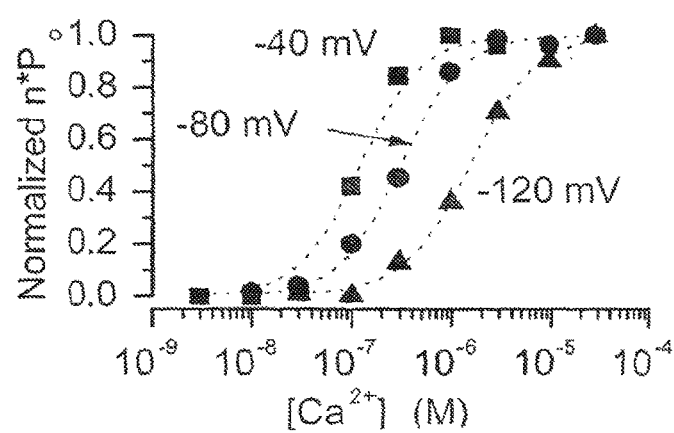
FIG. 5B the values of n·Po measured at the membrane potentials and $[Ca2+]_i$ indicated.

The $Ca^{2+}$ concentration on the cytoplasmic side of the membrane is also found to regulate activity of the $NC_{Ca-ATP}$ channel of the present invention. The relationship between $NC_{Ca-ATP}$ channel activity and $[Ca^{2+}]i$ is examined using inside-out patches studied at membrane potential (Em)=-80 mV. Changing $[Ca^{2+}]i$ clearly affects activity of the $NC_{Ca-ATP}$ channel (FIG. 5A). When free $[Ca^{2+}]i$ is <30 nM, no channel activity is apparent. With $[Ca^{2+}]i>30$ nM, the open probability (no·o) increases in accordance with the $[Ca^{2+}]i$, up to ≈1 μM of $[Ca^{2+}]i$ at which activity is near maximum. The effect of $Ca^{2+}$ on channel availability is found to depend on membrane voltage. Values of no·o from 4-9 patches obtained at three different potentials, Em=-40 mV, -80 mV and -120 mV, are normalized to values observed with 3 μM $[Ca^{2+}]i$. These data are fit to a standard logistic equation using a Hill coefficient of 1.5 and half-maximum values of 0.12 μM, 0.31 μM and 1.5 μM at -40 mV, -80 mV and -120 mV, respectively (FIG. 5B). These data indicate that channel activity is strongly dependent on $[Ca^{2+}]i$ at physiologically relevant concentrations, and that the effect of $Ca^{2+}$ is voltage dependent, consistent with a $Ca^{2+}$ binding site inside the electric field of the membrane.

Example 6

Internal $Mg^{2+}$ Causes Rectification

Figure 6:
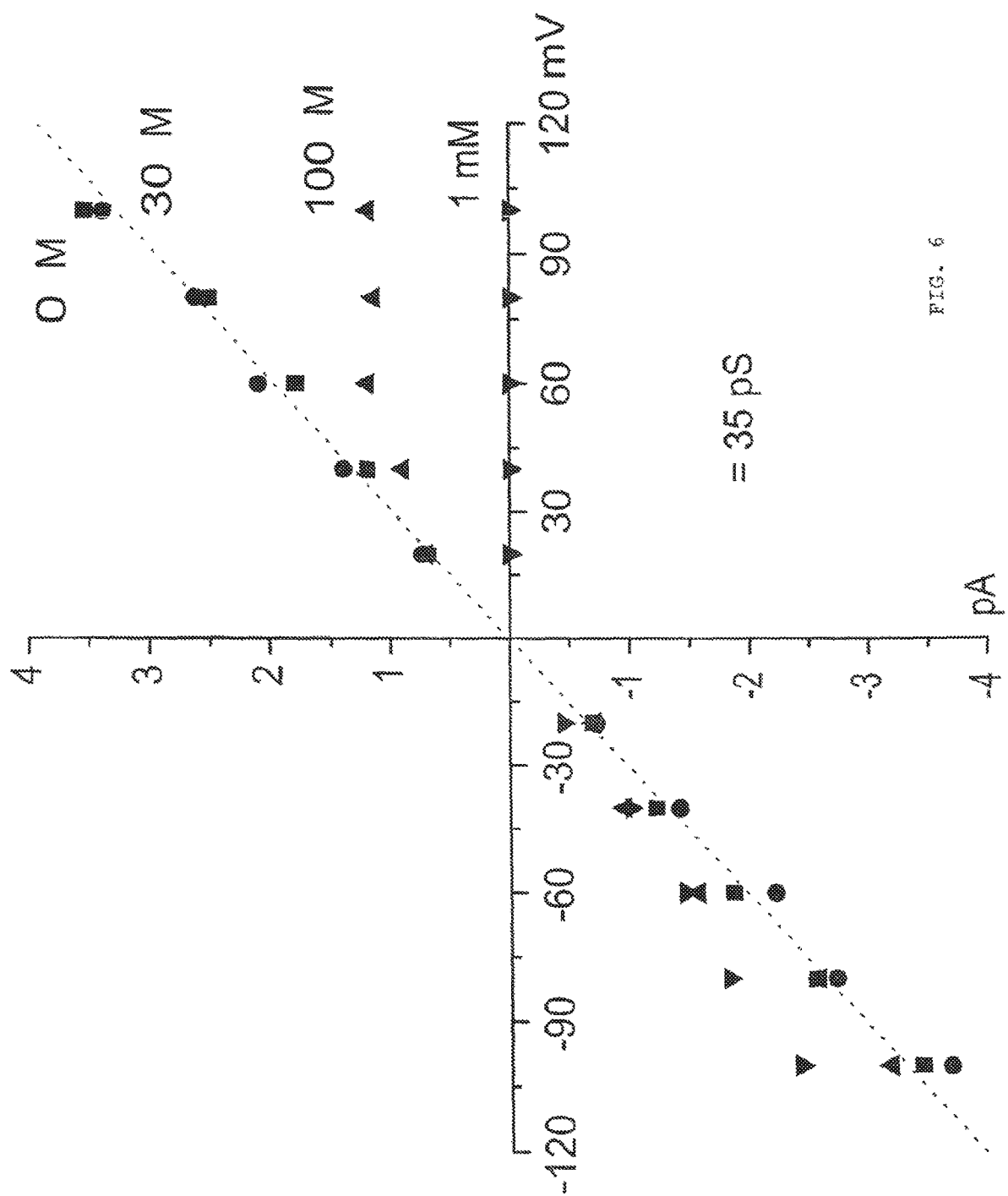
FIG. 6 is a plot of mean single channel amplitudes obtained in an inside-out patch configuration at different potentials studied and with different $[Mg^{2+}]_i$; the dotted line indicates 35 pS conductance.

Because certain channels are sensitive to intracellular $Mg^{2+}$ (Chuang et al., 1997; Perillan et al., 2000), experiments are carried out to determine whether the channel rectification observed in cell-attached patch recordings (see FIG. 1F) might be due to intracellular $Mg^{2+}$. Using inside-out patches studied with equimolar $K^+$ on both sides of the membrane, $[Mg^{2+}]$ is varied on the cytoplasmic side. Single channel records and channel amplitudes observed with different $[Mg^{2+}]i$ are shown (FIG. 6). No rectification is evident with $[Mg^{2+}]i$ 30 μM, but at $[Mg^{2+}]i \approx 100$ μM, increasingly strong rectification is present. At 100 μM, $Mg^{2+}$ appears to produce a flickery block.

Example 7

Identifying the Presence of SUR in NRAs

Figure 7A:
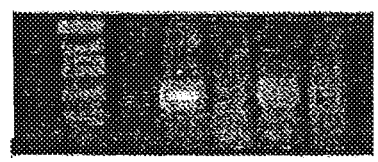
FIG. 7 (comprised of FIGS. 7A and 7B) shows that presence of SUR1 mRNA and absences of Kir6.1 and Kir 6.2 in reactive astrocytes. Lanes 3 and 5 in FIG. 7A show the presence of SUR1 in insulinoma RIN-m5f cells and NRAs, respectively. Lanes 4 and 6 in FIG. 7A show that SUFU is absent in both cell types. Lanes 3 and 4 in FIG. 7B show that Kir6.1 is present in insulinoma RIN-m5f cells and Kir6.2 is absent from the insulinoma cells, respectively. Lanes 5 and 6 in FIG. 7B show that neither Kir6.1 nor Kir6.2 is present in NRAs, respectively.
Figure 7B:
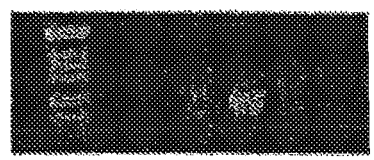

To determine if SUR receptors are present in NRAs, the binding of glibenclamide to these cells is assessed by fluorescence microscopy. Eight week old Wistar rats are injured by a stab wound into the subcortical white matter and implantation of a gelatin sponge as previously described herein. Eight days later, tissue sections of formaldehyde-fixed brains from injured animals are incubated for 60 minutes at room temperature with 20 nM FITC-conjugated glibenclamide. A fluorescence image of the gelatin sponge shows labeled cells lining the cavities of the sponge. In brain adjacent to the injury, essentially no glibenclamide binding is apparent. These data indicate that SUR, which are not normally present in subcortical white matter, are expressed in neural cells following traumatic injury.
RT-PCR Total RNA is extracted from cells and used to synthesize cDNA, which is amplified from reactive astrocytes is analyzed by RT-PCR on an agarose gel stained with ethidium bromide. FIG. 7A is a photograph of the gel showing the RT-PCR for SUR1 and SUR2. FIG. 7B is a photograph of a gel showing the RT-PCR for Kir6.1 and Kir6.2. Lanes 3 and 4 in FIGS. 7A and 7B show the RT-PCR for insulinoma cells. Lanes 5 and 6 show the RT-PCR for reactive astrocytes. Lane 1 in FIGS. 7A and 7B represents ladder size markers; Lane 2 in FIGS. 7A and 7B is a blank control. In FIG. 7A, lanes 3 and 4 show the SUR1 and SUR2 experiments, respectively, in insulinoma cells. Insulinoma cells are known to express SUR1, but not SUR2. Lanes 5 and 6 in FIG. 7A show the SUR1 and SUR2 experiments in reactive astrocytes, respectively. FIG. 7A shows that SUR1 mRNA is present in reactive astrocytes, as well as in the control insulinoma cells. SUR2 is absent in both cell types. In FIG. 7B, lanes 3 and 4 show the Kir6.1 and Kir6.2 experiments in insulinoma cells, respectively. Kir6.1 is present in insulinoma cells, but Kir6.2 is not. Kir6 is the potassium channel associated with SUR1 in insulinoma cells. Lane 5 and 6 in FIG. 7B show that neither Kir6.1 nor Kir6.2 is present in reactive astrocytes. Therefore, reactive astrocytes express SUR1 mRNA, but Kir6.1 and Kir6.2 mRNA is absent from the cells.

The presence of SUR1 in reactive astrocytes combined with the regulation of the $NC_{Ca-ATP}$ channel in astrocytes by SUR antagonists indicates that SUR regulates the $NC_{Ca-ATP}$ channel of the present invention.

Example 8

Tryptic Digests

Figure 8:
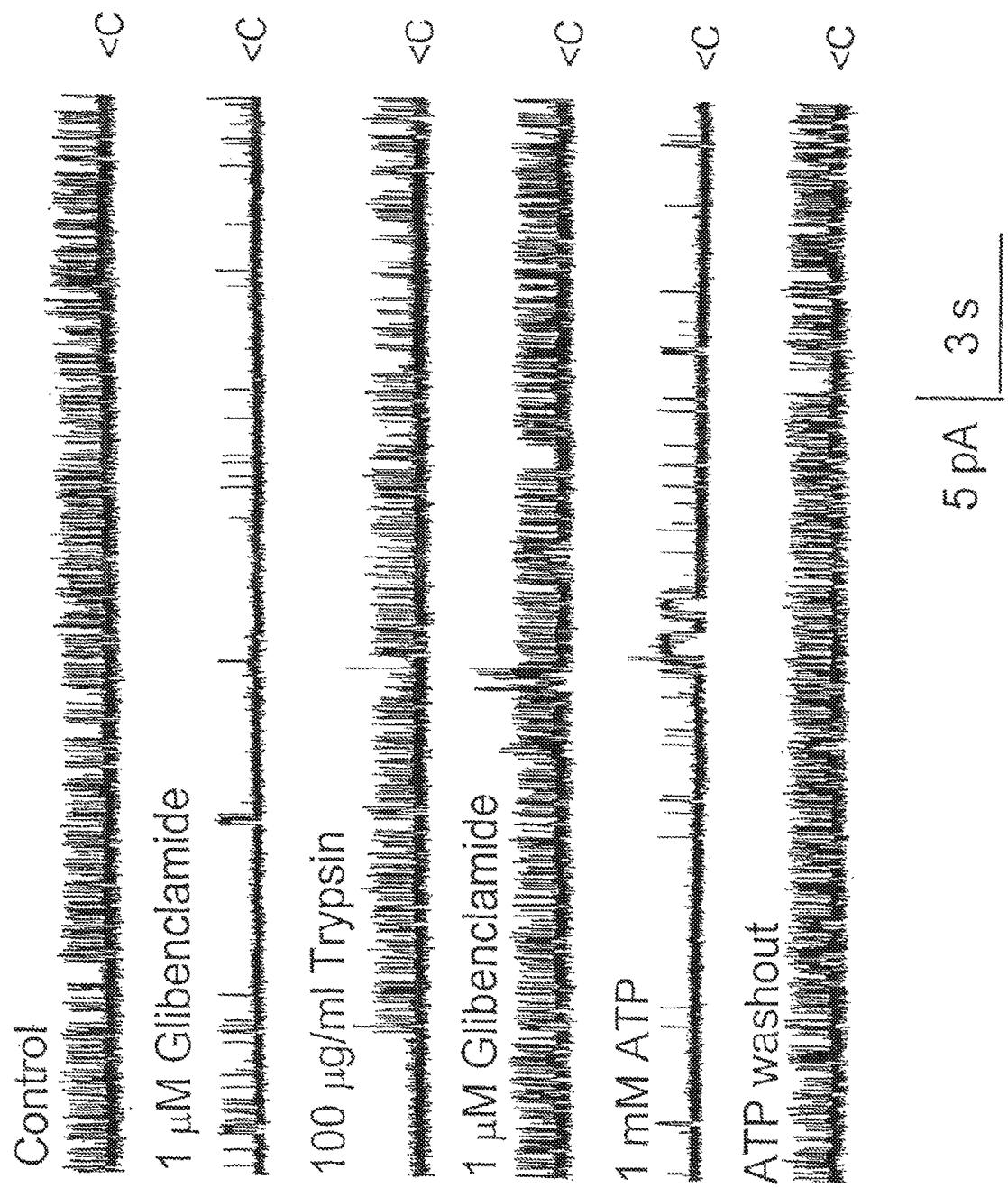
FIG. 8 shows current recordings in an inside-out patch to illustrate the effects of tryptic digestion on channel sensitivity to glibenclamide and ATP.

A characteristic feature of SUR-regulated KA-function is that tryptic digestion of the cytoplasmic face of the channel, but not its extracellular face causes loss of inhibition by sulfonylureas, without altering sensitivity to ATP and without changing the biophysical properties of the channel. The effect of trypsin on $NC_{Ca-ATP}$ function is shown in FIG. 8. Under control conditions, channel activity in the inside-out patch configuration is strongly inhibited by 1 pM glibenclamide. Exposure to 100 pg/ml trypsin on the cytoplasmic side of the membrane for 3 minutes yields a patch that still exhibits strong channel activity, but that channel activity is completely unaffected by glibenclamide. After such trypsin treatment of the cytoplasmic side, the biophysical properties of the channel, including open channel conductance, open channel times, $Ca^{2+}$-mediated activation are unchanged, and the channel still maintains its typical sensitivity to ATP. By contrast, exposure of the extracellular side of the membrane has no effect on glibenclamide inhibition. These trypsin digest data on the NCCa-An channel of the present invention provide additional supporting evidence that SUR1 is involved in regulation of the $NC_{Ca-ATP}$ channel, because the results compare to previous findings from SUR1-regulated $K_{ATP}$ channels. Linkage of a SUR to a non-selective ATP sensitive cation channel, has not been shown previously.

Assays for Compounds or Compositions that Block $NC_{Ca-ATP}$ Channel and Inhibit Neural Cell Swelling Example 9

Effects of Sulfonylurea Compounds

Figure 9A:
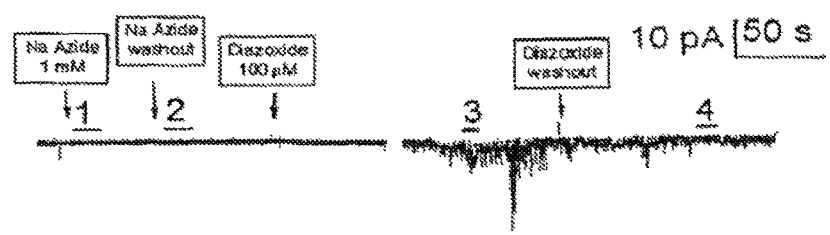
FIG. 9A shows the outside-out patch recordings with Na azide and diazoxide applied to the extracellular side of the membrane.
Figure 9B:
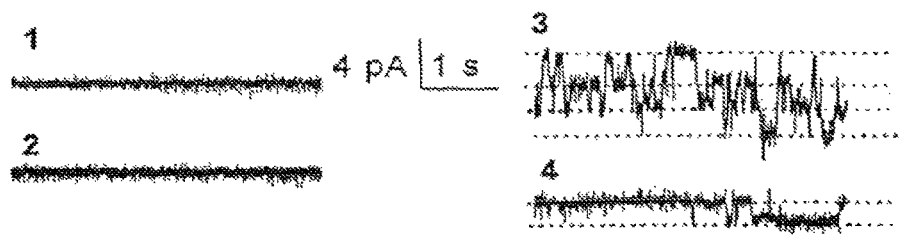
FIG. 9B shows the current records obtained from the segments marked with the corresponding numbers in FIG. 9A, at higher temporal resolution.

Sulfonylurea compounds are known to modulate the sulfonylurea receptor. A sulfonylurea receptor is generally associated with $K_{ATP}$ channels as a regulatory component, and is found in various tissues, including rat NRAs. Notably, the $K_{ATP}$ channels Kir6.1 and Kir6.2 are not present in rat NRAs (FIG. 7B). It is possible to activate the $NC_{Ca-ATP}$ channel with SUR ligand diazoxide in outside-out patches (FIGS. 9A and 9B). $NaN_3$ does not elicit channel activity in isolated membrane patches, indicating that it works via ATP depletion rather than any direct effect on the channel.

Example 10

Figure 10A:
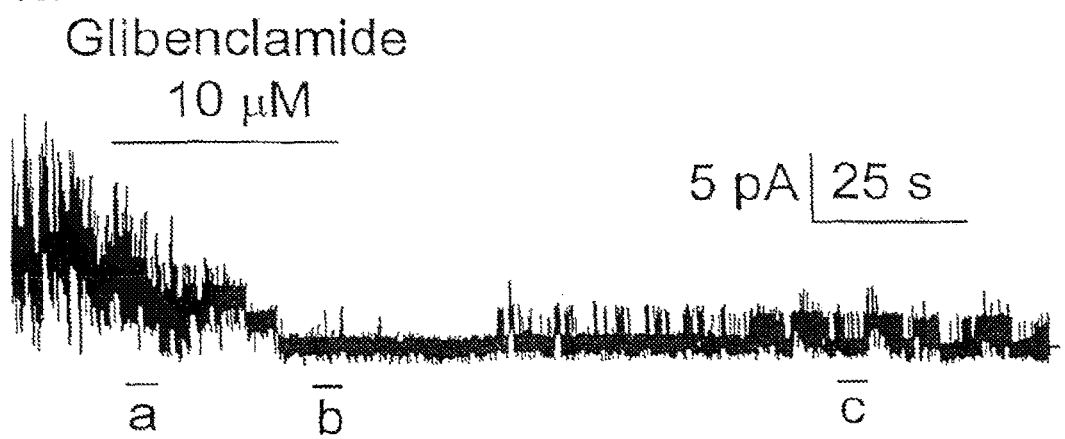
FIG. 10A shows outside-out patch recordings (a) before, (b) during, and (c) after application of glibenclamide to the extracellular side of the membrane.
Figure 10B:
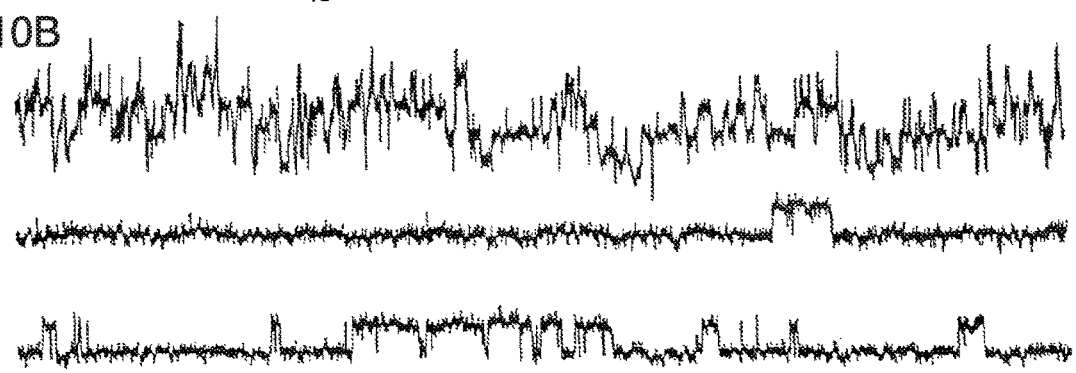
FIG. 10B shows the current records of FIG. 10A at higher temporal resolution.
Figure 10C:
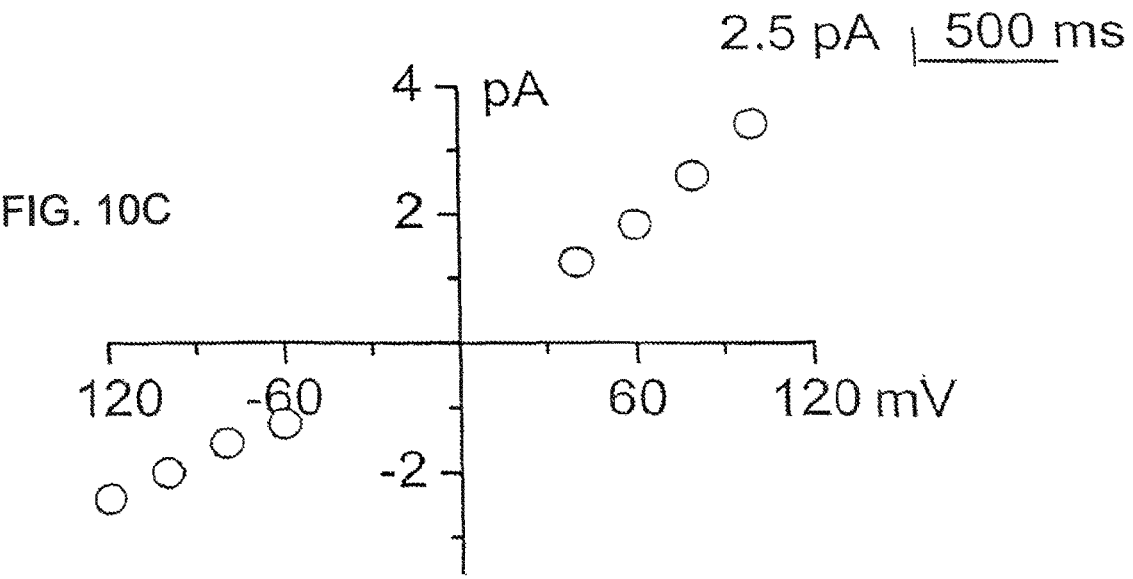
FIG. 10C show a plot of mean single channel amplitudes at the different potentials studied; the slope of the data indicates 35 pS conductance of the glibenclamide-sensitive channel.
Figure 11A:
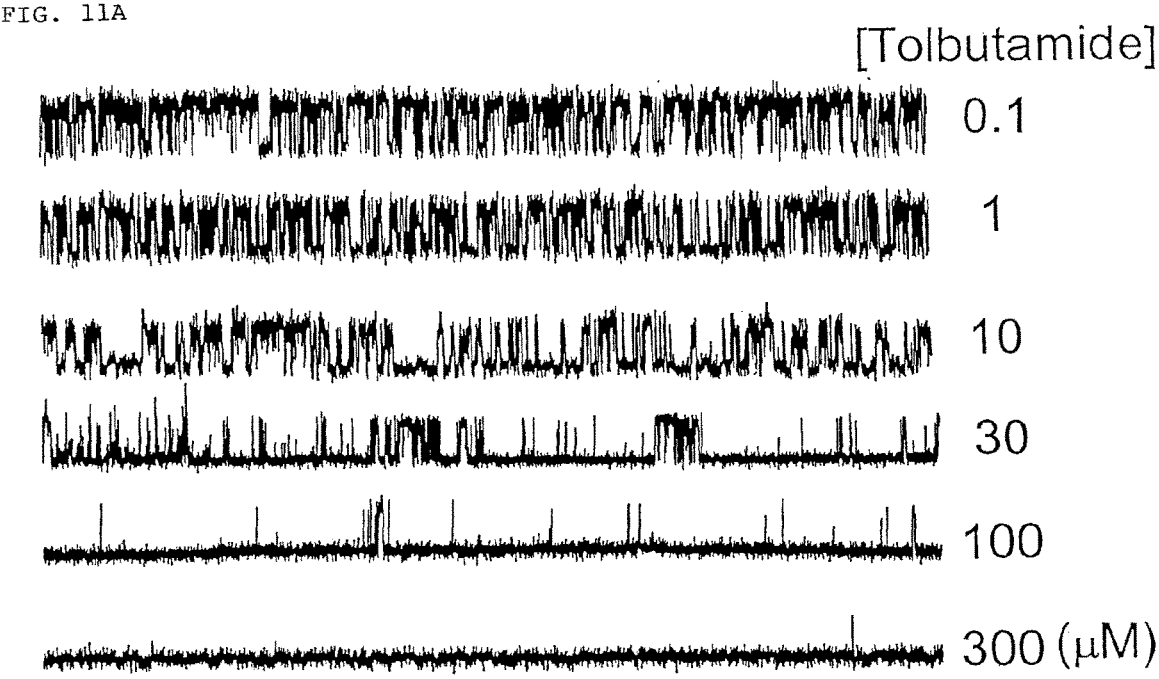
FIG. 11A shows the outside-out patch recordings with various concentrations of tolbutamide applied to the extracellular side of the membrane.
Figure 11B:
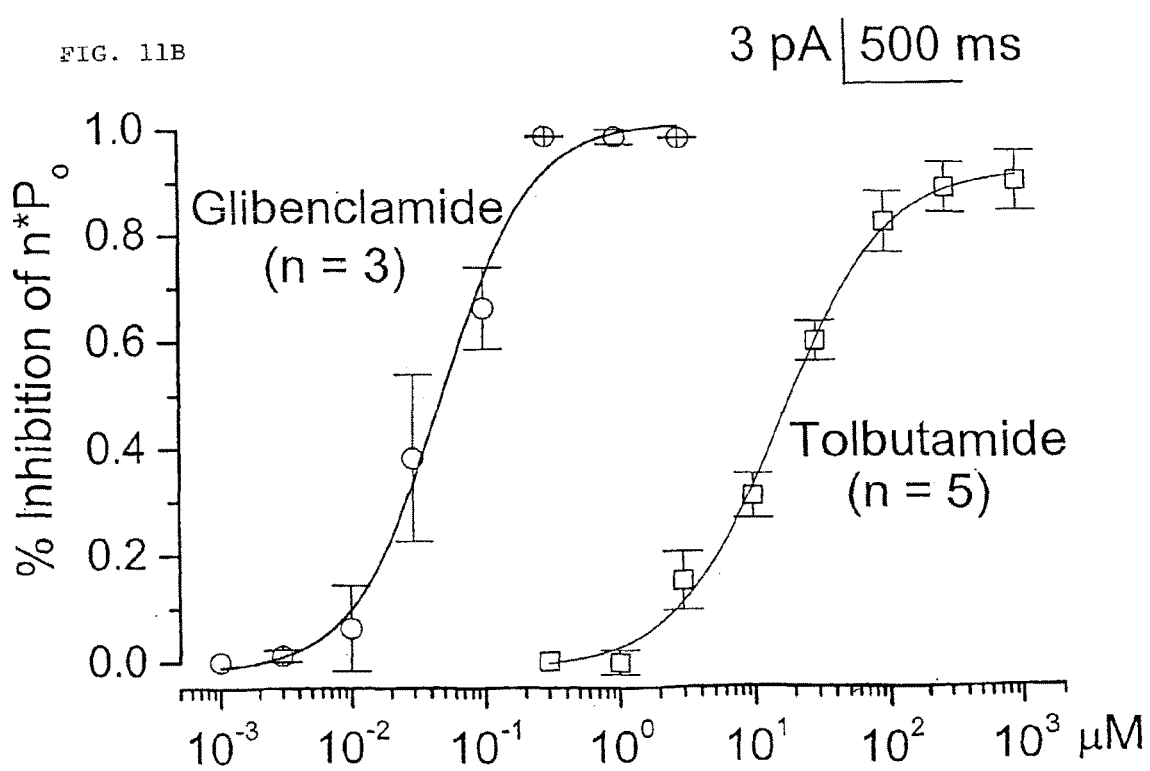
FIG. 11B shows the dose-response curves for inhibition of open channel probability by glibenclamide and tolbutamide to provide a normalized open channel probability (n·Po); data were fit to a standard logistic equation, with a Hill coefficient of 1 and half-maximum inhibition of 48 nM and 16.1 µM; values plotted are means (±SE) from 3 and 5 patches for Glibenclamide and Tolbutamide, respectively.

In Vitro Assays for Determining Dose-Dependent Blockage of the $NC_{Ca-ATP}$ Channel SUR1 blocking compounds, such as glibenclamide and tolbutamide, are known to have an inhibitory effect on $K_{ATP}$ channels. In one embodiment, the present invention arrives at the objects of the invention by providing a method in which the direct inhibitory effect of glibenclamide and tolbutamide on $NC_{Ca-ATP}$ channels is determined (FIGS. 10 and 11). Inside-out patches are used to show the inhibitory effect of sulfonylureas. To ensure that no K+ channel, particularly $K_{ATP}$ is contributing to patch current, Cs+ is used as the charge carrier. Channel activity is profoundly diminished by the addition of 10 μM glibenclamide (FIG. 10A at b), and the activity is shown to be due to a 35 pS cation channel, which is consistent with the $NC_{Ca-ATP}$ channel of the present invention (FIG. 10C). Another sulfonylurea, tolbutamide, is also shown to inhibit $NC_{Ca-ATP}$ channel activity (FIGS. 11A and 11B). AS shown in FIG. 11B, the $NC_{Ca-ATP}$ channel is blocked by the sulfonylureas in a dose-dependent manner. With tolbutamide, half maximum inhibition ($EC_{50}$) is observed at 16.1 μM with a Hill coefficient of 1.3, and channel activity is completely lost at concentrations >300 μM. With glibenclamide, $EC_{50}$ is observed at 48 μM with a Hill coefficient of 1.2. The sensitivity of the $NC_{Ca-ATP}$ channel of the present invention to blocking in NRAs with both of these sulfonylurea compounds corresponds closely to that reported in pancreatic p cells and in expression systems with SUR1, but not SUE.

This in vitro assay for determining the concentration of the test compound which achieves a half-maximal inhibition of channel activity may be used to formulate dose in animal models to achieve. a circulating plasma concentration range.

Example 11

Mechanism of Channel Regulation by Sulfonylureas

The $NC_{Ca-ATP}$ channel of the present invention exhibits two open states, with a shorter and a longer dwell time, each less than 10 ms. FIG. 12 shows data from a patch exhibiting an open channel probability (n·Po) of 0.63, with open dwell time values $\tau_{0-1}$ $\tau_{0-2}$ and of 1.9 and 8.2 ms. After successive application of 3 μM tolbutamide (FIGS. 12B and 12E) and 30 μM tolbutamide (FIGS. 12C and 12F), n·Po decreased to 0.44 and 0.09, respectively, but the open dwell time values are not appreciably affected by the drug. Closed channel dwell times are increased in duration and frequency by tolbutamide (FIGS. 12H and 12I). Thus, the channel of the present inventions exhibits a form of channel inhibition in which the blocking compound had no effect on open channel dwell times and a progressive increase in long closures. This form of channel inhibition is similar to that produced by sulfonylureas acting on the $K_{ATP}$ channel in pancreatic β cells. See, Gillis et. al., 1989; Babeenko et. al., 1999).

Example 12

Application of 100 μM of the SUR-activator diazoxide activates the 35 pS channel of the present invention, causing weak inward rectification in cell-attached patches (FIGS. 13A, 13B and 13C). To determine the type of S U R affecting activation of the $N_{Ca-ATP}$ channel of the present invention, experiments are conducted using sulfonylurea compounds that preferentially activate SUR2 over SUR1, namely cromakalin, and pinacidil. Both cromakalin and pinacidil had no effect on the $NC_{Ca-ATP}$ channel of the present invention, which is consistent with other data described herein indicating that SUR1 is associated with the $NC_{Ca-ATP}$ channel of the present invention, and activation of the channel is not mediated by SUR2.

Example 13

SUR-Mediated Cell Swelling

After addition of $NaN_3$ to deplete ATP in cells, cell blebbing typically becomes apparent in 7-10 minutes. Diazoxide is an SUR1 agonist or SUR1 activator. When diazoxide alone is added to the cells, blebbing occurs even without ATP depletion, Diazoxide, therefore, opens the channel directly without ATP depletion by activating SUR1. However, when cells are pretreated with glibenclamide, addition of $NaN_3$ does not cause blebbing, even after 30 minutes. Thus, activation of $NC_{Ca-ATP}$ channel by ATP depletion or by the channel opener, diazoxide, can result in blebbing and swelling of NRAs, and that swelling can be prevented by blocking the channel with glibenclamide. ATP depletion by Na azide can result in necrotic cell death of NRAs. This finding accords with the data described herein that glibenclamide protects from the opening of the $NC_{Ca-ATP}$ channel following ATP depletion, and that opening of this channel is responsible for cell blebbing.

The antagonist used in the methods of the present invention includes a compound that interferes with $NC_{Ca-ATP}$ function. Typically, the effect of an antagonist is observed as a blocking of $NC_{Ca-ATP}$ current in conditions under which the channel has been activated and current can be measured in the absence of the antagonist.

In addition to SUR1 specific sulfonylurea compounds, agents that block SUR1, also include compounds that are structurally unrelated to sulfonylureas. Such SUR1 blockers include a class of insulin secretagogues compounds that bind to the SUR, which were identified and developed for the treatment of type 2 diabetes. The benzarnido derivatives: repaglinide, nateglinide, and meglitinide represent one such class of insulin secretagogues, that bind to the SUR. Nateglinide is an amino acid derivative. Also, imidazoline derivatives have been identified that interact with the sulfonylurea receptor (SUR) 1 subunit such as midaglizole (KAD-1229), LY397364 and LY389382.

In one preferred embodiment of the present invention, compounds that preferentially block SUR1, but not SUR2, are used in the method of the present invention. Such compounds include tolbutamide and gliclazide. The following compounds block both SUR1 and SUR2: glibenclamide, glimepiride, repaglinide, and meglitinide. In yet another embodiment of the method of the present invention, administration is combined with MgADP, which has been show to produce an apparent increase of sulfonylurea efficacy on channels containing SUR1, but not SUR2.

Example 14

To determine whether $NC_{Ca-ATP}$ activation by ATP depletion initiates necrosis of reactive astrocytes that express this channel, studies are conducted to determine if glibenclamide is capable of protecting reactive astrocytes from cell death by inhibiting $NC_{Ca-ATP}$ channel activity via its action on SUR1. Two types of cell death, apoptosis and necrosis, are assessed following ATP depletion.

Thus, activation of $NC_{Ca-ATP}$ channel is responsible for necrotic death of NRAs following ATP depletion, and that glibenclamide can prevent this form of cell death.

In this Example, the preparation of freshly isolated NRAs was further purified by removal of RBCs, as described herein to provide a cell population having <1% RBCs. Over 95% of cells had resting potentials near EK, suggesting that the enzymatic dissociation method had not appreciably harmed the cells. Over 95% of cells are positive for the astrocyte marker, glial fibrillary acidic protein (GFAP) as determined by immunofluorescence. When examined by phase microscopy, the NRAs are of various sizes, ranging from 11-45 pms in diameter, some of which are phase bright and others are phase dark. A subgroup of phase bright cells had multiple short but distinct cell processes that are shorter than the cell soma. In this Example, only larger (≈30 μm diameter), phase bright cells with short processes (<1 cell length) are studied. This population of NRAs reliably express the $NC_{Ca-ATP}$ channels.

Experiments are conducted at room temperature (22-25° C.) within 24 hr of cell isolation. An aliquot of cells is placed on a chamber slide (LAB-TEK, Naperville, Ill.) filled with extracellular bath solution containing (a): NaCl 130, KCl 10, $CaCl_2$ 1, $MgCl_2$ 1, HEPES 32.5, glucose 12.5, pH 7.4. After viable cells adhered to the surface, any residual debris not previously removed by centrifugation is washed away by flushing with excess solution. Cells are subjected to ATP depletion by 1 mM Na azide to activate (open) the $NC_{Ca-ATP}$ channels, and then incubated with glibenclamide (1 μM).

Thereafter, the cells are examined by propidium iodide (PI) staining for evidence of cellular membrane permeabilization, an indication of early oncotic or necrotic cell death. See, Barros et al., 2001. The cells are also examined by fluorescein-tagged annexin V binding for evidence of externalization of the phosphoaminolipid phosphotidylserine from the inner face of the plasma membrane to the outer surface, an early indication of apoptosis. See, Clodi et al., 2000; Rucker-Martin et al., 1999. Staining procedure are conducting according to manufacture directions (Vybrant Apoptosis Assay Kit 2, Molecular Probes). Slides are mounted using ProLong antifade mounting medium (Molecular Probes). Signals are visualized using a Nikon Diaphot epifluorescent microscope (Leitz Wetzlar). Images are captured and stored using a SenSys digital camera (Roper Scientific Inc.) and IPLab software (version 3.0; Scanalytics Inc.). Annexin V-positive cells or PI-positive cells are counted in 20 individual fields using a 20× objective lens. Mean values of positive cells in 20 fields for various treatment groups are compared using ANOVA Pairwise multiple comparisons, with $p<0.05$ being considered as indicating a significant difference.

Figure 15A:
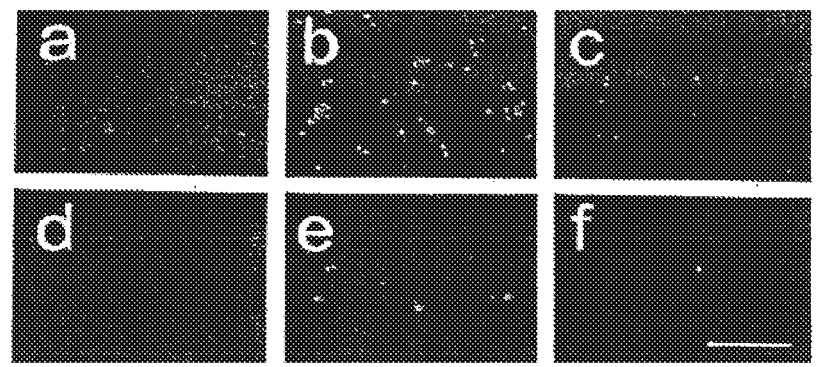
FIG. 15A has photomicrographs of the epifluorescence images of cells exposed to different compounds and labeled with gropidium iodide (upper panel a, b and c) or annexin V (lower panel d, e and f). The compounds were: control (a & d), 1 mM Na azide (b & e), 1 mM Na azide plus 1 μM glibenclamide (c & f).
Figure 15B:
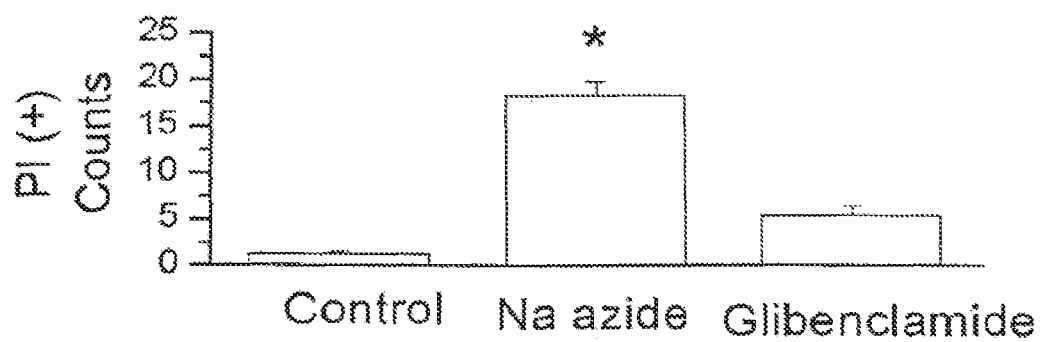
FIG. 15B has bar graphs showing cell-counts for propidium iodide labeling; pairwise multiple comparisons indicated a significant difference (p<0.05) with Na azide treatment.
Figure 15C:
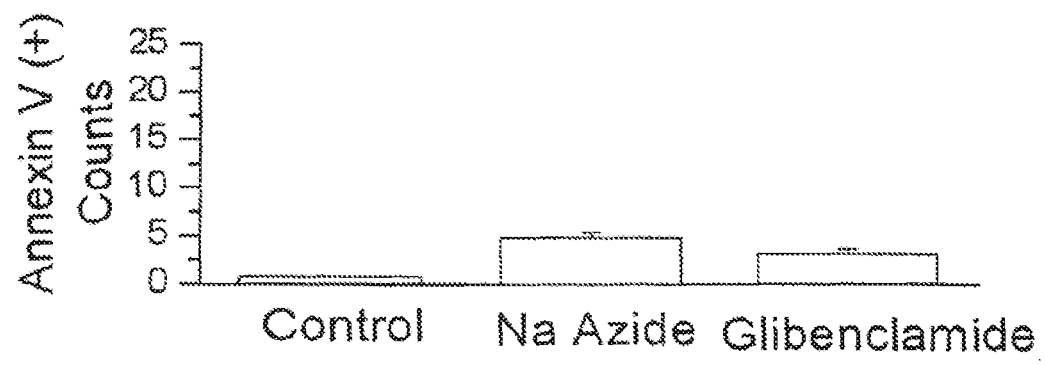
FIG. 15C has bar graphs showing cell-counts for annexin V staining; pairwise multiple comparisons indicated no significant difference with any treatment.

The fluorescence microscopy photos shown in FIG. 15A show that under baseline (control) conditions, both annexin V-positive and PI-positive cells (photos a and d, respectively) are rare in the cell isolates. After a 10-min incubation with Na aide (1 mM), the number of PI-positive cells increased substantially ($p<0.05$) (FIG. 15A at photo b and FIG. 15B). This indicates that ATP depletion triggers necrotic death in these cells. By contrast, Na azide treatment caused the number of annexin V-positive cells to increase slightly; the increase not being statically significant ($p>0.05$) (FIG. 15A at photo e and FIG. 15C). This indicates that apoptotic death was not a major endpoint of ATP depletion in these cells.

Pretreatment of cells with glibenclamide (1 μM) at the time of administration of Na aide dramatically decreased the number of PI-positive cells ($p<0.05$; FIG. 15A at photo c and FIG. 15B), indicating significant protection from necrotic death following ATP depletion. The number of NRAs undergoing apoptotic death also decreased with glibenclamide, as indicated by annexin V labeling (FIG. 15A at photo f and FIG. 15C), but values for this group were not significantly different.

This data indicate that the $NC_{Ca\text{-}ATP}$ channel is involved in the mechanism of the necrotic cell death of reactive astrocytes. This Example shows that necrotic, rather than apoptotic, cell death is the principal endpoint of ATP depletion in these cells. Therefore, ATP depletion by Na azide initiates cell death by removal of the ATP block of the $NC_{Ca\text{-}ATP}$ channel, thus initiating oncotic cell swelling. Involvement of this channel in oncotic cell swelling is confirmed by showing that necrotic death can also be induced by diazoxide, the channel opener that activates the $NC_{Ca\text{-}ATP}$ channel in these cells, and could be blocked by glybenclamide, which prevents opening of the $NC_{Ca\text{-}ATP}$ channel. The involvement of the $NC_{Ca\text{-}ATP}$ channel in cell death of reactive astrocytes provides a mechanism and target of death in these cells, as well as the importance of blocking the $NC_{Ca\text{-}ATP}$ channel to prevent the death of reactive astrocytes, which occurs in traumatic brain injury.

Example 15

In Vitro Assays for Determining a Test Compound Ability to Provide Dose-Dependent Blockage of the $NC_{Ca\text{-}ATP}$ Channel $NC_{Ca\text{-}ATP}$ channels blocking compounds can be identified by a method in which the direct inhibitory effect of the test compound on $NC_{Ca\text{-}ATP}$ channels is determined. Inside-out patches are used to show the inhibitory effect of the compound. To ensure that no K+ channel, particularly $K_{ATP}$ is contributing to patch current, Cs+ is used as the charge carrier. Compounds that profoundly diminish channel activity, and the activity is shown to be due to a 35 pS cation channel, such a compound is identified as a compound that blocks the $NC_{Ca\text{-}ATP}$ channels and is capable of inhibiting neuronal cell swelling and brain swelling. Varying concentrations of the compound are used to determine whether the $NC_{Ca\text{-}ATP}$ channel is blocked by the compound in a dose-dependent manner. The concentration at which half maximum inhibition ($EC_{50}$) is observed and the concentration at which channel activity is completely lost are determined. The sensitivity of the $NC_{Ca\text{-}ATP}$ channel of the present invention to blocking in NRAs with the test compound can be compared. This in vitro assay for determining the concentration of the test compound which achieves a half-maximal inhibition of channel activity may be used to formulate dose in animal models to achieve a circulating plasma concentration range.

Example 16

In Vivo Assays for Determining Dose-Dependent Blockage of the $NC_{Ca\text{-}ATP}$ Channel The concentration of the test compound which achieves a half-maximal inhibition of channel activity is used to formulate dose in animal models to achieve a circulating plasma concentration range. The dose of test compound that achieves a circulating plasma concentration range calculated by methods known in the art is administered to an animal having brain injury or cerebral ischemia. To determine whether the test compound prevents, inhibits or diminishes brain swelling, the epidural pressure and/or intracranial pressure of the animal is measured, such as by using a microballoon, to quantitatively monitor brain swelling. Also, the swelling can be monitored by magnetic resonance (MR) imaging. Three different studies start administration prior to, at the time of, or after the brain injury. A compound that provided diminishes brain swelling, as compared to controls, is identified as a compound capable of inhibiting neuronal cell swelling and brain swelling. Varying concentrations of the compound are used to determine whether the compound delivers efficacy in a dose-dependent manner. The dose at which half maximum inhibition is observed and the concentration at which brain swelling is most quickly alleviated are determined. Formulations are produced comprising the optimal effective dose of the test compound for preventing, inhibiting, or diminishing brain swelling, along with a pharmaceutically acceptable carrier.

Summary of $NC_{Ca\text{-}ATP}$ Channel Characteristics

The characteristics of cells expressing and composition containing the $NC_{Ca\text{-}ATP}$ channel of the present invention are summarized in Table 1.

TABLE 1

Properties of cells and membrane compositions containing the $NC_{Ca\text{-}ATP}$ Channel of the Present Invention

| | Reactive Astrocytes | Membrane Preparation derived from freshly isolated native reactive astrocytes |
|---|---|---|
| Monovalent cation permeable? | Yes: NA+ K+ | Yes: NA+ K+ |

TABLE 1-continued

Properties of cells and membrane compositions containing
the $NC_{Ca-ATP}$ Channel of the Present Invention

| | Reactive Astrocytes | Membrane Preparation derived from freshly isolated native reactive astrocytes |
|---|---|---|
| | Li+ | Li+ |
| | Rb+ | Rb+ |
| | Cs+ | Cs+ |
| | (NA+ ≈ K+ ≈ Li+ ≈ Rb+) | (NA+ ≈ K+ ≈ Li+ ≈ Rb+) |
| Anion permeable? | No | No |
| Divalent cation permeable? | No | No |
| Compounds blocking channel activity | SUR1 antagonists | SUR1 ANTAGONISTS |
| Channel opening Requires: | Intracell. ATP depletion Intracell. $Mg^{2+}$ | INTRACELL. ATP DEPLETION INTRACELL. $MG^{2+}$ |
| Single Channel Conductance | ~35 pS | ~35 PS |
| Activation [$Ca^{2+}$] | <1.0 μM | <1.0 MM |
| [ATP]$_I$ $EC_{50}$ (um) | 0.79 μM | 0.79 MM |
| ADP | No channel effect | No channel effect |
| AMP | | |
| Pore radius (nm) | 0.41 | 0.41 |

Methods of the Present Invention

The present invention provides a previously unknown ion channel found in mammalian neural cells that plays a role in cell swelling. The present invention further provides a method of screening for antagonists to the channel and a new use for antagonists to the channel, including sulfonylurea compounds such as glibenclamide and tolbutamide, as a treatment for brain swelling in mammals.

Methods of the present invention for identifying compounds that interact with, (e.g., bind to, open, block) the $NC_{Ca-ATP}$ channel and employ (i) cell based assays and/or (ii) non-cell based assay systems. Such compounds may act as antagonists or agonists of NCCa-Ap channel activity. In a preferred embodiment of the present invention, antagonists that block and/or inhibit the permeability of the $NC_{Ca-ATP}$ channel are utilized in methods for treating neural cell swelling and/or brain swelling.

The cell based assays use neural cells that express the $NC_{Ca-ATP}$ channel, preferably a functional $NC_{Ca-ATP}$ channel; the preferred cells are "MS. The non-cell based assay systems include membrane preparations that express the $NC_{Ca-ATP}$ channel, preferably a functional $NC_{Ca-ATP}$ channel. Cell-based assays include, but are not limited to, compound binding assays, microscopic observation of cell status (normal, blebbing, swelling), and measuring channel currents both before and after exposure to compound. Compositions comprising membrane preparations expressing the $NC_{Ca-ATP}$ P channel may be used to identify compounds that interact with, bind to, block or open the $NC_{Ca-ATP}$ P channel or SUR1. The term "expressing the $NC_{Ca-ATP}$ channel" or "expresses the $NC_{Ca-ATP}$ channel" means having a functional $NC_{Ca-ATP}$ channel. The term "functional $NC_{Ca-ATP}$ channel" as used herein means an $NC_{Ca-ATP}$ channel capable of being detected. One preferred method of detecting the $NC_{Ca-ATP}$ channel is by determining, in vitro or in vivo, whether the channel is open, closed and/or blocked.

For example, in a typical experiment using a membrane preparation, NRAs that express the $NC_{Ca-ATP}$ channel are used to produce the membrane preparation. Methods for producing membranes from whole cells and tissues are well known in the art. One such method produces purified cell membranes in the form of a purified microsomal fraction isolated from disrupted cells or a tissue sample by discontinuous sucrose gradient centrifugation. Also included are membranes comprised of cell-attached patches, inside-out patches, or outside-out patches. One example of a tissue sample expressing $NC_{Ca-ATP}$ channels is brain tissue adjacent to brain injury.

The membranes preparations are used in a number of assays, including, but not limited to measuring channel currents, both before and after exposure to compound; and in vitro binding assays. The experimental conditions for such assays to determine and quantify the status of the $NC_{Ca-ATP}$ channel are described throughout the instant specification, including binding assay conditions, bath compositions, pipette solutions, concentrations of ATP and $Ca^{2+}$ required, membrane voltage, membrane potentials, compound quantity ranges, controls, etc.

Binding assays and competitive binding assays employ a labeled ligand or antagonist of the $NC_{Ca-ATP}$ channel. In one such experiment, labeled Glibenclamide, such as FITC-conjugated glibenclamide or radioactively labeled glibenclamide is bound to the membranes and assayed for specific activity; specific binding is determined by comparison with binding assays performed in the presence of excess unlabelled antagonist.

In one method for identifying $NC_{Ca-ATP}$ channel blockers, membranes are incubated with a labeled compound shown to block this channel, in either the presence or absence of test compound. Compounds that block the $NC_{Ca-ATP}$ channel and compete with the labeled compound for binding to the membranes will have a reduced the signal, as compared to the vehicle control samples. In another aspect of the invention the screens may be designed to identify compounds that compete with the interaction between $NC_{Ca-ATP}$ channel and a known (previously identified herein) $NC_{Ca-ATP}$ channel antagonist or SUR1 antagonist, such as glibenclamide. In such screens, the known $NC_{Ca-ATP}$ channel antagonist or SUR1 antagonist is labeled and the test compounds are then assayed for their ability to compete with or antagonize the binding of the labeled antagonist.

The assays described herein can be used to identify compounds that modulate or affect $NC_{Ca-ATP}$ channel activity. For example, compounds that affect $NC_{Ca-ATP}$ channel activity include but are not limited to compounds that bind to the $NC_{Ca-ATP}$ channel or SUR1, inhibit binding of identified blockers or ligands (such as glibenclamide), and either open/activate the channel (agonists) or block/inhibit the channel (antagonists).

Assays described can also identify compounds that modulate neural cell swelling (e.g., compounds which affect other events involved in neural cell swelling that are activated by ligand binding to or blocking of the $NC_{Ca-ATP}$ channel).

Compounds Screened in Accordance with the Invention

The compounds for screening in accordance with the invention include, but are not limited to organic compounds, peptides, antibodies and fragments thereof, peptidomimetics, that bind to the $NC_{Ca-ATP}$ channel and either open the channel (i.e., agonists) or block the channel (i.e., antagonists). For use in the treatment of neural cell swelling or brain swelling, compounds that block the channel are preferred. Agonists that open or maintain the channel in the open state include peptides, antibodies or fragments thereof, and other organic compounds that include the SUR1 subunit of the $NC_{Ca-ATP}$ channel (or a portion thereof) and bind to and "neutralize" circulating ligand for SUR1.

With reference to screening of compounds that affect the $NC_{Ca-ATP}$ channel, libraries of known compounds can be screened, including natural products or synthetic chemicals, and biologically active materials, including proteins, for compounds which are inhibitors or activators. Preferably, such a compound is an $NC_{Ca-ATP}$ antagonist, which includes an $NC_{Ca-ATP}$ channel inhibitor, an $NC_{Ca-ATP}$ channel blocker, a SUR1 antagonist, SUR1 inhibitor, and/or a compound capable of reducing the magnitude of membrane current through the channel.

Compounds may include, but are not limited to, small organic or inorganic molecules, compounds available in compound libraries, peptides such as, for example, soluble peptides, including but not limited to members of random peptide libraries; (see, e.g., Lam, K. S. et al., 1991, Nature 354: 82-84; Houghten, R. et al., 1991, Nature 354: 84-86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72: 767-778), antibodies (including, but not limited to, polyclonal, monoclonal, humanized, anti-idiotypic, chimeric or single chain antibodies, and FAb, F(ab').sub.2 and FAb expression library fragments, and epitope-binding fragments thereof).

Other compounds which can be screened in accordance with the invention include but are not limited to small organic molecules that are able to cross the blood-brain barrier, gain entry into an appropriate neural cell and affect the expression of the $NC_{Ca-ATP}$ channel gene or some other gene involved in the $NC_{Ca-ATP}$ channel activity (e.g., by interacting with the regulatory region or transcription factors involved in gene expression); or such compounds that affect the activity of the $NC_{Ca-ATP}$ channel or the activity of some other intracellular factor involved in the $NC_{Ca-ATP}$ channel activity.

Computer modeling and searching technologies permit identification of compounds, or the improvement of already identified compounds, that can modulate $NC_{Ca-ATP}$ channel activity or expression. Having identified such a compound or composition, the active sites or regions are identified. Such active sites might typically be ligand binding sites. The active site can be identified using methods known in the art including, for example, from study of complexes of the relevant compound or composition with other ligands, from the amino acid sequences of peptides, or from the nucleotide sequences of nucleic acids. Chemical or X-ray crystallographic methods can be used to study complexes of the relevant compound to find the active site. The three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential $NC_{Ca-ATP}$ channel modulating, preferably blocking, compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Examples of molecular modeling systems are the CHARMm and QUANTA programs (Polygen Corporation, Waltham, Mass.). CHARMm performs the energy minimization and molecular dynamics functions. QUANTA performs the construction, graphic modeling and analysis of molecular structure. QUANTA allows interactive construction, modification, visualization, and analysis of the behavior of molecules with each other. A number of articles review computer modeling of drugs interactive with specific proteins, such as Rotivinen, et al.) 1988, Acta Pharmaceutical Fennica 97: 159-166); Ripka (1988 New Scientist 54-57); McKinaly and Rossmann (1 989, Annu. Rev. Pharmacol. Toxicol. 29: 11 1-122); Perry and Davies, OSAR: Quantitative Structure-Activity Relationships in Drug Design pp. 189-193 Alan R. Liss, Inc. 1989; Lewis and Dean (1989, Proc. R. SOC. Lond. 236: 125-140 and 141-162); and, with respect to a model receptor for nucleic acid components, Askew, et al. (1989, J. Am. Chem. SOC. 11 1: 1082-1 090). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Compounds identified via assays such as those described herein may be useful, for example, in elaborating the biological function of the $NC_{Ca-ATP}$ channel and for relief of brain swelling.

Assays for testing the efficacy of compounds identified in the cellular screen can be tested in animal model systems for brain swelling. Such animal models may be used as test substrates for the identification of drugs, pharmaceuticals, therapies and interventions which may be effective in treating brain swelling. For example, animal models of brain swelling, such as brain injury, may be exposed to a compound, suspected of exhibiting an ability to inhibit brain swelling, at a sufficient concentration and for a time sufficient to elicit such an inhibition of brain swelling in the exposed animals. The response of the animals to the exposure may be monitored using visual means (e.g., radiological, CAT, MRI), measurement of intracranial pressure, and/or the reversal of symptoms associated with brain swelling. With regard to intervention, any treatments which reverse any aspect of brain swelling-associated symptoms should be considered as candidates for brain swelling therapeutic intervention. Dosages of test agents may be determined by deriving dose-response curves, as discussed herein.

Accordingly, the present invention is useful in the treatment or alleviation of neural cell swelling and death and brain swelling, especially those brain insults related to traumatic brain injury, central or peripheral nervous system damage, cerebral ischemia, such as stroke, or complications involving and/or stemming from edema, injury, or trauma. Such damage or complications may be characterized by an apparent brain damage or aberration, the symptoms of which can be reduced by the methods of the present invention including the administration of an effective amount of the active compounds or substances described herein. According to a specific embodiment of the present invention the administration of effective amounts of the active compound can block the channel, which if remained open leads to neural cell swelling and cell death. A variety of antagonists to SUR1 are suitable for blocking the channel. Examples of suitable SUR1 antagonists include, but are not limited to glibenclamide, tolbutamide, repaglinide, nateglinide, meglitinide, midaglizole, LY397364, LY3 89382, gliclazide, glimepiride, MgADP, and combinations thereof. In a preferred embodiment of the invention the SUR1 antagonists is selected from the group consisting of glibenclamide and tolbutamide. Still other therapeutic "strategies" for preventing neural cell swelling and cell death can be adopted including, but not limited to methods that maintain the neural cell in a polarized state and methods that prevent strong depolarization.

Example 17

Additional Mechanisms for Maintaining NRAS in a Polarized State

When reactive astrocytes are strongly depolarized due to opening of the $NC_{Ca-ATP}$ channel, they undergo blebbing and swelling and eventually sustain necrotic cell death. As stated above, when reactive astrocytes are strongly depolarized due to opening of a non-selective channel that is sensitive to $Ca^{2+}$ and ATP ($NC_{Ca-ATP}$ channel), they undergo blebbing and swelling and eventually sustain necrotic cell death. The death of these reactive astrocytes can be prevented if strong depolarization can be prevented, in other words, if the cells can be maintained in a polarized state.

One potential way of maintaining the NRAs in a polarized state is to open the Kir2.3 channel. NRAs are exposed to the Kir2.3 channel opener, Tenidap, to maintain Kir2.3 channels open. Native reactive astrocytes freshly harvested from adult rat brains after injury are exposed to Tenidap to evaluate the drug's ability to open the Kir2.3 channel in these cells. Preferably, type 1 reactive (RI) astrocytes are harvested and used in this assay. One of the subtypes of reactive astrocytes is the type R1 astmcyte. Type R1 astrocytes comprise the largest population of recoverable astrocytes at the site of brain injury. They are characteristically located in the region of tissue surrounding the injury site, many of which are found to have migrated into the injury site itself. See, Perillan, et al., 1999.

The reactive astrocytes that are part of the cellular response to TBI and stroke are comprised of at least two subtypes. One of the subtypes of reactive astrocytes is the type R1 astrocyte. Type R1 astrocytes comprise the largest population of recoverable astrocytes at the site of brain injury. They are characteristically located in the region of tissue surrounding the injury site, with many of these cells also being found to have migrated into the injury site itself. See, Perillan, et al. 1999.

Type R1 astrocytes are the predominant type of reactive astrocyte in the NRA preparations. Type R1 astrocytes express two critically important ion channels in their cell membrane: (a) the Kir2.3 channel, which is present in cultured as well as freshly isolated cells; and (b) the $NC_{Ca-ATP}$ channel, which is present only in freshly isolated reactive astrocytes and lost shortly after culturing. The Kir2.3 is an inward rectifier channel that is critically important for maintaining the cell polarized to a normal resting potential near the potassium reversal potential ($\approx -75$ mV). When this channel is inactivated or inhibited, the cell depolarizes to a potential near the chloride reversal potential ($\approx -25$ mV). Characteristic features of the $NC_{Ca-ATP}$ channel are: 1) it is a non-selective cation channels that allows passage of Nay K and other monovalent cations quite readily; 2) it is activated by an increase in intracellular calcium, and/or by a decrease in intracellular ATP; and 3) it is regulated by sulfonylurea receptor type 1 (SUR1). SUR1 had been considered to be associated exclusively with $K_{ATP}$ channels, such as those found in pancreatic β cells.

Opening of the $NC_{Ca-ATP}$ channel following ATP depletion, as with ischemia or hypoxia, causes depolarization of the cell due to influx of Na. This influx of Na increases the osmotic load within the cell, and as a result, $H_2O$ enters the cell to equilibrate the osmotic load. The result is an excess of Na and $H_2O$ intracellularly, a pathological response that produces cell blebbing and cell swelling and that is known as cytotoxic edema. Left unchecked, this pathological response eventually leads to cell death. As disclosed herein, this cell death is mostly necrotic cell death but to a lesser extent, apoptotic cell death as well.

A number of approaches may be used to meliorate brain swelling due to cytotoxic edema. One currently used treatment for treating patients in relevant clinical situations is based on increasing extracellular osmolarity to reduce the driving force for influx of $H_2O$. This strategy also reduces blebbing in isolated cells.

A more specific strategy to reduce cytotoxic edema is inactivating or blocking the $NC_{Ca-ATP}$ channel that is primarily responsible for the influx of Na that draws $H_2O$ into the cell and that actually causes cytotoxic edema. One highly selective approach to inactivating this channel is to exploit the unique relationship between the channel and the controlling regulatory subunit, SUR1. A variety of drugs have been developed that interact with SUR1 in pancreatic p cells to block the $K_{ATP}$ channel in those cells and thereby treat diabetes. Some of these drugs belong to the class of agents called sulfonylureas. As described herein, drugs that block the $K_{ATP}$ channel, such as glybenclamide and tolbutamide, are highly effective at blocking the $NC_{Ca-ATP}$ channel in type RI astrocytes. Drugs capable $NC_{Ca-ATP}$ channel blocking in NRAs (a) prevents cell blebbing in response to ATP depletion, (b) significantly reduces cell death following ATP depletion. Also, the use of glybenclamide to treat brain swelling in an animal suffering from stroke or brain injury is described herein.

Yet another strategy to oppose the effect of the $NC_{Ca-ATP}$ channel and reduce cytotoxic edema would be to counteract depolarization of the cell that accompanies opening of the $NC_{Ca-ATP}$ channel. One way to accomplish this is to enhance opening of the Kir2.3 channels that are also present in these cells. An anti-inflammatory compound, Tenidap, is an opener of Kir2.3 channels. See, Popp et al., 1992; Liu et al., 2002. [OO1SO] Tenidap is evaluated for its ability to reduce cell blebbing and swelling and necrotic cell death in response to ATP depletion in the isolated cells as well as in situ in injured rat brain. To assess whether Tenidap opens the Kir2.3 channels in type R1 astrocytes, using methods similar to those described herein for evaluating the status of the $NC_{Ca-ATP}$ channel. Results from such experiments that show Tenidap to open Kir2.3 channels in type R1 astrocytes, and reduce cell blebbing and cell death in response to ATP depletion would indicate the usefulness of Tenidap in treating brain swelling and cytotoxic edema resulting from TBI or cerebral ischemia. The effective amount of Tenidap is that amount capable of reducing brain swelling or cerebral ischemia due to the drug's ability to inhibit neural cell swelling and necrotic cell death.

SUR1 blockers are likely to be the most specific, reliable provide the fewest untoward side effects. Further, a combination of treatments including use of osmotic diuretics, $NC_{Ca-ATP}$ channel blockers such glybenclamide and Kir2.3 channel openers such as Tenidap may provide better efficacy in ameliorating cytotoxic edema and reducing morbidity and mortality in brain injury and stroke.

It is therefore another object of the present invention to provide a method for identifying compounds that inhibit neural cell swelling, comprising: (a) contacting a test compound with a composition comprising the Kir2.3 channel, and (b) determining whether the test compound opens the Kir2.3 channel, wherein a test compound that opens the Kir2.3 channel is identified as a compound for inhibiting neural cell swelling.

It is yet another object of the present invention to provide a method for a method for identifying compounds that inhibit brain swelling, comprising: (a) contacting a test compound with a composition comprising the Kir2.3 channel, and (b) determining whether the test compound opens the Kir2.3 channel, wherein a test compound that opens the Kir2.3 channel is identified as a compound for inhibiting brain swelling.

It is yet another object of the present invention to provide a method for a method for identifying compounds that inhibit neural cell swelling and/or brain swelling in an animal, comprising: (a) contacting a test compound with a composition comprising the Kir2.3 channel, and (b) determining whether the test compound opens the Kir2.3 channel, wherein a test compound that opens the Kir2.3 channel is identified as a compound for inhibiting neural cell swelling and/or brain swelling in an animal.

It is a further object of the present invention to provide a method for identifying compounds that prevent, inhibit and/or alleviate brain swelling in a subject, comprising: (a) contacting a test compound with a composition comprising the Kir2.3 channel, and determining whether the test compound opens the Kir2.3 channel, and (b) administering the test compound to a subject having a brain injury or cerebral ischemia, and determining whether the test compound prevents, inhibits and/or alleviates brain swelling in the subject, wherein test compounds that open the Kir2.3 channel are identified as compounds that inhibit brain swelling.

It is a further object of the present invention to provide a method for identifying compounds that inhibit neural cell swelling in an animal, comprising: (a) contacting a test compound with a composition comprising the Kir2.3 channel, and determining whether the test compound opens the Kir2.3 channel, and (b) administering the test compound to an animal having a brain injury or cerebral ischemia, and determining whether the test compound inhibits brain swelling of the treated animal, wherein test compounds that inhibit brain swelling are identified as compounds that inhibit neural cell swelling in an animal.

It is also an object of the present invention to provide a method of preventing neural cell swelling in the brain of a subject, said method comprising administering to the subject a formulation containing an effective amount of a compound that opens the Kir2.3 channel and a pharmaceutically acceptable carrier.

It is a further objection of the present invention to provide a method of alleviating the negative effects of traumatic brain injury or cerebral ischemia stemming from neural cell swelling in a subject, comprising administering to the subject a formulation comprising an effective amount of a compound that opens the Kir2.3 channel and a pharmaceutically acceptable carrier. In the object of the present invention that provide methods assessing the effect of a compound on the Kir2.3 channel, a preferred compound is Tenidap. For example the formulation may provide a daily dose of Tenidap that is from about 10 mg/day to about 500 mg/day, or, when administered directly to the brain the daily dose of Tenidap is from about 500 mg/day to 1.5 gms/day or greater.

Pharmaceutical Formulations and Methods of Treating Neural Cell Swelling and Brain Swelling Compositions of the Present Invention The present invention also contemplates therapeutic methods employing compositions comprising the active substances disclosed herein. Preferably, these compositions include pharmaceutical compositions comprising a therapeutically effective amount of one or more of the active compounds or substances along with a pharmaceutically acceptable carrier.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

Dose Determinations

By a "therapeutically effective amount" or simply "effective amount" of an active compound, such as glibenclamide or tolbutamide, is meant a sufficient amount of the compound to treat or alleviate the brain swelling at a reasonable benefit/risk ratio applicable to any medical treatment. It will be understood, however, that the total daily usage of the active compounds and compositions of the present invention will be decided by the attending physician within the scope of sound medical judgment. The specific therapeutically effective dose level for any particular patient will depend upon a variety of factors including the disorder being treated and the severity of the brain injury or ischemia; activity of the specific compound employed; the specific composition employed; the age, body weight, general health, sex and diet of the patient; the time of administration, route of administration, and rate of excretion of the specific compound employed; the duration of the treatment; drugs used in combination or coinciding with the specific compound employed; and like factors well known in the medical arts.

Toxicity and therapeutic efficacy of such compounds can be determined by standard pharmaceutical procedures in cell assays or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell based assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The total daily dose of the active compounds of the present invention administered to a subject in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a human or other mammal in need of such treatment from about 1 mg to about 1000 mg of the active substance(s) of this invention per day in multiple doses or in a single dose of from 1 mg, 5 mg, 10 mg, 100 mg, 500 mg or 1000 mg.

In certain situations, it may be important to maintain a fairly high dose of the active agent in the blood stream of the patient, particularly early in the treatment. Such a fairly high dose may include a dose that is several times greater than its use in other indications. For example, the typical anti-diabetic dose of oral or IV glibenclamide is about 2.5 mg/kg to about 15 mg/kg per day; the typical anti-diabetic dose of oral or IV tolbutamide is about to 0.5 gm/kg to about 2.0 gm/kg per day; the typical anti-diabetic dose for oral gliclazide is about 30 mg/kg to about 120 mg/kg per day; however, much larger doses may be required to block neural cell swelling and brain swelling.

For example, in one embodiment of the present invention directed to a method of preventing neural cell swelling in the brain of a subject by administering to the subject a formulation containing an effective amount of a compound that blocks the $NC_{Ca-ATP}$ channel and a pharmaceutically acceptable carrier, such formulations may contain from about 0.1 to about 100 grams of tolbutamide or from about 0.5 to about 150 milligrams of glibenclamide. In another embodiment of the present invention directed to a method of alleviating the negative effects of traumatic brain injury or cerebral ischemia stemming from neural cell swelling in a subject by administering to the subject a formulation containing an effective amount of a compound that blocks the $NC_{Ca-ATP}$ channel and a pharmaceutically acceptable carrier.

In situations of traumatic brain injury or cerebral ischemia (such as stroke), or cerebral hypoxia, it may be important to maintain a fairly high dose of the active agent to ensure delivery to the brain of the patient, particularly early in the treatment. Hence, at least initially, it may be important to keep the dose relatively high and/or at a substantially constant level for a given period of time, preferably, at least about six or more hours, more preferably, at least about twelve or more hours and, most preferably, at least about twenty-four or more hours. In situations of traumatic brain injury or cerebral ischemia (such as stroke), it may be important to maintain a fairly high dose of the active agent to ensure delivery to the brain of the patient, particularly early in the treatment.

When the method of the present invention is employed to treat conditions involving bleeding in the brain, such as traumatic brain injury or cerebral ischemia (such as stroke), delivery via the vascular system is available and the compound is not necessarily required to readily cross the blood-brain barrier.

Formulations and Administration

The compounds of the present invention may be administered alone or in combination or in concurrent therapy with other agents which affect the central or peripheral nervous system, particularly selected areas of the brain.

Liquid dosage forms for oral administration may include pharmaceutically acceptable emulsions, microemulsions, solutions, suspensions, syrups and elixirs containing inert diluents commonly used in the art, such as water, isotonic solutions, or saline. Such compositions may also comprise adjuvants, such as wetting agents; emulsifying and suspending agents; sweetening, flavoring and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulation can be sterilized, for example, by filtration through a bacteria-retaining filter, or by incorporating sterilizing agents in the form of sterile solid compositions, which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug, which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers, such as polylactide-polyglycoside. Depending on the ratio of drug to polymer and the composition of the polymer, the rate of drug release can be controlled. Examples of other biodegradable polymers include polyorthoesters and polyanhydrides. The depot injectables can also be made by entrapping the drug in liposomes or microemulsions, which are compatible with body tissues.

Suppositories for rectal administration of the drug can be prepared by mixing the drug with a suitable non-irritating excipient, such as cocoa butter and polyethylene glycol which are solid at ordinary temperature but liquid at the rectal temperature and will, therefore, melt in the rectum and release the drug.

Solid dosage forms for oral administration may include capsules, tablets, pills, powders, gelcaps and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or patches. Transdermal patches have the added advantage of providing controlled delivery of active compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

The method of the present invention employs the compounds identified herein for both in vitro and in vivo applications. For in vivo applications, the invention compounds can be incorporated into a pharmaceutically acceptable formulation for administration. Those of skill in the art can readily determine suitable dosage levels when the invention compounds are so used.

As employed herein, the phrase "suitable dosage levels" refers to levels of compound sufficient to provide circulating concentrations high enough to effectively block the $NC_{Ca\text{-}ATP}$ channel and prevent or reduce neural cell swelling in vivo.

In accordance with a particular embodiment of the present invention, compositions comprising at least one SUR1 antagonist compound (as described above), and a pharmaceutically acceptable carrier are contemplated.

Exemplary pharmaceutically acceptable carriers include carriers suitable for oral, intravenous, subcutaneous, intramuscular, intracutaneous, and the like administration. Administration in the form of creams, lotions, tablets, dispersible powders, granules, syrups, elixirs, sterile aqueous or non-aqueous solutions, suspensions or emulsions, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use. The active compound is admixed under sterile conditions with a pharmaceutically acceptable carrier and any needed preservatives or buffers as may be required.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention. Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

All references cited herein are incorporated by reference in their entirety herein. Full citations for the references cited herein are provided in the following list.

Adams D J, Dwyer T M, Hille B (1980) The permeability of endplate channels to monovalent and divalent metal cations. J Gen Physiol 75: 493-510.

Aguilar-Bryan L., Nichols C G, Wechsler S W, Clement J P, Boyd A E, 111.

Gonzalez G, Herrera-Sosa H, Nguy K, Bryan J, Nelson D A (1 995) Cloning of the beta cell high-affinity sulfonylurea receptor: a regulator of insulin secretion. Science 268: 423-426.

Barros L F, Stutzin A, Calixto A, Catalan M, Castro J, Hetz C, Hermosilla T (2001) Nonselective cation channels as effectors of free radical-induced rat liver cell necrosis. Hepatology 33: 114-122.

Bordey A, Sontheimer H (1 998) Properties of human glial cells associated with epileptic seizure foci. Epilepsy Res 32: 286-303.

Brismar T, Collins V P (1 993) Effect of external cation concentration and metabolic inhibitors on membrane potential of human glial cells. J Physiol (Lond) 460: 365-383.

Champigny G, Verrier B, Lazdunski M (1991) A voltage, calcium, and ATP sensitive non selective cation channel in human colonic tumor cells. Biochem Biophys Res Commun 176: 1 196-1 203.

Christensen O, Hofbann E K (1 992) Cell swelling activates K+ and Cl— channels as well as nonselective, stretch-activated cation channels in Ehrlich ascites tumor cells. J Membr Biol 129: 13-36.

Chuang H, Jan Y N, Jan L Y (1997) Regulation of IRK3 inward rectifier K+ channel by ml acetylcholine receptor and intracellular magnesium. Cell 89: 1 121-1 132.

Cook D I, Poronnik P, Young J A (1990) Characterization of a 25-pS nonselective cation channel in a cultured secretory epithelial cell line. J Membr Biol 114: 37-52.

Fujita A, Kurachi Y (2000) Molecular aspects of ATP-sensitive K+ channels in the cardiovascular system and K+ channel openers. Pharmacol Ther 2000 January: 85 (1):39-53.

Gray M A, Argent B E (1 990) Non-selective cation channel on pancreatic duct cells, Biochim Biophys Acta 1029: 33-42.

Hamill O P, Marty A, Neher E, Salunann B, Sigworth F J (1981) Improved patch-clamp techniques for high-resolution current recording from cells and cell-free membrane patches. Pflugers Arch 391: 85-100.

Harvey J, Hardy S C, Ashford M L (1 999) Dual actions of the metabolic inhibitor, sodium azide on K(ATP) channel currents in the rat CRI-GI insulinoma cell line. Br J Pharmacol 126: 51-60.

Higgins C F (1 992) ABC transporters: from microorganisms to man. Annu Rev Cell Biol 8: 67-1 13.

Horn R, Marty A (1988) Muscarinic activation of ionic currents measured by a new whole-cell recording method. J Gen Physiol 92:145-159.

Inagaki N, Gonoi T, Clement J P, Wang C Z, Aguilar-Bryan L, Bryan J, Seino S (1996) A family of sulfonylurea receptors determines the pharmacological properties of ATP-sensitive K+ channels. Neuron 16:1011-1017.

Isomoto S, Kondo C, Yamada M, Matsumoto S, Higashi-guchi O, Horio Y, Matsuzawa Y, Kurachi Y (1 996) A novel sulfonylurea receptor forms with BIT (Kir6.2) a smooth muscle type ATP-sensitive K+ channel. J Biol Chem 271: 24321-24324.

Johnson M E, Gores G J, Uhl C B, Sill J C (1 994) Cytosolic free calcium and cell death during metabolic inhibition in a neuronal cell line. J Neurosci 14: 4040-4049.

Jurkowitz-Alexander M S, Altschuld R A, Ham S E, Stephens R E, Horrocks L A (1993) Protection of ROC-1 hybridglial cells by polyethylene glycol following ATP depletion. J Neurochem 61:1581-1584.

Jurkowitz-Alexander M S, Altschuld R A, Hohl C M, Johnson J D, McDonald J S, Simmons T D, Horrocks L A (1 992) Cell swelling, blebbing, and death are dependent on ATP depletion and independent of calcium during chemical hypoxia in a glial cell line (ROC-1). J Neurochem 59: 344-352.

Juurlink B H, Chen Y, Hertz L (1992) Can J Physiol Pharmacol 70 Suppl: S344-S349.

Kempski O, von Rosen S, Weigt H, Staub F, Peters J, Baethmann A (1991). Ann NY Acad Sci 633: 306-317.

Kim D, Fu C (1993) Activation of a nonselective cation channel by swelling in atrial cells. J Membr Biol 135: 27-37.

Kimelberg H K, Rutledge E, Goderie S, Charniga C (1 995) Astrocytic swelling due to hypotonic or high K+ medium causes inhibition of glutamate and aspartate uptake and increases their release. J Cereb Blood Flow Metab 15: 409-4 16.

Kimelberg H K, Rose J W, Barron K D, Waniewski R A, Cragoe E J. (1989) Astrocytic swelling in traumatic-hypoxic brain injury. Beneficial effects of an inhibitor of anion exchange transport and glutamate uptake in glial cells. Mol Chem Neuropathol 11(1): 1-31.

Korbmacher C, Volk T, Segal A S, Boulpaep E L, Fromter E (1995) A calcium-activated and nucleotide-sensitive nonselective cation channel in M-1 mouse cortical collecting duct cells. J Membr Biol 146: 29-45.

Kom S J, Marty A, Comer J A, Horn R (1991) Perforated patch recording. In: Methods in Neuroscience. Electrophysiology and Microinjection. (Conn PM, ed), pp 364-373. San Diego: Academic Press.

Lawson K (2000) Potassium channel openers as potential therapeutic weapons in ion channel disease. Kidney Int 2000 March: 57 (3): 838-845.

Lebovitz H E (1 985) Oral hypoglycaemic agents. Amsterdam: Elsevier.

Liu Y, Liu D, Printzenhoff D, Coghlan M J, Harris R, Krafte D S (2002) Tenidap, a novel anti-inflammatory agent, is an opener of the inwardly rectifying K+ channel hKir2.3. Eur. J. Pharmacol. 435: 153-160.

Lomneth R, Gruenstein E I (1 989) Energy-dependent cell volume maintenance in UC-11MG human astrocytornas. Am J Physiol 257: C817-C824.

Majno G, Joris I (1995) Apoptosis, oncosis, and necrosis. An overview of cell death. Am J Path 01 146: 3-15.

Maruyama Y, Petersen O H (1984) Single calcium-dependent cation channels in mouse pancreatic acinar cells. J Membr Biol 81: 83-87.

Mongin A A, Cai 2, Kimelberg H K (1 999) Volume-dependent taurine release from cultured astrocytes requires permissive $[Ca^{2+}]i$ and calmodulin. Am J Physiol 277: C823-C832.

Nichols C G, Shyng S L, Nestorowicz A, Glaser B, Clement J P, Gonzalez G, Aguilar-Bryan L, Permutt M A, Bryan J (1996) Adenosine diphosphate as an intracellular regulator of insulin secretion. Science 272: 1785-1787.

Ono S, Mougouris T, DuBose T D, Jr., Sansom S C (1994) ATP and calcium modulation of nonselective cation channels in IMCD cells. Am J Physiol 267: F558-F565.

Panten U, Bwgfeld J, Goerke F, Rennicke M, Schwanstecher M, Wallasch A, Zunkler B J, Lenzen S (1989) Control of insulin secretion by sulfonylureas, meglitinide and diazoxide in relation to their binding to the sulfonylurea receptor in pancreatic islets. Biochem Pharmacol 38: 1217-1229.

Perillan P R, Chen M, Potts E A, Simard J M (2002) Transforming growth factor-b 1 regulates Kir2.3 inward rectifier K+ channel via phospholipase C and protein kinase C-d in reactive astrocytes from adult rat brain. J. Biol. Chem. 277: 1974-1980.

Perillan P R, Li X, Potts E A, Chen M, Bredt D S, Simard J M (2000) Inward rectifier K+ channel Kir2.3 (W) in reactive astrocytes from adult rat brain. Glia 31: 181-192.

Perillan P R, Li X, Simard J M (1 999) K+ inward rectifier currents in reactive astrocytes from adult rat brain. Glia 27: 213-225.

Popp R, Gogelein H (1992) A calcium and ATP sensitive nonselective cation channel in the antiluminal membrane of rat cerebral capillary endothelial cells. Biochim Biophys Acta 1108: 59-66.

Rae J L, Dewey J, Cooper K, Gates P (1990) A non-selective cation channel in rabbit corneal endothelium activated by internal calcium and inhibited by internal ATP. Exp Eye Res 50: 373-384.

Ransom C B, Sontheimer H (1995) Biophysical and pharmacological characterization of inwardly rectifying K+ currents in rat spinal cord astrocytes. J Neurophysiol 73: 333-346.

Renkin E M (1955) Filtration, diffusion, and molecular sieving through porous cellulose membranes. J Gen Physiol 38: 225-243.

Robinson R A, Stokes R H (1970) Electrolyte Solutions. London: Buttenvorths.

Rose C R, Waxman S G, Ransom B R (1998) Effects of glucose deprivation, chemical hypoxia, and simulated ischemia on Na+ homeostasis in rat spinal cord astrocytes. J Neurosci 18: 3554-3562.

Rucker-Martin C, Henaff M, Hatem S N, Delpy E, Mercadier J J (1999) Early redistribution of plasma membrane phosphatidylserine during apoptosis of adult rat ventricular myocytes in vitro. Basic Res Cardiol 94: 171-179.

Rutledge E M, Kimelberg H K (1996) Release of [3H]-D-aspartate from primary astrocyte cultures in response to raised external potassium. J Neurosci 16: 7803-78 1 1.

Schroder W, Hager G, Kouprijanova E, Weber M, Schmitt A B, Seifert G, Steirihauser C (1999) Lesion-induced changes of electrophysiological properties in astrocytes of the rat dentate gyrus. Glia 28: 166-1 74.

Shyng S, Ferrigni T, Nichols C G (1 997) Control of rectification and gating of cloned $K_{ATP}$ channels by the Kir6.2 subunit. J Gen Physiol 110: 141-153.

Sigworth F J, Sine S M (1987) Data transformations for improved display and fitting of single-channel dwell time histograms. Biophys J 52: 1047-1 054.

Staub F, Peters J, Kempski O, Schneider G H, Schurer L, Baethmann A (1993) Swelling of glial cells in lactacidosis and by glutamate: significance of Cl—-transport. Brain Res 610: 69-74.

Sturgess N C, Hales C N, Ashford M L (1 987) Calcium and ATP regulate the activity of a non-selective cation channel in a rat insulinoma cell line. Pflugers Arch 409: 607-6 1 5.

Swanson R A (1 992) Astrocyte glutamate uptake during chemical hypoxia in vitro. Neurosci Lett 147: 143-146.

Tanaka S, Uehara T, Nomura Y (2000) Up-regulation of protein-disulfide isomerase in response to hypoxiahrain ischemia and its protective effect against apoptotic cell death. J Biol Chem 275: 10388-10393.

Ubl J, Murer H, Kolb H A (1988) Ion channels activated by osmotic and mechanical stress in membranes of opossum kidney cells. J Membr Biol 104: 223-232.

Walz W, Gimpl G, Ohlemeyer C, Kettenmann H (1994) Extracellular ATP-induced currents in astrocytes: involvement of a cation channel. J Neurosci Res 38: 12-18.

Yu A C, Wong H K, Yung H W, Lau L T (2001) Ischemia-induced apoptosis in primary-cultures of astrocytes. Glia 35: 121-130.

What is claimed is:

1. A method of treating a subject for central or peripheral nervous system damage, said damage comprising expression of a $NC_{Ca-ATP}$ channel in neural cells, comprising administering a pharmaceutical composition comprising a compound effective to inhibit the activity of a $NC_{Ca-ATP}$ channel in a neural cell and a pharmaceutically acceptable carrier to the subject, wherein the compound is a sulfonylurea receptor 1 (SUR1) antagonist selected from a sulfonylurea compound, a benzamido derivative, LY397364, LY389382, and a combination thereof, wherein said administration of the SUR1 antagonist inhibits the $NC_{Ca-ATP}$ channel in neural cells expressing the channel, thereby treating said central or peripheral nervous system damage.

2. The method of claim 1, wherein the central or peripheral nervous system damage comprises traumatic brain injury, cerebral ischemia, hypoxia, or bleeding in the brain.

3. The method of claim 1, wherein the subject has suffered a stroke.

4. The method of claim 1, wherein said composition is administered intravenously, subcutaneously, orally, intramuscularly, intracutaneously, intragastricly, or directly into the brain.

5. The method of claim 1, wherein the SUR1 antagonist is a glibenclamide, a tolbutamide, a repaglinide, a nateglinide, a meglitinide, LY397364, LY389382, a gliclazide, a glimepiride, and combinations thereof.

6. The method of claim 1, wherein the SUR1 antagonist is a glibenclamide.

7. The method of claim 6, wherein the glibenclamide is administered to the subject at a dose between about 0.5 milligrams and 150 milligrams.

8. The method of claim 6, wherein the glibenclamide is administered to the subject in a dose of 1 mg to 1000 mg per day.

9. The method of claim 6, wherein the glibenclamide is administered to the subject in a dose of 1 mg to 100 mg per day.

10. The method of claim 6, wherein the glibenclamide is administered to the subject in a dose of 1 mg to 10 mg per day in a single dose or multiple doses.

11. The method of claim 6, wherein the glibenclamide is administered to the subject in a dose of 1 mg to 5 mg per day in a single dose.

12. The method of claim 6, wherein the glibenclamide is administered in combination with one or more further active agents that affect the subject's central or peripheral nervous system.

13. The method of claim 5, wherein the SUR1 antagonist is administered in the form of capsules, tablets, pills, powders, gelcaps, or granules to the subject.

14. The method according to claim 1, further comprising administering MgADP to the subject.

15. The method of claim 1, wherein the SUR1 antagonist is administered to the subject in a dose at a substantially constant level for a given period of time.

16. The method of claim 15, wherein the given period of time is about six or more hours.

17. The method of claim 15, wherein the given period of time is about twelve or more hours.

18. The method of claim 15, wherein the given period of time is about twenty-four or more hours.

* * * * *